(12) United States Patent
Bornstein

(10) Patent No.: US 8,506,979 B2
(45) Date of Patent: Aug. 13, 2013

(54) NEAR-INFRARED ELECTROMAGNETIC MODIFICATION OF CELLULAR STEADY-STATE MEMBRANE POTENTIALS

(75) Inventor: Eric Bornstein, Natick, MA (US)

(73) Assignee: Nomir Medical Technologies, Inc., Natick, MA (US)

( * ) Notice: Subject to any disclaimer, the term of this patent is extended or adjusted under 35 U.S.C. 154(b) by 1242 days.

(21) Appl. No.: 11/981,431

(22) Filed: Oct. 31, 2007

(65) Prior Publication Data
US 2008/0139992 A1 Jun. 12, 2008

Related U.S. Application Data

(63) Continuation-in-part of application No. PCT/US2006/030434, filed on Aug. 3, 2006, which is a continuation-in-part of application No. PCT/US2006/028616, filed on Jul. 21, 2006, application No. 11/981,431, which is a continuation-in-part of application No. 10/776,106, filed on Feb. 11, 2004, now abandoned, which is a continuation-in-part of application No. 10/649,910, filed on Aug. 26, 2003, now abandoned.

(60) Provisional application No. 60/705,630, filed on Aug. 3, 2005, provisional application No. 60/701,896, filed on Jul. 21, 2005, provisional application No. 60/711,091, filed on Aug. 23, 2005, provisional application No. 60/780,998, filed on Mar. 9, 2006, provisional application No. 60/789,090, filed on Apr. 4, 2006, provisional application No. 60/406,493, filed on Aug. 28, 2002, provisional application No. 60/874,424, filed on Dec. 12, 2006.

(51) Int. Cl.
*A61F 2/02* (2006.01)

(52) U.S. Cl.
USPC .......................................................... 424/422

(58) Field of Classification Search
None
See application file for complete search history.

(56) References Cited

U.S. PATENT DOCUMENTS

| 4,669,466 A | 6/1987 | L'Esperance |
| 4,917,084 A | 4/1990 | Sinofsky |

(Continued)

FOREIGN PATENT DOCUMENTS

| WO | WO 91/13652 | 9/1991 |
| WO | WO 00/01294 | 1/2000 |

(Continued)

OTHER PUBLICATIONS http://users.rcn.com/jkimball.ma.ultranet/BiologyPages/A/Antibiotics.html, 2010.*

(Continued)

*Primary Examiner* — Carlos Azpuru
(74) *Attorney, Agent, or Firm* — Foley & Lardner LLP; Matthew L. Fenselau

(57) ABSTRACT

Systems and methods are disclosed herein for applying near-infrared optical energies and dosimetries to alter the bioenergetic steady-state trans-membrane and mitochondrial potentials ($\Delta\Psi$-steady) of all irradiated cells through an optical depolarization effect. This depolarization causes a concomitant decrease in the absolute value of the trans-membrane potentials $\Delta\Psi$ of the irradiated mitochondrial and plasma membranes. Many cellular anabolic reactions and drug-resistance mechanisms can be rendered less functional and/or mitigated by a decrease in a membrane potential $\Delta\Psi$, the affiliated weakening of the proton motive force $\Delta p$, and the associated lowered phosphorylation potential $\Delta Gp$. Within the area of irradiation exposure, the decrease in membrane potentials $\Delta\Psi$ will occur in bacterial, fungal and mammalian cells in unison. This membrane depolarization provides the ability to potentiate antimicrobial, antifungal and/or antineoplastic drugs against only targeted undesirable cells.

32 Claims, 18 Drawing Sheets

$\Delta\Psi$- TRANS - BACT, $\Delta\Psi$-TRANS - MITO - MAM AND
$\Delta\Psi$- TRANS - MITO - FUNGI DURING AND AFTER
NIMELS IRRADIATION

(56) References Cited

U.S. PATENT DOCUMENTS

| | | | |
|---|---|---|---|
| 4,945,239 | A | 7/1990 | Wist et al. |
| 5,196,004 | A | 3/1993 | Sinofsky |
| 5,464,436 | A | 11/1995 | Smith |
| 5,595,568 | A | 1/1997 | Anderson et al. |
| 5,683,380 | A | 11/1997 | Eckhouse |
| 5,693,043 | A | 12/1997 | Kittrell et al. |
| 5,735,844 | A | 4/1998 | Anderson et al. |
| 5,849,035 | A | 12/1998 | Pathak et al. |
| 5,853,407 | A | 12/1998 | Miller |
| 5,954,710 | A | 9/1999 | Paolini |
| 6,015,404 | A | 1/2000 | Altshuler et al. |
| 6,042,603 | A | 3/2000 | Fisher et al. |
| 6,080,146 | A | 6/2000 | Altshuler et al. |
| 6,090,788 | A | 7/2000 | Lurie |
| 6,104,959 | A | 8/2000 | Spertell |
| 6,123,923 | A | 9/2000 | Unger et al. |
| 6,149,644 | A | 11/2000 | Xie |
| 6,235,016 | B1 | 5/2001 | Stewart |
| 6,273,884 | B1 | 8/2001 | Altshuler et al. |
| 6,283,986 | B1 | 9/2001 | Johnson |
| 6,387,089 | B1 | 5/2002 | Kreindel et al. |
| 6,454,791 | B1 | 9/2002 | Prescott |
| 6,475,138 | B1 | 11/2002 | Schechter et al. |
| 6,508,813 | B1 | 1/2003 | Altshuler |
| 6,514,243 | B1 | 2/2003 | Eckhouse et al. |
| 6,517,532 | B1 | 2/2003 | Altshuler et al. |
| 6,605,080 | B1 | 8/2003 | Altshuler et al. |
| 6,648,904 | B2 | 11/2003 | Altshuler et al. |
| 6,662,054 | B2 | 12/2003 | Kreindel et al. |
| 6,702,808 | B1 | 3/2004 | Kreindel |
| 6,815,209 | B2 | 11/2004 | Baeummer et al. |
| 6,824,542 | B2 | 11/2004 | Jay |
| 6,878,144 | B2 | 4/2005 | Altshuler et al. |
| 6,887,261 | B1 | 5/2005 | Peyman |
| 6,889,090 | B2 | 5/2005 | Kreindel |
| 6,890,346 | B2 | 5/2005 | Ganz et al. |
| 6,902,563 | B2 | 6/2005 | Wilkens et al. |
| 6,939,344 | B2 | 9/2005 | Kreindel |
| 6,960,201 | B2 | 11/2005 | Cumbie |
| 7,041,100 | B2 | 5/2006 | Kreindel |
| 7,060,061 | B2 | 6/2006 | Altshuler et al. |
| 7,090,497 | B1 | 8/2006 | Harris |
| 7,118,563 | B2 | 10/2006 | Weckwerth et al. |
| 2003/0023284 | A1 | 1/2003 | Gartstein et al. |
| 2003/0054321 | A1 | 3/2003 | Moran |
| 2003/0130709 | A1 | 7/2003 | D.C. et al. |
| 2003/0208249 | A1 | 11/2003 | Chen |
| 2004/0034341 | A1 | 2/2004 | Altshuler et al. |
| 2004/0093042 | A1 | 5/2004 | Altshuler et al. |
| 2004/0111132 | A1 | 6/2004 | Shenderova et al. |
| 2004/0156743 | A1 | 8/2004 | Bornstein |
| 2004/0210276 | A1 | 10/2004 | Altshuler et al. |
| 2005/0065577 | A1 | 3/2005 | McArthur et al. |
| 2005/0075703 | A1 | 4/2005 | Larsen |
| 2005/0107853 | A1 | 5/2005 | Krespi et al. |
| 2006/0004425 | A1 | 1/2006 | Cumbie |
| 2006/0200213 | A1 | 9/2006 | McDaniel |
| 2007/0179570 | A1 | 8/2007 | De Taboada et al. |
| 2007/0197884 | A1 | 8/2007 | Bornstein |

FOREIGN PATENT DOCUMENTS

| | | |
|---|---|---|
| WO | WO 01/74265 | 10/2001 |
| WO | WO 02/086550 | 10/2002 |
| WO | WO 03/049892 | 6/2003 |
| WO | WO 03/079883 | 10/2003 |
| WO | WO 03/086215 | 10/2003 |
| WO | WO 04/000150 | 12/2003 |
| WO | WO 2004/024144 | 3/2004 |
| WO | WO 2004/058352 | 7/2004 |
| WO | WO 2006/076506 | 7/2006 |

OTHER PUBLICATIONS http://en.wikipedia.org/wiki/Rapamycin, 2012.*

PCT International Search Report—(PCT/US08/82113) Date of Mailing Apr. 22, 2009.

PCT International Search Report—(PCT/US08/82130) Date of Mailing Apr. 29, 2009.

Schamberger, et al., "Hydrophobic Ion Hydration and the Magnitude of the Dipole Potential", Biophysical Journal, Jun. 2002, vol. 82, pp. 3081-3088.

Paglin, et al., "Rapamycine-Sensitive Pathway Regulates Mitochondrial Potential, Autophagy, and Survival in Irradiated MCF-7 Cells", Cancer Research, Dec. 1, 2005, vol. 65, pp. 11061-11070.

Kim, et al., "Arisostatins A Induces Apoptosis Through the Activation of Caspase-3 and Reactive Oxygen Species Generation in AMC-HN-4 cells", Biochemical and Biophysical Research Communication, 2003, vol. 309I, pp. 449-456.

Hujer, et al., "Structure-Activity Relationships of Different beta-Lactam Antibiotics against a Soluble Form of Enterococcus faecium PBP5, a Type II Bacterial Transpeptidase", Antimicrobial Agents and Chemotherapy, 2005, vol. 49, pp. 612-618.

Stone, et al., "Mechanism of Action of bacitracin: Complexation with Metal Ion and C55-Isoprenyl Pyrophosphate", Proceedings of the National Academy of Science, USA, 1971, vol. 68, pp. 3223-3227.

Matassova, et al., "Ribosomal RNA is the target of Oxazolidionones, a Novel Clas of Translational Inhinitors", RNA, 1999, vol. 5, pp. 939-947.

Hurdle, et al., "Prospects for Aminoacyl-tRNA Synthetase Inhibitors as New Antimicrobial Agents", Antimicrobial Agents and Chemotherapy, 2005, vol. 49, pp. 4821-4833.

Zhi, et al., "Hybrid Antibacterials. DNA polymerase: topoisomerase inhibitors", Journal of Medical Chemistry, 2006, vol. 49, pp. 1455-1465.

Iwamoto, et al., "Local Exposure of Phoshatidylethanolamine on the Yeast Plasma Memebrane is implicated in Cell Polarity", Genes to Cells, 2004, vol. 9, pp. 891-903.

Choi, et al., "beta-Ketoacyl-Acyl Carrier Protein Synthase III (FabH) is a Determining Factor in Branched-Chain Fatty Acid Biosynthesis", Journal of Bacteriology, 2000, vol. 182, pp. 365-370.

Aguilera, et al., "Permeabilizing Action of an Antimicrobial Lactoferricin-Derived Peptide on Bacterial and Artificial Membranes", FEBS Letters, 1999, vol. 462, pp. 273-277.

Fritsche, et al., "Comparative Antimicrobial Characterization of LBM415 (NVP PDF-713), a New Peptide Deformylase Inhibitor of Clinical Importance", Antimicrobial Agents and Chemotherapy, 2005, vol. 49, pp. 1468-1476.

PCT International Search Report—(PCT/US07/87264) Date of Mailing Sep. 2, 2008.

Liang, et al., Wavelength Dependence of Cell Cloning Efficiency after Optical Trapping, Biophy.J. Mar. 1996, pp. 1529-1533, vol. 70.

Neuman, et al., Characterization of Photodamage to *Escherichia coli* in Optical Traps, Biophy J. Nov. 1999, pp. 2865-2863, vol. 77.

Neuman, K.C., Single Molecule Study of RNA Polymerase Transcription Under Load, Ph. D. Dissertation presented to Princeton University, Nov. 2002, 120 pp.

Karu, et al., Effects of Near-Infrared Laser and Superluminous Diode Irradiation on *Escherichia coli* Division Rate, IEEE Journal of Quantum Elect, Dec. 1990, vol. 26, No. 112.

Bornstein E., S. Gridley, and P. Wegender "Photodamage to Multidrug-resistant Gram-positive and Gram-negative Bacteria by 870 nm/930nm Light Potentiates Erythromycin, Tetracycline and Ciprofloxacin", Photochemistry and Photobiology, 2010 vol. 86 Issue 3, pp. 617-627.

Bornstein et al, "Near-infrared Photoinactivation of Bacteria and Fungi at Physiologic Temperatures" Photochemistry and Photobiology, 2009, 85:1364-1374.

Bornstein, Eric et al; "Antifungal Synergy Produced in *Candida albicans* with 870nm/930nm Near Infrared Photo-damage" IMC9 The Biology of Fungi; 9th International Mycological Congress, Future strategies for the control of fungal diseases, Edinburgh UK. Aug. 1-6, 2010.

* cited by examiner

PHOSPHOLIPID BILAYER

PHOSPHOLIPID

ΔΨ- STEADY - BACT,   ΔΨ-STEADY - MITO MAM, AND
ΔΨ- STEADY - MITO - FUNGI PRIOR TO NIMELS IRRADIATION

ΔΨ- TRANS - BACT,   ΔΨ-TRANS - MITO - MAM AND
ΔΨ- TRANS - MITO - FUNGI DURING AND AFTER
    NIMELS IRRADIATION

TRANS-MEMBRANE PROTEINS

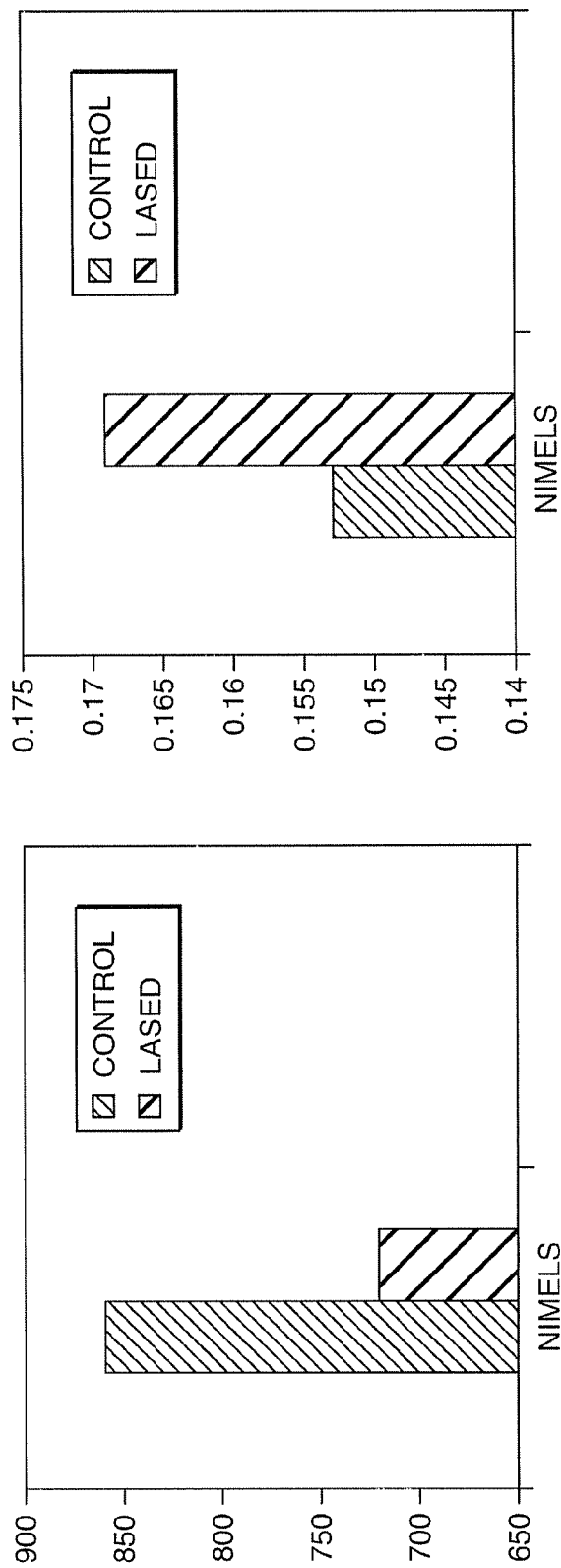

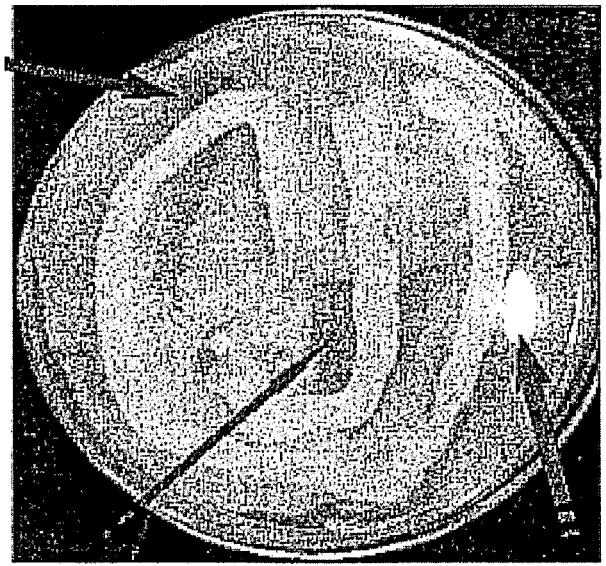
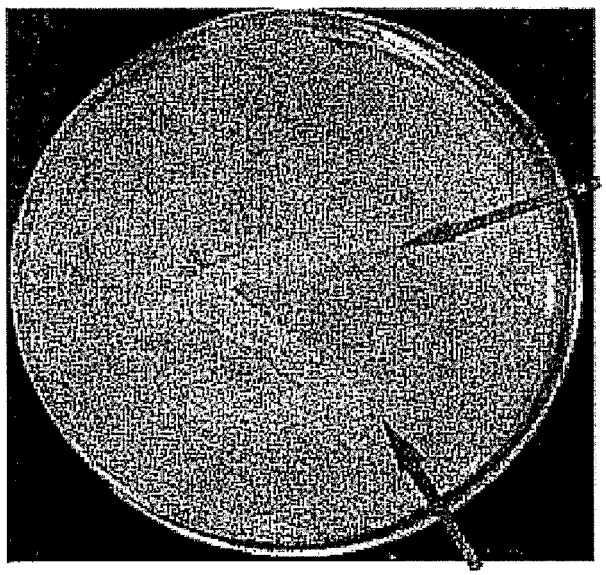
FIG. 16

NEAR-INFRARED ELECTROMAGNETIC MODIFICATION OF CELLULAR STEADY-STATE MEMBRANE POTENTIALS

RELATED APPLICATIONS

This application is a continuation-in-part of International Application No. PCT/US2006/030434 filed 3 Aug. 2006, which claimed the benefit of U.S. Provisional Application Serial No. 60/705,630, filed 3 Aug. 2005; and a continuation-in-part of International Application No. PCT/US2006/028616 filed 21 Jul. 2006, which claimed priority to U.S. Provisional Patent Application Serial No. 60/701,896, filed Jul. 21, 2005; U.S. Provisional Patent Application Serial No. 60/711,091, filed Aug. 23, 2005; U.S. Provisional Patent Application Serial No. 60/780,998, filed Mar. 9, 2006; and U.S. Provisional Patent Application Serial No. 60/789,090, filed Apr. 4, 2006.; this application is also a continuation-in-part of U.S. application Ser. No. 10/776,106 filed 11 Feb. 2004 now abandoned, which is a continuation-in-part of U.S. application Ser. No. 10/649,910 filed 26 Aug. 2003 now abandoned, which claimed priority to U.S. Provisional Patent Application No. 60/406,493 filed 28 Aug. 2002; this application is also related to U.S. Provisional Application 60/874,424, filed 12 Dec. 2006; the contents of all of which applications are incorporated herein by reference in their entireties.

FIELD OF THE INVENTION

The present invention generally relates to methods and systems for generating infrared optical radiation in selected energies and dosimetries that will modify the bioenergetic steady-state trans-membrane and mitochondrial potentials of irradiated cells through a depolarization effect, and more particularly, relates to methods and systems for membrane depolarization to potentiate antimicrobial and antifungal compounds in target bacterial and/or fungal and/or cancer cells.

BACKGROUND OF THE INVENTION

The universal rise of bacteria, fungi and other biological contaminants resistant to antimicrobial agents presents humanity with a grievous threat to its very existence. Since the advent of sulfa drugs (sulfanilamide, first used in 1936) and penicillin (1942, Pfizer Pharmaceuticals), exploitation of significant quantities of antimicrobial agents of all kinds across the planet has created a potent environment for the materialization and spread of resistant contaminants and pathogens. Certain resistant contaminants take on an extraordinary epidemiological significance, because of their predominance in hospitals and the general environment. Widespread use of antibiotics not only prompts generation of resistant bacteria; such as, for example, methicillin-resistant *staphylococcus aureus* (MRSA) and vancomycin-resistant enterococci (VRE); but also creates favorable conditions for infection with the fungal organisms (mycosis), such as, *Candida*.

While potent antifungal agents exist that are microbicidal (e.g., amphotericin B (AmB)), the attributable mortality of candidemia still remains about 38%. In some instances, to treat drug-resistant fungi, high doses of AmB must be administered which frequently result in nephrotoxicity and other adverse effects. Moreover, overuse of antimicrobial agents or antibiotics can cause bioaccumulation in living organisms which may also be cytotoxic to mammalian cells. Given the increasing world's population and the prevalence of drug resistant bacteria and fungi, the rise in incidence of bacterial or fungal infections is anticipated to continue unabated for the foreseeable future.

Currently, available therapies for bacterial and fungal infections include administration of antibacterial and antifungal therapeutics or, in some instances, application of surgical debridement of the infected area. Because antibacterial and antifungal therapies alone are rarely curative, especially in view of newly emergent drug resistant pathogens and the extreme morbidity of highly disfiguring surgical therapies, it has been imperative to develop new strategies to treat or prevent microbial infections.

Therefore, there exist a need for methods and systems that can reduce the risk of bacterial or fungal infections, in/at a given target site, without intolerable risks and/or intolerable adverse effects to biological moieties (e.g., a mammalian tissue, cell or certain biochemical preparations such as a protein preparation) other than the targeted bacteria and fungi (biological contaminants).

SUMMARY OF THE INVENTION

The present invention is directed to methods and systems for reducing the minimum inhibitory concentration (MIC) of antimicrobial molecules (antimicrobial agents) and/or antineoplastice molecules (antineoplastic agents) necessary to attenuate or eliminate microbial and/or neoplastic-related pathology, so that the agents that would otherwise be no longer functional at safe human doses will again be useful as adjunctive therapy. According to methods and systems of the present invention, near infrared optical radiation in selected energies and dosimetries (herein known as NIMELS, standing for "near infrared microbial elimination system") are used to cause a depolarization of all membranes within the irradiated field, that will alter the absolute value of the membrane potential $\Delta\Psi$ of the irradiated cells.

Other features and advantages of the present invention will be set forth in the detailed description of embodiments that follow, and in part will be apparent from the description or may be learned by practice of the invention. Such features and advantages of the invention will be realized and attained by the systems, methods, and apparatus particularly pointed out in the written description and claims appended hereto.

BRIEF DESCRIPTION OF THE DRAWINGS

Aspects of the invention may more fully be understood from the following description when read together with the accompanying drawings, which are to be regarded as illustrative in nature, and not limiting. The drawings are not necessarily to scale, emphasis instead being placed on the principles of the invention.

In the drawings:

FIG. 10 shows the effects of NIMELS irradiation (at a single dosimetry) on *C. albicans* mitochondrial membrane potential which is measured by red fluorescence emission intensities in control and lased samples; and the effects of NIMELS irradiation (at a single dosimetry) on *C. albicans* mitochondrial membrane potential which is measured as ratio of red to green fluorescence in control and lased samples;

FIG. 16 shows the synergistic effects of NIMELS and bacitracin in growth inhibition of MRSA colonies; arrows indicate the growth or a lack thereof of MRSA colonies in the two samples shown; images show that bacitracin is being potentiated by sub-lethal NIMELS dosimetry.

Figures 1, 2:
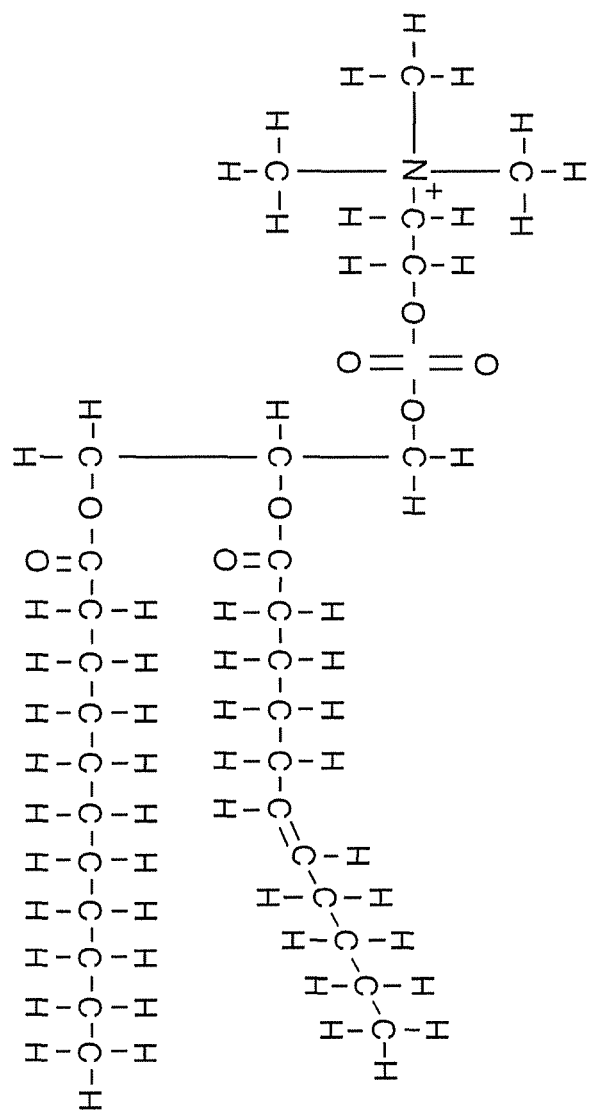
FIG. 1 shows a typical phospholipid bilayer.
FIG. 2 shows the chemical structure of a phospholipid.

While certain embodiments depicted in the drawings and described in relation to the same, one skilled in the art will appreciate that the embodiments depicted are illustrative and that variations of those shown, as well as others described herein, may be envisioned and practiced and be within the scope of the present invention.

DETAILED DESCRIPTION OF THE INVENTION

As used in this specification, the singular forms "a", "an" and "the" also encompass the plural forms of the terms to which they refer, unless the content clearly dictates otherwise. For example, reference to "a NIMELS wavelength" includes any wavelength within the ranges of the NIMELS wavelengths described, as well as combinations of such wavelengths.

As used herein, unless specifically indicated otherwise, the word "or" is used in the "inclusive" sense of "and/or" and not the "exclusive" sense of "either/or."

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The present invention is directed to methods and systems for reducing the minimum inhibitory concentration (MIC) of antimicrobial molecules (agents) and/or antineoplastic molecules (agents) necessary to attenuate or eliminate microbial and/or neoplastic-related pathology, so that the antimicrobial agents that would otherwise be no longer functional at safe human doses will again be useful as adjunctive therapy. According to methods and systems of the present invention, near infrared optical radiation in selected energies and dosimetries (herein known as NIMELS, standing for "near infrared microbial elimination system") are used to cause a depolarization of membranes within the irradiated field, that will alter the absolute value of the membrane potential ΔΨ of the irradiated cells.

This altered ΔΨ will cause an affiliated weakening of the proton motive force Δp, and the bioenergetics of all affected membranes. Accordingly, the effects of NIMELS irradiation (NIMELS effect) can potentiate existing antimicrobial molecules against microbes infecting and causing harm to human hosts. These effects will render less functional many cellular anabolic reactions (e.g., cell wall formation) and drug-resistance mechanisms (e.g., efflux pumps) that require chemiosmotic electrochemical energy to function. Hence, any membrane bound cellular resistance mechanisms or anabolic reaction that makes use of the membrane potential ΔΨ, proton motive force Δp, or the phosphorylation potential ΔGp for their functional energy needs, will be affected by the methods and systems of the present invention.

The methods and systems of the present invention utilize optical radiation to potentiate antimicrobial and or antifungal drugs against only targeted undesirable cells (e.g., MRSA or *Candida* infection in skin) with a selectivity made possible by the fact that mammalian cells are not generally affected by treatments (with molecules or drugs) that are intended to damage the bacterial or fungal cells.

In exemplary embodiments, the applied optical radiation used in accordance with methods and systems of the present invention includes one or more wavelengths ranging from about 850 nm to about 900 nm, at a NIMELS dosimetry, as described herein. In one aspect, wavelengths from about 865 nm to about 875 nm are utilized. In another aspect, such applied radiation has a wavelength from about 905 nm to about 945 nm at a NIMELS dosimetry. In one aspect, such applied optical radiation has a wavelength from about 925 nm to about 935 nm. In a particular aspect, a wavelength of (or narrow wavelength range including) 930 nm can be employed. In some aspects of the present invention, multiple wavelength ranges include 870 and 930 nm, respectively.

Microbial pathogens whose bioenergetic systems can be affected by the NIMELS according to the present invention include microorganisms such as, for example, bacteria, fungi, molds, mycoplasms, protozoa, and parasites.

In one embodiment, the methods and systems of the present invention are used in treating, reducing and/or eliminating the infectious entities known to cause cutaneous or wound infections such as staphyloccocci and enterococci. Staphylococcal and enterococcal infections can involve almost any skin surface on the body known to cause skin conditions such as boils, carbuncles, bullous impetigo and scalded skin syndrome. *S. aureus* is also the cause of staphylococcal food poisoning, enteritis, osteomilitis, toxic shock syndrome, endocarditis, meningitis, pneumonia, cystitis, septicemia and post-operative wound infections. Staphylococcal infections can be acquired while a patient is in a hospital or long-term care facility. The confined population and the widespread use of antibiotics have led to the development of antibiotic-resistant strains of *S. aureus*. These strains are called methicillin resistant *staphylococcus aureus* (MRSA). Infections caused by MRSA are frequently resistant to a wide variety of antibiotics (especially β-lactams) and are associated with significantly higher rates of morbidity and mortality, higher costs, and longer hospital stays than infections caused by non-MRSA microorganisms. Risk factors for MRSA infection in the hospital include colonization of the nares, surgery, prior antibiotic therapy, admission to intensive care, exposure to a MRSA-colonized patient or health care worker, being in the hospital more than 48 hours, and having an indwelling catheter or other medical device that goes through the skin.

In another embodiment, the methods and systems of the present invention are used in treating, reducing and/or eliminating the infectious entities known as cutaneous Candidiasis. These *Candida* infections involve the skin, and can occupy almost any skin surface on the body. However, the most often occurrences are in warm, moist, or creased areas (such as armpits and groins). Cutaneous candidiasis is extremely common. *Candida* is the most common cause of diaper rash, where it takes advantage of the warm moist conditions inside the diaper. The most common fungus to cause these infections is *Candida albicans*. *Candida* infection is also very common in individuals with diabetes and in the obese. *Candida* can also cause infections of the nail, referred to as onychomycosis, infections of the skin surrounding the nail (paronychia) and infections around the corners of the mouth, called angular cheilitis.

The term "NIMELS dosimetry" denotes the power density (W/cm$^2$) and the energy density (J/cm$^2$) (where 1 Watt=1 Joule per second) values at which a subject wavelength according to the invention is capable of generating a reactive oxygen species ("ROS") and thereby reduce the level of a biological contaminant in a target site. The term also includes irradiating a cell to increase the sensitivity of the biological contaminant through the lowering of $\Delta\Psi$ with the concomitant generation of ROS of an antimicrobial or antineoplastic agent, wherein the contaminant is resistant to the agent otherwise. This method can be effected without intolerable risks and/or intolerable side effects on the host subject's tissue other than the biological contaminant.

By "potentiation" of an anti-fungal or antibacterial or antineoplastic agent, it is meant that the methods and systems of this invention counteract the resistance mechanisms in the fungi, bacteria, or cancer sufficiently for the agent to inhibit the growth and/or proliferation of said fungi, bacteria, or cancer at a lower concentration than in the absence of the present methods and systems. In cases where resistance is essentially complete, i.e., the agent has no effect on the cells, potentiation means that the agent will inhibit the growth and/or proliferation of pathogenic cells thereby treating the disease state at a therapeutically acceptable dosage.

As used herein, the term "microorganism" refers to an organism that is microscopic and by definition, too small to be seen by the human eye. For the purpose of this invention, microorganisms can be bacteria, fungi, archaea, protists, and the like. The word microbial is defined as pertaining or relating to microorganisms.

As used herein, the term "cell membrane (or plasma membrane or mitochondrial membrane)" refers to a semi-permeable lipid bilayer that has a common structure in all living cells. It contains primarily proteins and lipids that are involved in a myriad of important cellular processes. Cell membranes that are the target of the present invention have protein/lipid ratios of >1. Stated another way, none of the target membranes in the containment (or moiety, i.e., host tissue) contain greater than 49.99% lipid by dry weight.

As used herein, the term "mitochondria" refers to membrane-enclosed organelles, found in most eukaryotic cells (mamallian cells and fungi). Mitochondria are the "cellular power plants," because they generate most of the eukaryotic cell's supply of ATP, used as a source of chemical energy for the cell. The mitochondria contain inner and outer membranes composed of phospholipid bilayers and proteins. The two membranes, however, have different properties. The outer mitochondrial membrane, encloses the entire organelle, has a protein-to-phospholipid ratio similar to the eukaryotic plasma membrane, and the inner mitochondrial membrane forms internal compartments known as cristae and has a protein-to-phospholipid ratio similar to prokaryote plasma membranes. This allows for a larger space for the proteins such as cytochromes to function correctly and efficiently. The electron transport system ("ETS") is located on the inner mitochondrial membrane. Within the inner mitochondrial membrane are also highly controlled transport proteins that transport metabolites across this membrane.

As used herein, the term "Fluid Mosaic Model" refers to a widely held conceptualization of biological membranes as a structurally and functionally asymmetric lipid-bilayer, with a larger variety of embedded proteins that aid in cross-membrane transport. The Fluid Mosaic Model is so named, because the phospholipids shift position in the membrane almost effortlessly (fluid), and because the combination of all the phospholipids, proteins, and glycoproteins present within the membrane give the cell a mosaic image from the outside. This model is based on a careful balance of thermodynamic and functional considerations. Alteration of the membrane thermodynamics affects the function of the membrane.

As used herein, the term "Membrane Dipole Potential $\Psi d$" (in contrast to the Transmembrane Potential $\Delta\Psi$) refers to the potential formed between the highly hydrated lipid heads (hydrophilic) at the membrane surface and the low polar interior of the bilayer (hydrophobic). Lipid bilayers intrinsically possess a substantial Membrane Dipole Potential $\Psi d$ arising from the structural organization of dipolar groups and molecules, primarily the ester linkages of the phospholipids and water.

$\Psi d$ does not depend upon the ions at the membrane surface and will be used herein to describe five different dipole potentials:
1) Mammalian Plasma Membrane Dipole Potential $\Psi$d-plas-mam;
2) Mammalian Mitochondrial Membrane Dipole Potential $\Psi$d-mito-mam;
3) Fungal Plasma Membrane Dipole Potential $\Psi$d-plas-fungi;
4) Fungal Mitochondrial Membrane Dipole Potential $\Psi$d-mito-fungi; and
5) Bacterial Plasma Membrane Dipole Potential $\Psi$d-plas-bact.

As used herein, the term "Trans-Membrane Potential" refers to the electrical potential difference between the aqueous phases separated by a membrane (dimensions mV) and will be given by the symbol ($\Delta\Psi$). $\Delta\Psi$ does depend upon the ions at the membrane surface and will be used herein to describe three different plasma trans-membrane potentials.
1) Mammalian Plasma Trans-Membrane Potential $\Delta\Psi$-plas-mam
2) Fungal Plasma Trans-Membrane Potential $\Delta\Psi$-plas-fungi
3) Bacterial Plasma Trans-Membrane Potential $\Delta\Psi$-plas-bact As used herein, the term "Mitochondrial Trans-Membrane Potential" refers to the electrical potential difference between the compartments separated by the mitochondrial inner membrane (dimensions mV) and will be used herein to describe two different mitochondrial trans-membrane potentials.
1) Mammalian Mitochondrial Trans-Membrane Potential $\Delta\Psi$-mito-mam
2) Fungal Mitochondrial Trans-Membrane Potential $\Delta\Psi$-mito-fungi In mitochondria, the potential energy from nutrients (e.g., glucose) is converted into active energy available for cellular metabolic processes. The energy released during successive oxidation-reduction reactions allows pumping protons ($H^+$ ions) from the mitochondrial matrix to the inter-membrane space. As a result, there is a chemiosmotic electrical potential difference at the mitochondrial membrane as the membrane is polarized ($\Delta\Psi$-mito-mam or $\Delta\Psi$-mito-fungi). $\Delta\Psi$-mito-mam and $\Delta\Psi$-mito-fungi are important parameters of mitochondrial functionality and give a direct quantitative value to the energy status (redox state) of a cell.

As used herein, the term "mammalian plasma trans-membrane potential ($\Delta\Psi$-plas-mam)" refers to the electrical potential difference in the mammalian cell plasma membrane between the aqueous phases. The mammalian plasma membrane potential is different from the bacterial and fungal $\Delta\Psi$ that are primarily generated with $H^+$ ions (protons). In the mammalian plasma membrane the major facilitator of the $\Delta\Psi$ is the electrogenic $Na^+/K^+$-ATPase pump. $\Delta\Psi$-plas-mam is generated by the additive qualities of trans-membrane $K^+$ diffusion (from the inside to the outside of the cell) and the electrogenic $Na^+/K^+$-ATPase pump. Mammalian ATP is generated in the mitochondria via the proton pump.

As used herein, the term "fungal plasma trans-membrane potential ($\Delta\Psi$-plas-fungi)" refers to the electrical potential difference in the fungal cell plasma membrane. The fungal plasma membrane potential is generated by a membrane-bound $H^+$-ATPase, a high-capacity proton pump that requires ATP to function. This $H^+$-ATPase pump is needed for both fungal growth and stable cell metabolism and maintenance. Fungal ATP is generated in the mitochondria.

As used herein, the term "bacterial plasma trans-membrane potential ($\Delta\Psi$-plas-bact)" refers to the electrical potential difference in the bacterial cell plasma membrane. The bacterial plasma membrane potential is generated by the steady-state flow (translocation) of electrons and protons ($H^+$) across the bacterial plasma membrane that occurs with normal electron transport and oxidative phosphorylation, within the bacterial plasma membrane. A common feature of all electron transport chains is the presence of a proton pump to create a transmembrane proton gradient. Although bacteria lack mitochondria, aerobic bacteria carry out oxidative phosphorylation (ATP production) by essentially the same process that occurs in eukaryotic mitochondria.

As used herein, the term "P-class ion pump" refers to a trans-membrane active transport protein assembly which contains an ATP-binding site (i.e., it needs ATP to function). During the transport process, one of the protein subunits is phosphorylated, and the transported ions are thought to move through the phosphorylated subunit. This class of ion pumps includes the $Na^+/K^+$-ATPase pump in the mammalian plasma membrane, which maintains the $Na^+$ and $K^+$ electrochemical potential ($\Delta Na^+/K^+$) and the pH gradients typical of animal cells. Another important member of the P-class ion pumps, transports protons ($H^+$ ions) out of and $K^+$ ions in to the cell.

As used herein, the term "$Na^+/K^+$ ATPase" refers to a P-class ion pump that is present in the plasma membrane of all animal cells, and couples hydrolysis of one ATP molecule to the export of three $Na^+$ ions and the import of two $K^+$ ions that maintains the $Na^+$ and $K^+$ electrochemical potential and the pH gradients typical of animal cells. The inside-negative membrane potential in fungal cells (also eukaryotic) is generated by transport of $H^+$ ions out of the cell by a different ATP powered proton pump.

As used herein, the terms "ion exchangers and ion channels" refer to transmembrane proteins that are ATP-independent systems, and aid in establishing a plasma membrane potential in mammalian cells.

As used herein, the term "Redox (shorthand for reduction/oxidation reaction)" describes the complex processes of the oxidation of, e.g., sugar in cells through a series of very complex processes involving electron transfers. Redox reactions are chemical reactions in which electrons are transferred from a donor molecule to an acceptor molecule. The term redox comes from the two concepts of reduction and oxidation, and can be explained in the simple terms:

Oxidation describes the loss of electrons by a molecule, atom or ion. Reduction describes the gain of electrons by a molecule, atom or ion.

As used herein, the term "redox state" describes the redox environment (or level of oxidative stress) of the cells being described.

As used herein, the term "steady-state plasma trans-membrane potential ($\Delta\Psi$-steady)" refers to the quantitative Plasma Membrane Potential of a mammalian, fungal or bacterial cell before irradiation in accordance with the methods and systems of the present invention that would continue into the future in the absence of such irradiation.

For example, the steady-state flow of electrons and protons across a bacterial cell membrane that occurs during normal electron transport and oxidative phosphorylation would be in a steady-state due to a constant flow of conventional redox reactions occurring across the membrane. Conversely any modification of this redox state would cause a transient-state membrane potential. $\Delta\Psi$-steady will be used herein to describe three (3) different steady-state plasma trans-membrane potentials, based on species.

1) Steady-state mammalian plasma trans-membrane potential ΔΨ-steady-mam
2) Steady-state fungal plasma trans-membrane potential ΔΨ-steady-fungi
3) Steady-state bacterial plasma trans-membrane potential ΔΨ-steady-bact As used herein, the term "Transient-state plasma membrane potential (ΔΨ-tran)" refers to the Plasma Membrane Potential of a mammalian, fungal or bacterial cell after irradiation in accordance with the methods and systems of the present invention whereby the irradiation has changed the bioenergetics of the plasma membrane. In a bacteria, ΔΨ-tran will also change the redox state of the cell, as the plasma membrane is where the ETS and cytochromes reside. ΔΨ-tran is a state that would not occur without irradiation using methods of the present invention. ΔΨ-tran will be used herein to describe three (3) different Transient-state plasma trans-membrane potentials based on species.
1) Transient-state mammalian plasma trans-membrane potential ΔΨ-tran-mam
2) Transient-state fungal plasma trans-membrane potential ΔΨ-tran-fungi
3) Transient-state bacterial plasma trans-membrane potential ΔΨ-tran-bact As used herein, the term "steady-state mitochondrial membrane potential (ΔΨ-steady-mito)" refers to the quantitative Mitochondrial Membrane Potential of mammalian or fungal mitochondria before irradiation in accordance with the methods and systems of the present invention that would continue into the future, in the absence of such irradiation.

For example, the steady-state flow of electrons and protons across mitochondrial inner membrane that occurs during normal electron transport and oxidative phosphorylation would be in a steady-state because of a constant flow of conventional redox reactions occurring across the membrane. Any modification of this redox state would cause a transient-state mitochondrial membrane potential. ΔΨ-steady-mito will be used herein to describe two (2) different steady-state mitochondrial membrane potentials based on species.
1) Steady-state mitochondrial mammalian potential ΔΨ-steady-mito-mam
2) Steady-state mitochondrial fungal potential ΔΨ-steady-mito-fungi As used herein, the term "transient-state mitochondrial membrane potential (ΔΨ-tran-mito-mam or ΔΨ-tran-mito-fungi)" refers to the membrane potential of a mammalian or fungal cell after irradiation in accordance with the methods and systems of the present invention whereby the irradiation has changed the bioenergetics of the mitochondrial inner membrane. In mammalian and fungal cells, ΔΨ-tran-mito will also change the redox state of the cell, as the inner mitochondrial membrane is where the electron transport system (ETS) and cytochromes reside. ΔΨ-tran-mito could also drastically affect (the Proton-motive force) Δp-mito-mam and Δp-mito-fungi, as these mitochondrial ($H^+$) gradients are generated in the mitochondria, to produce adequate ATP for a myriad of cellular functions. ΔΨ-tran-mito is a state that would not occur without irradiation in accordance with methods and systems of the present invention. ΔΨ-tran-mito will be used herein to describe two (2) different transient-state mitochondrial membrane potentials based on species.
1) Transient-state mitochondrial mammalian potential ΔΨ-tran-mito-mam
2) Transient-state mitochondrial fungal potential ΔΨ-tran-mito-fungi As used herein, the term "cytochrome" refers to a membrane-bound hemoprotein that contains heme groups and carries out electron transport.

As used herein, the term "electron transport system (ETS)" describes a series of membrane-associated electron carriers (cytochromes) mediating biochemical reactions, that produce (ATP), which is the energy currency of cells. In the prokaryotic cell (bacteria) this occurs in the plasma membrane. In the eukaryotic cell (fungi and mammalian cells) this occurs in the mitochondria.

As used herein, the term "pH Gradient (ΔpH)" refers to the pH difference between two bulk phases on either side of a membrane.

As used herein, the term "proton electrochemical gradient (ΔμH$^+$) (dimensions kj mol-1)" refers to the electrical and chemical properties across a membrane, particularly proton gradients, and represents a type of cellular potential energy available for work in a cell. This proton electrochemical potential difference between the two sides of a membrane that engage in active transport involving proton pumps, is at times also called a chemiosmotic potential or proton motive force. When ΔμH$^+$ is reduced by any means, it is a given that cellular anabolic pathways and resistance mechanisms in the affected cells are inhibited. This can be accomplished by combining λn and Tn to irradiate a target site alone, or can be further enhanced with the simultaneous or sequential administration of a pharmacological agent configured and arranged for delivery to the target site (i.e., the co-targeting of an anabolic pathway with (λn and Tn)+(pharmacological molecule or molecules)).

As used herein, the term "Ion Electrochemical Gradient (Δμx+)" refers to the electrical and chemical properties across a membrane caused by the concentration gradient of an ion (other than H$^+$) and represents a type of cellular potential energy available for work in a cell. In mammalian cells, the Na$^+$ ion electrochemical gradient is maintained across the plasma membrane by active transport of Na$^+$ out of the cell. This is a different gradient than the proton electrochemical potential, yet is generated from an ATP coupled pump, said ATP produced during oxidative phosphorylation from the mammalian mitochondrial proton-motive force (Δp-mito-mam). When λμx$^+$ is reduced by any means, it is a given that cellular anabolic pathways and resistance mechanisms in the affected cells are inhibited. This can be accomplished by combining λn and Tn to irradiate a target site alone, or can be further enhanced with the simultaneous or sequential administration of a pharmacological agent configured and arranged for delivery to the target site (i.e., the co-targeting of an anabolic pathway with (λn and Tn)+(pharmacological molecule or molecules)).

As used herein, the term "co-targeting of a bacterial anabolic pathway" refers to (the λn and Tn lowering of (ΔμH$^+$) and/or (Δμx$^+$) of cells at the target site to affect an anabolic pathway)+(a pharmacological molecule or molecules to affect the same bacterial anabolic pathway) and can refer to any of the following bacterial anabolic pathways that are capable of being inhibited with pharmacological molecules:

wherein the targeted anabolic pathway is peptidoglycan biosynthesis that is co-targeted by a pharmacological agent that binds at the active site of the bacterial transpeptidase enzymes (penicillin binding proteins) which cross-links peptidoglycan in the bacterial cell wall. Inhibition of these enzymes ultimately cause cell lysis and death;

wherein the targeted bacterial anabolic pathway is peptidoglycan biosynthesis that is co-targeted by a pharmacological agent that binds to acyl-D-alanyl-D-alanine groups in cell wall intermediates and hence prevents incorporation of N-acetylmuramic acid (NAM)- and N-acetylglucosamine (NAG)-peptide subunits into the peptidoglycan matrix (effectively inhibiting peptidoglycan biosynthesis by acting on transglycosylation and/or transpeptidation) thereby preventing the proper formation of peptidoglycan, in gram positive bacteria;

wherein the targeted bacterial anabolic pathway is peptidoglycan biosynthesis that is co-targeted by a pharmacological agent that binds with $C_{55}$-isoprenyl pyrophosphate and prevents pyrophosphatase from interacting with $C_{55}$-isoprenyl pyrophosphate thus reducing the amount of $C_{55}$-isoprenyl pyrophosphate that is available for carrying the building blocks peptidoglycan outside of the inner membrane;

wherein the targeted anabolic pathway is bacterial protein biosynthesis that is co-targeted by a pharmacological agent that binds to the 23 S rRNA molecule in the subunit 50 S subunit of the bacterial ribosome, causing the accumulation of peptidyl-tRNA in the cell, hence depleting the free tRNA necessary for activation of α-amino acids, and inhibiting transpeptidation by causing premature dissociation of peptidyl tRNA from the ribosome;

wherein the co-targeted pharmacological agent binds simultaneously to two domains of 23 S RNA of the 50 S bacterial ribosomal subunit, and can thereby inhibit the formation of the bacterial ribosomal subunits 50 S and 30 S (ribosomal subunit assembly)

wherein the co-targeted pharmacological agent is chlorinated to increases its lipophilicity to penetrate into bacterial cells, and binds to the 23 S portion of the 50 S subunit of bacterial ribosomes and prevents the translocation of the peptidyl-tRNA from the Aminoacyl site (A-site) to the Peptidyl site (P-site) thereby inhibiting the transpeptidase reaction, which results in an incomplete peptide being released from the ribosome;

wherein the targeted anabolic pathway is bacterial protein biosynthesis that is co-targeted by pharmacological agent that binds to the 30 S bacterial ribosomal subunit and blocks the attachment of the amino-acyl tRNA from binding to the acceptor site (A-site) of the ribosome, thereby inhibiting the codon-anticodon interaction and the elongation phase of protein synthesis;

wherein the co-targeted pharmacological agent binds more avidly to the bacterial ribosomes, and in a different orientation from the classical subclass of polyketide antimicrobials having an octahydrotetracene-2-carboxamide skeleton, so that they are active against strains of *S. aureus* with a tet(M) ribosome and tet(K) efflux genetic determinant;

wherein the targeted anabolic pathway is bacterial protein biosynthesis that is co-targeted by a pharmacological agent that binds to a specific aminoacyl-tRNA synthetase to prevent the esterification of a specific amino acid or its precursor to one of its compatible tRNA's, thus preventing formation of an aminoacyl-tRNA and hence halting the incorporation of a necessary amino acid into bacterial proteins;

wherein the targeted anabolic pathway is bacterial protein biosynthesis that is co-targeted by a pharmacological agent that inhibits bacterial protein synthesis before the initiation phase, by binding the 50 S rRNA through domain V of the 23 S rRNA, along with interacting with the 16 S rRNA of the 30 S ribosomal subunit, thus preventing binding of the initiator of protein synthesis formyl-methionine (f-Met-tRNA), and the 30 S ribosomal subunit;

wherein the targeted anabolic pathway is bacterial protein biosynthesis that is co-targeted by a pharmacological agent that interacts with the 50 S subunit of bacterial ribosomes at protein L3 in the region of the 23 S rRNA P site near the peptidyl transferase center and hence inhibits peptidyl transferase activity and peptidyl transfer, blocks P-site interactions, and prevents the normal formation of active 50 S ribosomal subunits;

wherein the targeted anabolic pathway is DNA replication and transcription that is co-targeted by a pharmacological agent that inhibits Topoisomerase II (DNA gyrase) and/or Topoisomerase IV;

wherein the targeted anabolic pathway is DNA replication and translation that is co-targeted by a pharmacological agent that inhibits DNA polymerase IIIC, the enzyme required for the replication of chromosomal DNA in gram-positive bacteria, but not present in gram-negative bacteria;

wherein the targeted anabolic pathway is DNA replication and transcription that is co-targeted by a pharmacological hybird compound that inhibits Topoisomerase II (DNA gyrase) and/or Topoisomerase IV and/or DNA polymerase IIIC;

wherein the targeted anabolic pathway is bacterial phospholipid biosynthesis that is co-targeted by a topical pharmacological agent that acts on phosphatidylethanolamine-rich cytoplasmic membranes and works well in combination with other topical synergistic agents;

wherein the targeted anabolic pathway is bacterial fatty acid biosynthesis that is co-targeted by a pharmacological agent that inhibits bacterial fatty acid biosynthesis through the selective targeting of β-ketoacyl-(acyl-carrier-protein (ACP)) synthase I/II (FabF/B), an essential enzymes in type II fatty acid synthesis;

wherein the targeted anabolic pathway is maintenance of bacterial plasma trans-membrane potential ΔΨ-plas-bact and the co-targeting pharmacological agent disrupts multiple aspects of bacterial cell membrane function on its own, by binding primarily to gram positive cytoplasmic membranes, not penetrating into the cells, and causing depolarization and loss of membrane potential that leads to inhibition of protein, DNA and RNA synthesis;

wherein the co-targeting pharmacological agent increases the permeability of the bacterial cell wall, and hence allows inorganic cations to travel through the wall in an unrestricted manner thereby destroying the ion gradient between the cytoplasm and extracellular environment;

wherein the targeted anabolic pathway is maintenance of bacterial membrane selective permeability and bacterial plasma trans-membrane potential ΔΨ-plas-bact, and the co-targeting pharmacological agent is a cationic antibacterial peptide that is selective for the negatively charged surface of bacterial membranes relative to the neutral membrane surface of eukaryotic cells and leads to prokaryotic membrane permeablization and ultimate perforation and/or disintegration of bacterial cell membranes, thereby promoting leakage of bacterial cell contents and a breakdown of the transmembrane potential;

wherein the co-targeting pharmacological agent inhibits bacteria protease Peptide Deformylase, that catalyzes the removal of formyl groups from the N-termini of newly synthesized bacterial polypeptides; and wherein the co-targeting pharmacological agent inhibits two-component regulatory systems in bacteria, such as the ability to respond to their environment through signal transduction across bacterial plasma membranes, these signal transduction processes being absent in mammalian membranes.

As used herein, the term "co-targeting of a fungal anabolic pathway" refers to (the λn and Tn lowering of ($\Delta\mu H^{+}$) and/or ($\Delta\mu x^{+}$) of cells at the target site to affect an anabolic pathway)+(a pharmacological agent to affect the same fungal anabolic pathway) and can refer to any of the following fungal anabolic pathways that are capable of being inhibited with pharmacological agents:

wherein the targeted anabolic pathway is phospholipid Biosynthesis that is co-targeted by a topical pharmacological agent that disrupts the structure of existing phospholipids, in fungal cell membranes and workswell in combination with other topical synergistic agents;

wherein targeted anabolic pathway is ergosterol biosynthesis that is co-targeted by a pharmacological agent that inhibits ergosterol biosynthesis at the C-14 demethylation stage, part of the three-step oxidative reaction catalyzed by the cytochrome P-450 enzyme 14-a-sterol demethylase, resulting in ergosterol depletion and accumulation of lanosterol and other 14-methylated sterols that interfere with the 'bulk' functions of ergosterol as a membrane component, via disruption of the structure of the plasma membrane;

wherein targeted anabolic pathway is ergosterol biosynthesis that is co-targeted with a pharmacological agent inhibits the enzyme squalene epoxidase, that in turn inhibits ergosterol biosynthesis in fungal cells that causes the fungal cell membranes to have increased permeability;

wherein targeted anabolic pathway is ergosterol biosynthesis that is co-targeted with a pharmacological agent inhibits two enzymes in the ergosterol biosynthetic pathway at separate and distinct points, d14-reductase and d7, d8-isomerase;

wherein targeted anabolic pathway is fungal cell wall biosynthesis that is co-targeted with a pharmacological agent that inhibits the enzyme $(1,3)\beta$-D-Glucan synthase, that in turn inhibits $\beta$-D-glucan synthesis in the fungal cell wall;

wherein the wherein targeted anabolic pathway is fungal sterol biosynthesis that is co-targeted with a pharmacological agent binds with sterols in fungal cell membranes, the principal sterol that the co-targeting pharmacological agent binds being ergosterol, that effectively changes the transition temperature of the cell membrane and causes pores to form in the membrane resulting in the formation of detrimental ion channels in fungal cell membranes;

wherein the co-targeted pharmacological agent is formulated for delivery in lipids, liposomes, lipid complexes and/or colloidal dispersions to prevent toxicity from the agent;

wherein the wherein targeted anabolic pathway is protein synthesis is co-targeted with a pharmacological agent that 5-FC is taken up into fungal cells by a cytosine permease, deaminated to 5-fluorouracil (5-FU), converted to the nucleoside triphosphate, and incorporated into RNA where it causes miscoding;

wherein the wherein targeted anabolic pathway is fungal protein synthesis that is co-targeted with a pharmacological agent that inhibits fungal elongation factor EF-2, which is functionally distinct from its mammalian counterpart and/or fungal elongation factor 3 (EF-3) which is absent from mammalian cells;

wherein the wherein targeted anabolic pathway is fungal Chitin bio-synthesis (the $\beta$-(1,4)-linked homopolymer of N-acetyl-D-glucosamine), that is co-targeted with a pharmacological agent that inhibits fungal chitin biosynthesis by inhibiting the action of one or more of the enzymes chitin synthase 2, an enzyme necessary for primary septum formation and cell division in fungi;

wherein the wherein the co-targeted pharmacological agent inhibits the action of the enzyme chitin synthase 3, an enzyme necessary for the synthesis of chitin during bud emergence and growth, mating, and spore formation;

wherein the co-targeting pharmacological agent chelates polyvalent cations ($Fe^{+3}$ or $Al^{+3}$) resulting in the inhibition of the metal-dependent enzymes that are responsible for mitochondrial electron transport and cellular energy production, that also leads to inhibition of normal degradation of peroxides within the fungal cell; and wherein the co-targeting pharmacological agent inhibits two-component regulatory systems in fungi, such as the ability to respond to their environment through signal transduction across fungal plasma membranes.

As used herein, the term "co-targeting of a cancer anabolic pathway" refers to (the $\lambda$n and Tn lowering of $(\Delta\mu H^+)$ and/or $(\Delta\mu x+)$ of cells at the target site to affect an anabolic pathway)+(a pharmacological agent to affect the same cancer anabolic pathway to a greater extent than the non cancerous cells) and can refer to any of the following cancer anabolic pathways that are capable of being inhibited with pharmacological agents:

wherein the targeted anabolic pathway is DNA replication that is co-targeted by a pharmacological agent that inhibits DNA replication by cross-linking guanine nucleobases in DNA double-helix strands making the strands unable to uncoil and separate, which is necessary in DNA replication;

wherein the targeted anabolic pathway is DNA replication that is co-targeted by a pharmacological agent that can react with two different 7-N-guanine residues in the same strand of DNA or different strands of DNA;

wherein the targeted anabolic pathway is DNA replication that is co-targeted by a pharmacological agent that inhibits DNA replication and cell division by acting as an antimetabolite;

wherein the targeted anabolic pathway is cell division that is co-targeted by a pharmacological agent that inhibits cell division by preventing microtubule function;

wherein the targeted anabolic pathway is DNA replication that is co-targeted by a pharmacological agent that inhibits DNA replication and cell division by preventing the cell from entering the G1 phase (the start of DNA replication) and the replication of DNA (the S phase);

wherein the targeted anabolic pathway is cell division that is co-targeted by a pharmacological agent that enhances the stability of microtubules, preventing the separation of chromosomes during anaphase; and wherein the targeted anabolic pathway is DNA replication that is co-targeted by a pharmacological agent that inhibits DNA replication and cell division by Inhibition of type I or type II topoisomerases, that will interferes with both transcription and replication of DNA by upsetting proper DNA supercoiling.

As used herein, the term "proton-motive force ($\Delta p$)" refers to the storing of energy (acting like a kind of battery), as a combination of a proton and voltage gradient across a membrane. The two components of $\Delta p$ are $\Delta\Psi$ (the transmembrane potential) and $\Delta pH$ (the chemical gradient of $H^+$). Stated another way, $\Delta p$ consists of the $H^+$ transmembrane potential $\Delta\Psi$ (negative (acidic) outside) and a transmembrane pH gradient $\Delta pH$ (alkaline inside). This potential energy stored in the form of an electrochemical gradient, is generated by the pumping of hydrogen ions across biological membranes (mitochondrial inner membranes or bacterial and fungal plasma membranes) during chemiosmosis. The $\Delta p$ can be used for chemical, osmotic, or mechanical work in the cells. The proton gradient is generally used in oxidative phosphorylation to drive ATP synthesis and can be used to drive efflux pumps in bacteria, fungi, or mammalian cells including cancerous cells. $\Delta p$ will be used herein to describe four (4) different proton motive forces in membranes, based on species, and is mathematically defined as ($\Delta P=\Delta\Psi+\Delta pH$).

1) Mammalian Mitochondrial Proton-motive force (Δp-mito-mam)
2) Fungal Mitochondrial Proton-motive force (Δp-mito-Fungi)
3) Fungal Plasma Membrane Proton-motive force (Δp-plas-Fungi)
4) Bacterial Plasma Membrane Proton-motive force (Δp-plas-Bact)

As used herein, the term of "Mammalian Mitochondrial Proton-motive force (Δp-mito-mam)" refers to the potential energy stored in the form of an ($H^+$) electrochemical gradient across a mammalian mitochondrial inner membrane. Δp-mito-mam is used in oxidative phosphorylation to drive ATP synthesis in the mammalian mitochondria.

As used herein, the term of "Fungal Mitochondrial Proton-motive force (Δp-mito-Fungi)" refers to the potential energy stored in the form of an ($H^+$) electrochemical gradient across a fungal mitochondrial inner membrane. Δp-mito-Fungi is used in oxidative phosphorylation to drive ATP synthesis in the fungal mitochondria.

As used herein, the term "Fungal Plasma Membrane Proton-motive force (Δp-plas-Fungi)" refers to the potential energy stored in the form of an ($H^+$) electrochemical gradient, across a fungal plasma membrane and is generated by the pumping of hydrogen ions across the plasma membrane by a membrane-bound $H^+$-ATPase. This plasma membrane-bound $H^+$-ATPase is a high-capacity proton pump, that requires ATP to function. The ATP for this $H^+$-ATPase is generated from the Δp-mito-Fungi. Δp-plas-Fungi can be used to drive efflux pumps in fungal cells.

As used herein, the term "Bacterial Plasma Membrane Proton-motive force (Δp-plas-Bact)" refers to the potential energy stored in the form of an electrochemical gradient ($H^+$), across a bacterial plasma membrane, and is generated by the pumping of hydrogen ions across the plasma membrane during chemiosmosis. Δp-plas-Bact is used in oxidative phosphorylation to drive ATP synthesis in the bacterial plasma membrane and can be used to drive efflux pumps in bacterial cells.

As used herein, the term "anabolic pathway" refers to a cellular metabolic pathway that constructs molecules from smaller units. These reactions require energy. Many anabolic pathways and processes are powered by adenosine triphosphate (ATP). These processes can involve the synthesis of simple molecules such as single amino acids and complex molecules such as peptidoglycan, proteins, enzymes, ribosomes, cellular organelles, nucleic acids, DNA, RNA, glucans, chitin, simple fatty acids, complex fatty acids, cholesterols, sterols, and ergosterol.

As used herein, the term "energy transduction" refers to proton transfer through the respiratory complexes embedded in a membrane, utilizing electron transfer reactions to pump protons across the membrane and create an electrochemical potential also known as the proton electrochemical gradient.

As used herein the term "energy transformation" in cells refers to chemical bonds being constantly broken and created, to make the exchange and conversion of energy possible. It is generally stated that that transformation of energy from a more to a less concentrated form is the driving force of all biological or chemical processes that are responsible for the respiration of a cells.

As used herein the term "uncoupler" refers to a molecule or device that causes the separation of the energy stored in the proton electrochemical gradient (ΔμH$^+$) of membranes from the synthesis of ATP.

As used herein the term "uncoupling" refers to the use of an uncoupler (a molecule or device) to cause the separation of the energy stored in the proton electrochemical gradient (ΔμH$^+$) of membranes from the synthesis of ATP.

As used herein the term "adenosine 5'-triphosphate (ATP)" refers to a multi-functional nucleotide that acts as "molecular currency" of intracellular energy transfer. ATP transports chemical energy within cells for metabolism and is produced as an energy source during the process of cellular respiration. ATP is consumed by many enzymes and a broad array of cellular processes including biosynthetic reactions, efflux pump function, and anabolic cell growth and division.

As used herein the term "adenosine diphosphate (ADP)" is the product of ATP dephosphorylation by ATPases. ADP is converted back to ATP by ATP synthesis. It is understood that in aerobic respiring cells, under physiological conditions, ATP synthase creates ATP while using the proton-motive force Δp created by the ETS as a source of energy. The overall process of creating energy in this fashion is termed oxidative phosphorylation. The overall reaction sequence of oxidative phosphorylation is: ADP+$P_i$→ATP. The underlying force driving biological reactions is the Gibbs free energy of the reactants and products. The Gibbs free energy is the energy available ("free") to do work, and the term Gibbs free energy change (ΔG) refers to a change in the free energy available in the membrane to do work. This free energy is a function of enthalpy (ΔH), entropy (ΔS), and temperature. (Enthalpy and entropy are discussed below.)

As used herein, the term "phosphorylation potential (ΔGp)" refers to the ΔG for ATP synthesis at any given set of ATP, ADP and Pi concentrations (dimensions: kj mol$^{-1}$).

As used herein the term "CCCP" refers to carbonyl cyanide m-chlorophenylhydrazone, a highly toxic ionophore and uncoupler of the respiratory chain. CCCP increases the conductance of protons through membranes and acts as a classical uncoupler by uncoupling ATP synthesis from the ΔμH$^+$ and dissipating both the ΔΨ and ΔpH.

As used herein the term "depolarization" (de-energization) refers to a decrease in the absolute value of a cell's plasma or mitochondrial membrane potential ΔΨ. It is a given that depolarization of any bacterial plasma membrane will lead to a loss of ATP and increased free radical formation. It is also a given that mitochondrial depolarization of any eukaryotic cell will lead to a loss of ATP and increased free radical formation.

As used herein, the term "enthalpy change (ΔH)" refers to a change in the enthalpy or heat content of a membrane system, and is a quotient or description of the thermodynamic potential of the membrane system.

As used herein, the term "entropy change (ΔS)" refers to a change in the entropy of a membrane system to that of a more disordered state at a molecular level.

The term "redox stress", refers to cellular conditions which differ from the standard reduction/oxidation potential ("redox") state of the cell. Redox stress includes increased levels of ROS, decreased levels of glutathione and any other circumstances that alter the redox potential of the cell.

As used herein, the term "Reactive Oxygen Species", refers to one of the following categories:
a) The Superoxide ion radical ($O_2^-$)
b) Hydrogen Peroxide (non-radical) ($H_2O_2$)
c) Hydroxyl radical (*OH)
d) Hydroxy ion (OH$^-$)
These ROS generally occur through the reaction chain:

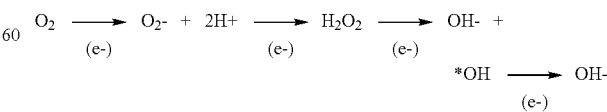

As used herein, the term "singlet oxygen" refers to ("1$O_2$") and is formed via an interaction with triplet-excited molecules. Singlet oxygen is a non-radical species with its electrons in anti-parallel spins. Because singlet oxygen $1O_2$ does not have spin restriction of its electrons, it has a very high oxidizing power and is easily able to attack membranes (e.g., via polyunsaturated fatty acids, or PUFAs) amino acid residues, protein and DNA.

As used herein, the term "energy stress" refers to conditions which alter ATP levels in the cell. This could be changes in electron transport and exposure to uncoupling agents or $\Delta\Psi$ altering radiation in mitochondrial and/or plasma membranes.

As used herein, the term "NIMELS effect" refers to the modification of the bioenergetic "state" of irradiated cells at the level of the cell's plasma and mitochondrial membranes from $\Delta\Psi$-steady to $\Delta\Psi$-trans with the present invention. Specifically, the NIMELS effect can weaken cellular anabolic pathways or antimicrobial and/or cancer resistance mechanisms that make use of the proton motive force or the chemiosmotic potential for their energy needs.

As used herein, the term "periplasmic space or periplasm" refers to the space between the plasma membrane and the outer membrane in gram-negative bacteria and the space between the plasma membrane and the cell wall in gram-positive bacteria and fungi such as the *Candida* and *Trichophyton* species. This periplasmic space is involved in various biochemical pathways including nutrient acquisition, synthesis of peptidoglycan, electron transport, and alteration of substances toxic to the cell. In gram-positive bacteria like MRSA, the periplasmic space is of significant clinical importance as it is where β-lactamase enzymes inactivate penicillin based antibiotics.

As used herein, the term "efflux pump" refers to an active transport protein assembly which exports molecules from the cytoplasm or periplasm of a cell (such as antibiotics, antifungals, or poisons) for their removal from the cells to the external environment in an energy dependent fashion.

As used herein, the term "efflux pump inhibitor" refers to a compound or electromagnetic radiation delivery system and method which interferes with the ability of an efflux pump to export molecules from a cell. In particular, the efflux pump inhibitor of this invention is a form of electromagnetic radiation that will interfere with a pump's ability to excrete therapeutic antibiotics, anti-fungal agents, antineoplastic agents and poisons from cells via a modification of the $\Delta\Psi$-steady-mam, $\Delta\Psi$-steady-fungi or, $\Delta\Psi$-steady-bact.

By a cell that "utilizes an efflux pump resistance mechanism," it is meant that the bacterial or fungal or cancer cell exports anti-bacterial and/or anti-fungal and/or antineoplastic agents from their cytoplasm or periplasm to the external environment of the cell and thereby reduce the concentration of these agents in the cell to a concentration below what is necessary to inhibit the growth and/or proliferation of the cells.

In the context of cell growth, the term "inhibit" means that the rate of growth and/or proliferation of population of cells is decreased, and if possible, stopped.

In protein chemistry the primary structure refers to the linear arrangement of amino acids; the secondary structure refers to whether the linear amino acid structure forms a helical or β-pleated sheet structure; tertiary structure of a protein or any other macromolecule is its three-dimensional structure, or stated another way, its spatial organization (including conformation) of the entire single chain molecule; the quaternary structure is the arrangement of multiple tertiary structured protein molecules in a multi-subunit complex.

As used herein, the term "protein stress", refers to thermodynamic modification in the tertiary and quaternary structure of proteins, including enzymes and other proteins that participate in membrane transport. The term includes, but is not limited to, denaturation of proteins, misfolding of proteins, cross-linking of proteins, both oxygen-dependent and independent oxidation of inter- and intra-chain bonds, such as disulfide bonds, oxidation of individual amino acids, and the like.

The term "pH stress", refers to modification of the intracellular pH, i.e., a decrease intracellular pH below about 6.0 or an increase intracellular pH above about 7.5. pH. This may be caused, for example, by exposure of the cell to the invention described herein, and altering cell membrane components or causing changes in the steady-state membrane potential potential $\Delta\Psi$-steady.

As used herein, the term "anti-fungal molecule" refers to a chemical or compound that is fungicidal or fungistatic. Of principle efficacy is the present invention's ability to potentiate anti-fungal molecules by inhibiting anabolic reactions and/or efflux pump activity in resistant fungal strains, or inhibiting other resistance mechanisms that require the proton motive force or chemiosmotic potential for energy.

As used herein, the term "anti-bacterial molecule (or agent)" refers to a chemical or compound that is bacteriacidal or bacteriastatic. Another principal efficacy resides in the present invention's ability to potentiate anti-bacterial molecules by inhibiting efflux pump activity in resistant bacterial strains, or inhibiting anabolic reactions and/or resistance mechanisms that require the proton motive force or chemiosmotic potential for energy.

As used herein, a "sub-inhibitory concentration" of an antibacterial or anti-fungal molecule refers to a concentration that is less than that required to inhibit a majority of the target cells in the population. (In one aspect, target cells are those cells that are targeted for treatment including, but not limited to, bacterial, fungi, and cancer cells.) Generally, a sub-inhibitory concentration refers to a concentration that is less than the Minimum Inhibitory Concentration (MIC), which is defined, unless specifically stated to be otherwise, as the concentration required to produce at least 10% reduction in the growth or proliferation of target cells.

As used herein, the term "Minimal Inhibitory Concentration" or MIC is defined as the lowest effective or therapeutic concentration that results in inhibition of growth of the microorganism.

As used herein, the term "therapeutically effective amount" of a pharmaceutical agent or molecule (e.g., anti-bacterial or anti-fungal agent) refers to a concentration of an agent that, together with NIMELS, will partially or completely relieve one or more of the symptoms caused by the target (pathogenic) cells. In particular, a therapeutically effective amount refers to that amount of an agent with NIMELS that: (1) reduces, if not eliminates, the population of target cells in the patient's body, (2) inhibits (i.e., slows, if not stops) proliferation of the target cells in the patients body, (3) inhibits (i.e., slows, if not stops) spread of the infection (4) relieves (if not, eliminates) symptoms associated with the infection.

As used herein, the term "Interaction coefficient" is defined as a numerical representation of the magnitude of the bacteriastatic/bacteriacidal and/or fungistatic/fungicidal interaction between the NIMELS laser and/or the antimicrobial molecule, with the target cells.

Thermodynamics of Energy Transduction in Biological Membranes

The present invention is directed to perturbing cell membrane biological thermodynamics (bioenergetics) and the consequent diminished capacity of the irradiated cells to adequately undergo normal energy transduction and energy transformation.

The methods and systems of the present invention optically alter and modify Ψd-plas-mam, Ψd-mito-mam, Ψd-plas-fungi, Ψd-mito-fungi and Ψd-plas-bact to set in motion further alterations of $\Delta\Psi$ and $\Delta p$ in the same membranes. This is caused by the targeted near infrared irradiation of the C—H covalent bonds in the long chain fatty acids of lipid bilayers, causing a variation in the dipole potential Ψd.

Figure 3:
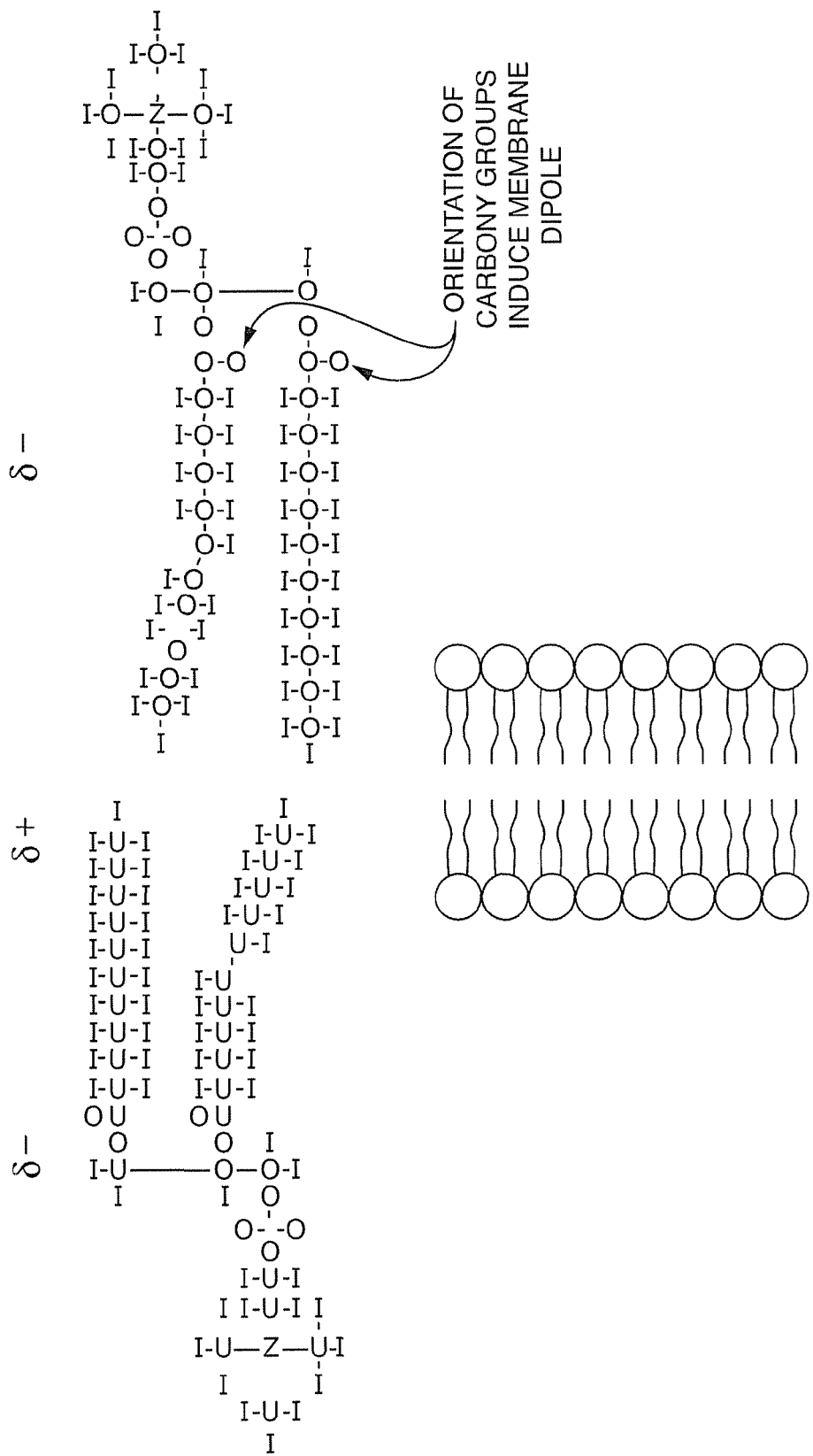
FIG. 3 shows dipole effects in phospholipid bilayer membranes ($\Psi$d)
Figure 4A:
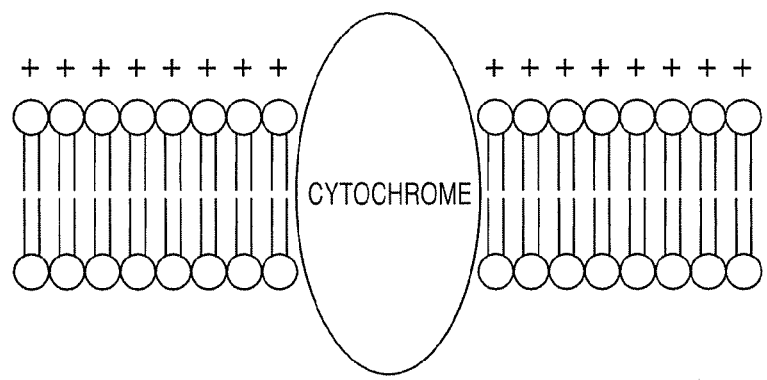
FIG. 4A shows a phospholipid bilayer in bacterial plasma membrane, mammalian mitochondrial membrane, or fugal mitochondrial membrane with a steady-state trans-membrane potential prior to NIMELS irradiation.

To aid with an understanding of the process of this bioenergetic modification, the following description of the application of thermodynamics to membrane bioenergetics and energy transduction in biological membranes is presented. To begin, membranes (lipid bilayers, see, FIG. 1) possess a significant dipole potential Ψd arising from the structural association of dipolar groups and molecules, primarily the ester linkages of the phospholipids (FIG. 2) and water. These dipolar groups are oriented such that the hydrocarbon phase is positive with respect to the outer membrane regions (FIG. 3). The degree of the dipole potential is usually large, typically several hundreds of millivolts. The second major potential, a separation of charge across the membrane, gives rise to the trans-membrane potential $\Delta\Psi$. The trans-membrane potential is defined as the electric potential difference between the bulk aqueous phases at the two sides of the membrane and results from the selective transport of charged molecules across the membrane. As a rule, the potential at the cytoplasm side of cell membranes is negative relative to the extracellular physiological solution (FIG. 4A).

The dipole potential Ψd constitutes a large and functionally important part of the electrostatic potential of all plasma and mitochondrial membranes. Ψd modifies the electric field inside the membrane, producing a virtual positive charge in the apolar bilayer center. As a result of this "positive charge", lipid membranes exhibit a substantial (e.g., up to six orders of magnitude) difference in the penetration rates between positively and negatively charged hydrophobic ions. Ψd also plays an important role in the membrane permeability for lipophilic ions.

Figure 4B:
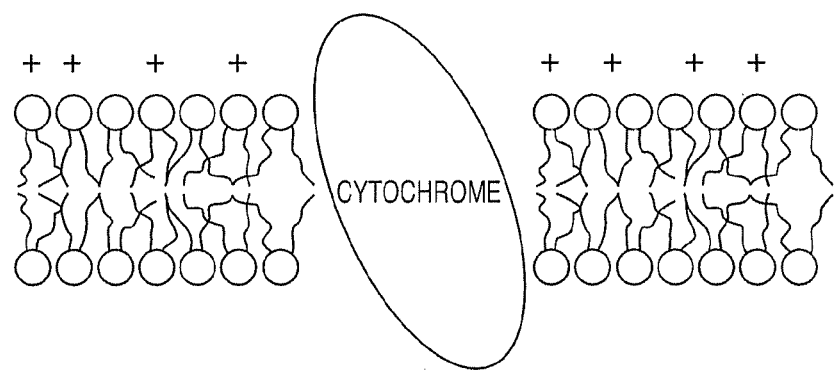
FIG. 4B shows a transient-state plasma membrane potential in bacterial plasma membrane, mammalian mitochondrial membrane, or fugal mitochondrial membrane after NIMELS irradiation.
Figure 5:
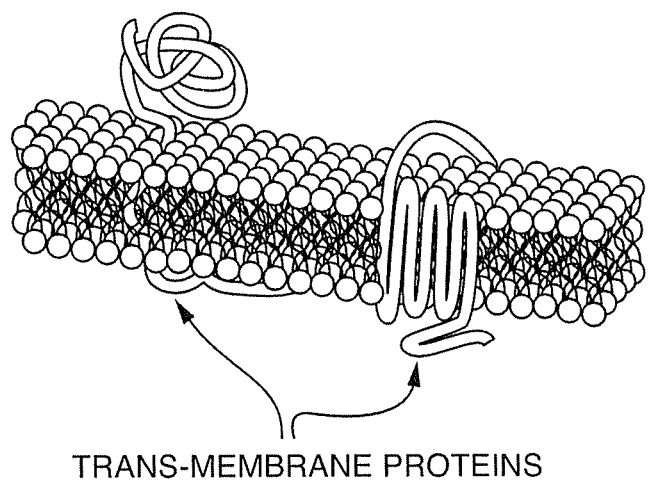
FIG. 5 shows a phospholipid bilayer with trans-membrane proteins embedded therein.

Numerous cellular processes, such as binding and insertion of proteins (enzymes), lateral diffusion of proteins, ligand-receptor recognition, and certain steps in membrane fusion to endogenous and exogenous molecules, critically depend on the physical properties Ψd of the membrane bilayer. Studies in model membrane systems have illustrated the ability of mono- and multivalent ions to cause isothermal phase transitions in pure lipids, different phase separations, and a distinct clustering of individual components in mixtures. In membranes, changes such as these can exert physical influences on the conformational dynamics of membrane-embedded proteins and cytochromes (FIG. 4B), and more specifically, on proteins that go through large conformational rearrangements in their transmembrane domains during their operating cycles (FIG. 5). Most importantly, changes in Ψd is believed to modulate membrane enzyme activities.

Energy Transduction

The energy transduction in biological membranes generally involves three interrelated mechanisms:

1) The transduction of redox energy to "free energy" stored in a trans-membrane ionic electrochemical potential also called the membrane proton electrochemical gradient $\alpha\mu H^+$. This proton electrochemical potential difference between the two sides of a membrane that engage in active transport involving proton pumps is at times also called a chemiosmotic potential or proton motive force.

2) In mammalian cells, the ($Na^+$) ion electrochemical gradient $\Delta\mu x^+$ is maintained across the plasma membrane by active transport of ($Na^+$) out of the cell. This is a different gradient than the proton electrochemical potential, yet is generated from a (pump) via the ATP produced during oxidative phosphorylation from the Mammalian Mitochondrial Proton-motive force $\Delta p$-mito-mam.

3) The use of this "free energy" to create ATP (energy transformation) to impel active transport across membranes with the concomitant buildup of required solutes and metabolites in the cell is termed the phosphorylation potential $\Delta Gp$. In other words, $\Delta Gp$ is the $\Delta G$ for ATP synthesis at any given set of ATP, ADP and $P_i$ concentrations.

Steady-State Trans-Membrane Potential ($\Delta\Psi$-Steady)

The state of a membrane "system" is in equilibrium when the values of its chemical potential gradient $\Delta\mu H^+$ and E (energy) are temporally independent and there is no flux of energy across the margins of the system. If the membrane system variables of $\Delta\mu H^+$ and E are constant, but there is a net flux of energy moving across the system, then this membrane system is in a steady-state and is temporally dependent.

It is this temporally dependent steady-state trans-membrane and/or mitochondrial potential ($\Delta\Psi$-steady) of a cell (a respiring, growing and dividing cell) that is of focus. This "steady-state" of the flow of electrons and protons, or $Na^+/K^+$ ions across a mitochondrial or plasma membrane during normal electron transport and oxidative phosphorylation, would most likely continue into the future, if unimpeded by an endogenous or exogenous event. Any exogenous modification of the membrane thermodynamics, would bring about a transient-state trans-membrane and/or mitochondrial potential $\Delta\Psi$-trans, and this change from $\Delta\Psi$-steady to $\Delta\Psi$-trans is an object of the present invention.

Mathematical relationships between the state variables $\Delta\Psi$-steady and $\Delta\Psi$-trans are called equations of state. In thermodynamics, a state function (state quantity), is a property or a system that depends only on the current state of the system. It does not depend on the way in which the system attained its particular state. The present invention facilitates a transition of state in a trans-membrane and/or mitochondrial potential $\Delta\Psi$, in a temporally dependent manner, to move the bioenergetics of a membrane from a thermodynamic steady-state condition $\Delta\Psi$-steady to one of energy stress and/or redox stress in a transition state $\Delta\Psi$-trans.

This can occur in $\Delta\Psi$-steady-mam, $\Delta\Psi$-steady-fungi, $\Delta\Psi$-steady-Bact-$\Delta\Psi$-steady-mito-mam and $\Delta\Psi$-steady-mito-fungi. Not wishing to be bound by theory, it is believed that this transition is caused by the targeted near infrared irradiation of the C—H covalent bonds in the long chain fatty acids of lipid bilayers (with 930 nm wavelength), causing a variation in the dipole potential Ψd, and the targeted near infrared irradiation of cytochrome chains (with λ of 870 nm), that will concurrently alter $\Delta\Psi$-steady and the redox potential of the membranes.

The First Law of Thermodynamics and Membranes

An elemental aspect of the First Law of Thermodynamics (which holds true for membrane systems) is that the energy of an insulated system is conserved and that heat and work are both considered as equivalent forms of energy. Hence, the energy level of a membrane system (Ψd and $\Delta\Psi$) can be altered by an increase or decrease of mechanical work exerted by a force or pressure acting, respectively, over a given distance or within an element of volume; and/or non-destructive heat transmitted through a temperature gradient in the membrane.

This law (the law of conservation of energy), posits that the total energy of a system insulated from its surroundings does not change. Thus, addition of any amounts of (energy) heat and work to a system must be reflected in a change of the energy of the system.

Absorption of Infrared Radiation

The individual photons of infrared radiation do not contain sufficient energy (e.g., as measured in electron-volts) to induce electronic transitions (in molecules) as is seen with photons of ultraviolet radiation. Because of this, absorption of infrared radiation is limited to compounds with small energy differences in the possible vibrational and rotational states of the molecular bonds.

By definition, for a membrane bilayer to absorb infrared radiation, the vibrations or rotations within the lipid bilayer's molecular bonds that absorb the infrared photons, must cause a net change in the dipole potential of the membrane. If the frequency (wavelength) of the infrared radiation matches the vibrational frequency of the absorbing molecule (i.e., C—H covalent bonds in long chain fatty acids) then radiation will be absorbed causing a change in $\Psi d$. This can happen in $\Psi d$-plas-mam, $\Psi d$-mito-mam, $\Psi d$-plas-fungi, $\Psi d$-mito-fungi and $\Psi d$-plas-bact. In other words, there can be a direct and targeted change in the enthalpy and entropy ($\Delta H$ and $\Delta S$) of all cellular lipid bilayers with the methods and systems described herein.

The present invention is based upon a combination of insights that have been introduced above and are derived in part from empirical data, which include the following:

It has been appreciated that the unique, single wavelengths (870 nm and 930 nm) are capable of killing bacterial cells (prokaryotes) such as *E. coli* and (eukaryotes) such as Chinese Hela Ovary hampster cells (CHO), as a result of the generation and interaction of ROS and toxic singlet oxygen reaction. See, e.g., U.S. application Ser. No. 10/649,910 filed 26 Aug. 2003 and U.S. application Ser. No. 10/776,106 filed 11 Feb. 2004, the entire teachings of which are incorporated herein by reference.

With such NIMEL systems, it has been established that instead of avoiding the individual 870 nm and 930 nm wavelengths, the laser system and process of the present invention (NIMEL system) combine the wavelengths at 5 log less power density than is typically found in a confocal laser microscope such as that used in optical traps (~to 500,000 w/cm² less power) to advantageously exploit the use of such wavelengths for therapeutic laser systems.

This is done for the expressed purpose of alteration, manipulation and depolarization of the $\Delta\Psi$-steady-mam, $\Delta\Psi$-steady-fungi, $\Delta\Psi$-steady-Bact, $\Delta\Psi$-steady-mito-mam and $\Delta\Psi$-steady-mito-fungi of all cells within the irradiation field. This is accomplished in the present invention by the targeted near infrared irradiation of the C—H covalent bonds in the long chain fatty acids of lipid bilayers (with 930 nm energy), resulting in a variation in the dipole potentials $\Psi d$-plas-mam, $\Psi d$-mito-mam, $\Psi d$-plas-fungi, $\Psi d$-mito-fungi and $\Psi d$-plas-bact of all biological membranes within the irradiation field. Secondly, the near infrared irradiation of cytochrome chains (with 870 nm), will additionally alter $\Delta\Psi$-steady and the redox potential of the membranes that have cytochromes (i.e., bacterial plasma membranes, and fungal and mammalian mitochondria).

Serving as direct chromophores (cytochromes and C—H bonds in long chain fatty acids), there will be a direct enthalpy and entropy change in the molecular dynamics of membrane lipids and cytochromes for all cellular lipid bilayers in the irradiation path of the present invention. This will alter each membrane dipole potential $\Psi d$, and concurrently alter the absolute value of the membrane potential $\Delta\Psi$, of all membranes in the irradiated cells.

These changes occur through significantly increased molecular motions (viz. $\Delta S$) of the lipids and metallo-protein reaction centers of the cytochromes, as they absorb energy from the NIMEL system in a linear one-photon process. As even a small thermodynamic shift in either the lipid bilayer and/or the cytochromes would be enough to change the dipole potential $\Psi d$, the molecular shape (and hence the enzymatic reactivity) of an attached electron transport protein, or trans-membrane protein would be rendered less functional. This will directly affect and modify the $\Delta\Psi$ in all membranes in the irradiated cells.

The NIMELS effect occurs in accordance with methods and systems described herein, importantly, without thermal or ablative mechanical damage to the cell membranes. This combined and targeted low dose approach is a distinct variation and improvement from existing methods that would otherwise cause actual mechanical damage to all membranes within the path of a beam of energy.

Membrane Entropy and the Second Law of Thermodynamics

The conversion of heat into other forms of energy is never perfect, and (according to the Second Law of Thermodynamics) must always be accompanied by an increase in entropy. Entropy (in a membrane) is a state function whose change in a reaction describes the direction of a reaction due to changes in (energy) heat input or output and the associated molecular rearrangements.

Even though heat and mechanical energy are equivalent in their fundamental nature (as forms of energy), there are limitations on the ability to convert heat energy into work. i.e., too much heat can permanently damage the membrane architecture and prevent work or beneficial energy changes in either direction.

Figure 6:
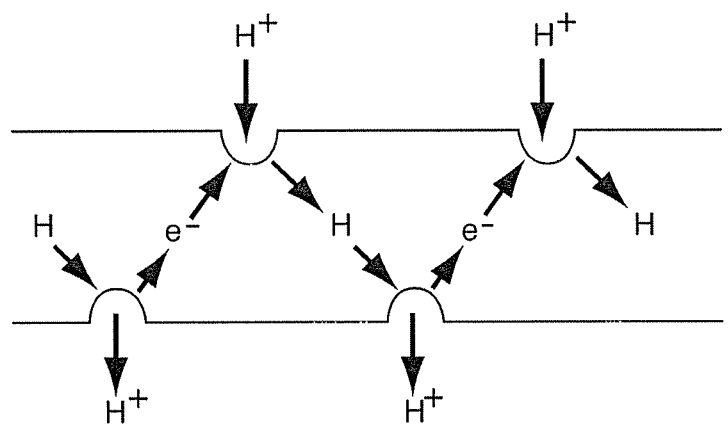
FIG. 6 shows a general depiction of electron transport and proton pump.
Figure 7:
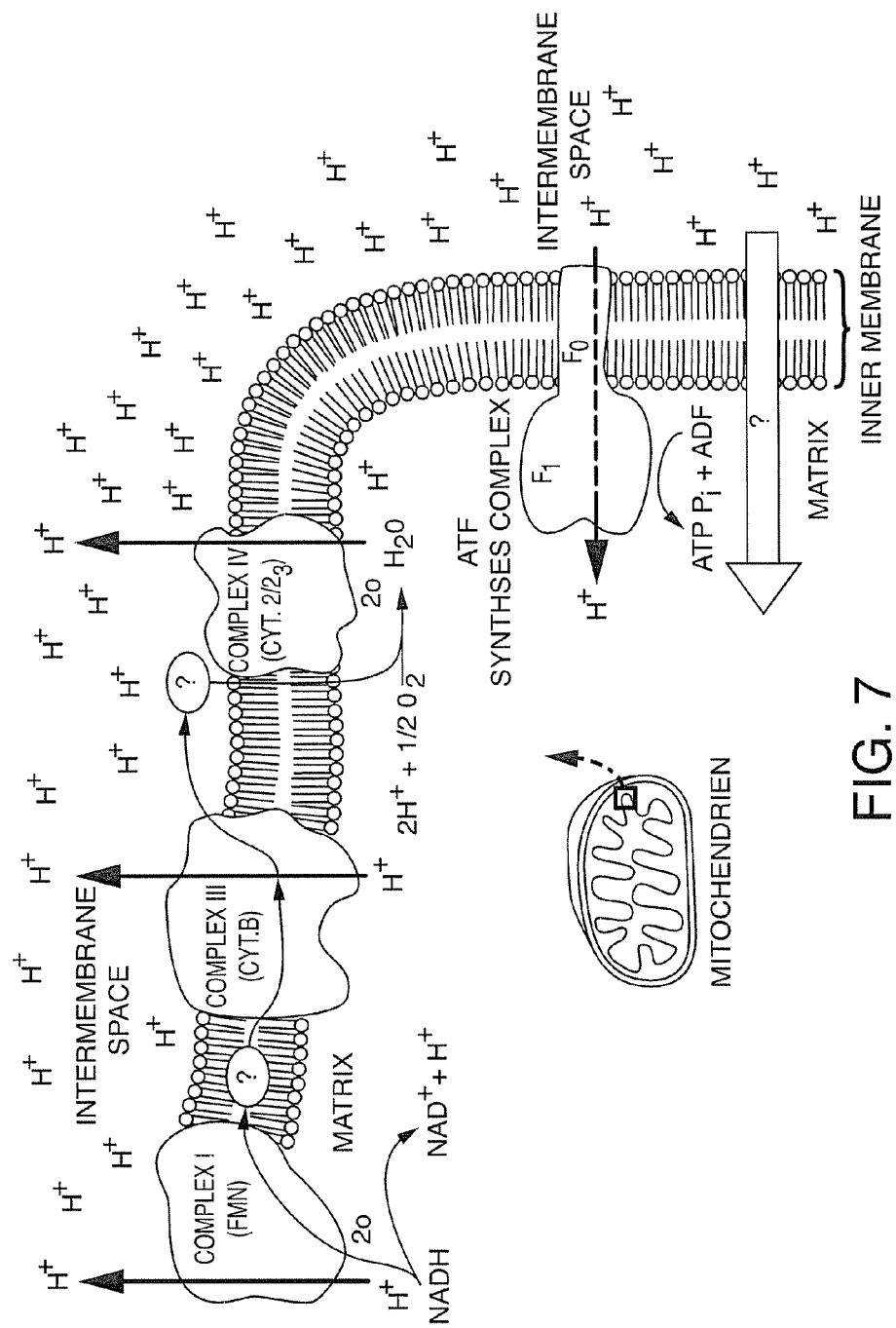
FIG. 7 shows a general view of mitochondrial membrane in fungi and mammalian cells the corresponding ΔΨ-mito-fungi or ΔΨ-mito-mam.

The NIMELS effect will modify the entropy "state" of irradiated cells at the level of the lipid bilayer in a temporally dependent manner. This increase in entropy will alter the $\Psi d$ of all irradiated membranes (mitochondrial and plasma) and hence, thermodynamically alter the "steady-state" flow of electrons and protons across a cell membrane (FIGS. 6 and 7). This will in turn change the steady-state trans-membrane potential $\Delta\Psi$-steady to a transient-state membrane potential ($\Delta\Psi$-tran). This phenomenon will occur in:

1) Mammalian Plasma Trans-membrane Potential $\Delta\Psi$-plas-mam;
2) Fungal Plasma Trans-membrane Potential $\Delta\Psi$-plas-fungi;
3) Bacterial Plasma Trans-membrane Potential $\Delta\Psi$-plas-bact;
4) Mammalian Mitochondrial Trans-membrane Potential $\Delta\Psi$-mito-mam; and
5) Fungal Mitochondrial Trans-membrane Potential $\Delta\Psi$-mito-fungi.

This is a direct result of the targeted enthalpy change at the level of the C—H bonds of the long chain fatty acids in the fluid mosaic membrane, causing a measure of dynamic disorder (in the membrane) which can alter the membranes corporeal properties. This fluid mosaic increases in entropy and can disrupt the tertiary and quaternary properties of electron transport proteins, cause redox stress, energy stress and subsequent generation of ROS, that will further damage membranes and additionally alter the bioenergetics.

Since a prime function of the electron transport system of respiring cells is to transduce energy under steady-state conditions, techniques according to the present invention are utilized to temporarily, mechano-optically uncouple many of the relevant thermodynamic interactions on that transduction process. This can be done with the express intent of altering the absolute quantitative value of the proton electrochemical gradient $\Delta\mu H^+$ and proton-motive force and $\Delta p$ of the membranes. This phenomenon can occur, inter alia, in:
1) Mammalian Mitochondrial Proton-motive force ($\Delta$p-mito-mam);
2) Fungal Mitochondrial Proton-motive force ($\Delta$p-mito-Fungi);
3) Fungal Plasma Membrane Proton-motive force ($\Delta$p-plas-Fungi); and
4) Bacterial Plasma Membrane Proton-motive force ($\Delta$p-plas-Bact).

Such phenomena can in turn decrease the Gibbs free energy value $\Delta G$ available for the phosphorylation and synthesis of ATP ($\Delta Gp$). The present invention carries out these phenomena in order to inhibit the necessary energy dependent anabolic reactions, potentiating pharmacological therapies, and/or lowering cellular resistance mechanisms (to antimicrobial, antifungal and antineoplastic molecules) as many of these resistance mechanisms make use of the proton motive force or the chemiosmotic potential for their energy needs, to resist and/or efflux these molecules.

Free Radical Generation in Consequence of Modifications of $\Delta\Psi$-Steady

The action of chemical uncouplers for oxidative phosphorylation and other bioenergetic work is believed to depend on the energized state of the membrane (plasma or mitochondrial). Further, it is believed that the energized state of the bacterial membrane or eukaryotic mitochondrial inner membrane, is an electrochemical proton gradient $\Delta\mu H^+$ that is established by primary proton translocation events occurring during cellular respiration and electron transport.

Agents that directly dissipate (depolarize) the $\Delta\mu H^+$, (e.g., by permeabilizing the coupling membrane to the movement of protons or compensatory ions) short-circuits energy coupling, and inhibit bioenergetic work, by inducing a reduction in the membrane potential $\Delta\Psi$-steady. This will occur while respiration (primary proton translocation) continues apace.

For example, the classic uncoupler of oxidative phosphorylation, carbonyl cyanide m-chlorophenylhydrazone (CCCP), induces a reduction in membrane potential $\Delta\Psi$-steady and induces a concomitant generation of ROS, as respiration continues. These agents (uncouplers) generally cannot be used as antimicrobials, antifungals, or antineoplastics, because their effects are correspondingly toxic to all bacterial, fungal and mammalian cells.

However, it has been shown that in many target cells that are resistant to antimicrobials, antifungals, or antineoplastics, a $\Delta p$ uncoupler (like CCCP) will collapse the energy gradient required for an efflux pump and hence induce a strong increase in the intracellular accumulation of these drugs. These results clearly indicate that some resistance mechanisms (such as drug efflux pumps) are driven by the proton motive force. If there were a way to harness this effect to uniquely achieve only "target cell" damage, this selectivity would be a clear improvement upon the universal damaging nature of uncouplers.

The scientific findings and experimental data of the present invention show that as a membrane is depolarized optically, the generation of ROS may well further potentiate the depolarization of affected cells, and further potentiate the antibacterial effects of the present invention. (See, Example VIII).

Free Radical and ROS Generation by Irradiation with the NIMELS Laser

By mechano-optically modifying many of the relevant thermodynamic interactions of the membrane energy transduction process, along with altering $\Delta\Psi$-steady, the present invention can act as an optical uncoupler by lowering the $\Delta\mu H^+$ and $\Delta p$ of the following irradiated membranes:

1) Mammalian Mitochondrial Proton-motive force ($\Delta$p-mito-mam)
2) Fungal Mitochondrial Proton-motive force ($\Delta$p-mito-Fungi)
3) Fungal Plasma Membrane Proton-motive force ($\Delta$p-plas-Fungi)
4) Bacterial Plasma Membrane Proton-motive force ($\Delta$p-plas-Bact)

This lowered $\Delta p$ will cause a series of free radicals and radical oxygen species to be generated because of the altered redox state. The generation of free radicals and reactive oxygen species has been proven experimentally and described herein with the alteration of $\Delta\Psi$-steady to $\Delta\Psi$-trans in the following (see, Example VIII):
1) $\Delta\Psi$-steady-mam+(NIMELS Treatment)$\rightarrow\rightarrow\Delta\Psi$-trans-mam
2) $\Delta\Psi$-steady-fungi+(NIMELS Treatment)$\rightarrow\rightarrow\Delta\Psi$-trans-fungi
3) $\Delta\Psi$-steady-bact+(NIMELS Treatment)$\rightarrow\rightarrow\Delta\Psi$-trans-bact
4) $\Delta\Psi$-mito-fungi+(NIMELS Treatment)$\rightarrow\rightarrow\Delta\Psi$-trans-mito-fungi
5) $\Delta\Psi$-mito-mam+(NIMELS Treatment)$\rightarrow\rightarrow\Delta\Psi$-trans-mito-mam The altered redox state and generation of free radicals and ROS because of the $\Delta\Psi$-steady+(NIMELS j Treatment)$\rightarrow\rightarrow\Delta\Psi$-trans phenomenon, can cause serious further damage to biological membranes such as lipid peroxidation.

Lipid Peroxidation

Lipid peroxidation is a prevalent cause of biological cell injury and death in both the microbial and mammalian world. In this process, strong oxidents cause the breakdown of membrane phospholipids that contain polyunsaturated fatty acids (PUFA's). The severity of the membrane damage can cause local reductions in membrane fluidity and full disruption of bilayer integrity.

Peroxidation of mitochondrial membranes (mamallian cells and fungi) will have detrimental consequences on the respiratory chains resulting in inadequate production of ATP and collapse of the cellular energy cycle. Peroxidation of the plasma membrane (bacteria) can affect membrane permeability, disfunction of membrane proteins such as porins and efflux pumps, inhibition of signal transduction and improper cellular respiration and ATP formation (i.e., the respiratory chains in prokaryotes are housed in the plasma membranes as prokaryotes do not have mitochondria).

Free Radical

A free radical is defined as an atom or molecule that contains an unpaired electron. An example of the damage that a free radical can do in a biological environment is the one-electron (via an existing or generated free radical) removal from bis-allylic C—H bonds of polyunsaturated fatty acids (PUFAs) that will yield a carbon centered free radical.

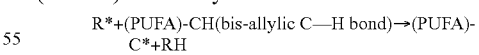
R*+(PUFA)-CH(bis-allylic C—H bond)→(PUFA)-C*+RH

This reaction can initiate lipid peroxidation damage of biological membranes.

A free radical can also add to a nonradical molecule, producing a free radical product.

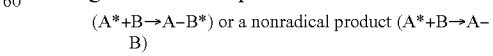
(A*+B→A–B*) or a nonradical product (A*+B→A–B)

An example of this would be the hydroxylation of an aromatic compound by *OH.

Reactive Oxygen Species (ROS)

Oxygen gas is actually a free radical species. However, because it contains two unpaired electrons in different π-antibonding orbitals that have parallel spin in the ground state, the (spin restriction) rule generally prevents $O_2$ from receiving a pair of electrons with parallel spins without a catalyst. Consequently $O_2$ must receive one electron at a time.

There are many significant donors in a cell (prokaryotic and eukaryotic) that are able to stimulate the one-electron reduction of oxygen, that will create an additional radical species.

These are generally categorized as:
The Superoxide ion radical ($O_2^-$)
Hydrogen Peroxide (non-radical) ($H_2O_2$)
Hydroxyl radical (*OH)
Hydroxy ion ($OH^-$)
The Reaction Chain is:

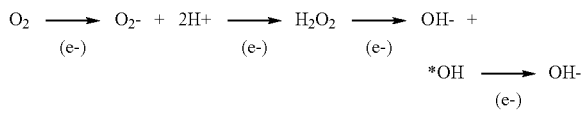

Superoxide

The danger of these molecules to cells is well categorized in the literature. Superoxide, for example, can either act as an oxidizing or a reducing agent.

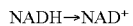

Of higher importance to an organism's metabolism, superoxide can reduce cytochrome C. It is generally believed that the reaction rates of superoxide ($O_2^-$) with lipids (i.e., membranes) proteins, and DNA are too slow to have biological significance.

The protonated form of superoxide hydroperoxyl radical (HOO*) has a lower reduction potential than ($O_2^-$), yet is able to remove hydrogen atoms from PUFA's. Also of note, the pKa value of (HOO*) is 4.8 and the (acid) microenvironment near biological membranes will favor the formation of hydroperoxyl radicals. Furthermore, the reaction of superoxide ($O_2^-$) with any free $F_e^{+3}$ will produce a "perferryl" intermediate which can also react with PUFA's and induce lipid (membrane) peroxidation.

Hydrogen Peroxide

Hydrogen peroxide ($H_2O_2$) is not a good oxidizing agent (by itself) and cannot remove hydrogen from PUFA's. It can, however, cross biological membranes (rather easily) to exert dangerous and harmful effects in other areas of cells. For example, ($H_2O_2$) is highly reactive with transition metals inside microcellular environments, (such as $Fe^{+2}$ and $Cu^+$) that can then create hydroxyl radicals (*OH) (known as the Fenton Reaction). An hydroxyl radical is one of the most reactive species known in biology.

Hydroxyl Radical

Hydroxyl radicals (*OH) will react with almost all kinds of biological molecules. It has a very fast reaction rate that is essentially controlled by the hydroxyl radical (*OH) diffusion rate and the presence (or absence) of a molecule to react near the site of (*OH) creation. In fact, the standard reduction potential (E0') for hydroxyl radical (*OH) is (+2.31 V) a value that is 7× greater than ($H_2O_2$), and is categorized as the most reactive among the biologically relevant free radicals. Hydroxyl radicals will initiate lipid peroxidation in biological membranes, in addition to damaging proteins and DNA.

Reactive Oxygen Species Created from the Peroxidation of PUFAs

Furthermore, the development of lipid peroxidation (from any source) will result in the genesis of three other reactive oxygen intermediate molecules from PUFA's.

(a) alkyl hydroperoxides (ROOH);
Like $H_2O_2$, alkyl hydroperoxides are not technically radical species but are unstable in the presence of transition metals such as such as $Fe^{+2}$ and $Cu^+$.
(b) alkyl peroxyl radicles (ROO*); and
(c) alkoxyl radicles (RO*).

Alkyl peroxyl radicles and alkoxyl radicles are extremely reactive oxygen species and also contribute to the process of propagation of further lipid peroxidation. The altered redox state of irradiated cells and generation of free radicals and ROS because of the $\Delta\Psi$-steady+(NIMELS Treatment)→→$\Delta\Psi$-trans phenomenon is another object of the present invention. This is an additive effect to further alter cellular bioenergetics and inhibit necessary energy dependent anabolic reactions, potentiate pharmacological therapies, and/or lower cellular resistance mechanisms to antimicrobial, antifungal and antineoplastic molecules.

ROS overproduction can damage cellular macromolecules, above all lipids. Lipid oxidation has been shown to modify both the small-scale structural dynamics of biological membranes as well as their more macroscopic lateral organization and altered a packing density dependent reorientation of the component of the dipole moment $\Psi$d. Oxidative damage of the acyl chains (in lipids) causes loss of double bonds, chain shortening, and the introduction of hydroperoxy groups. Hence, these changes are believed to affect the structural characteristics and dynamics of lipid bilayers and the dipole potential $\Psi$d.

Antimicrobial Resistance

Antimicrobial resistance is defined as the ability of a microorganism to survive the effects of an antimicrobial drug or molecule. Antimicrobial resistance can evolve naturally via natural selection, through a random mutation, or through genetic engineering. Also, microbes can transfer resistance genes between one another via mechanisms such as plasmid exchange. If a microorganism carries several resistance genes, it is called multi-resistant or, informally, a "superbug."

Multi-drug resistance in pathogenic bacteria and fungi are a serious problem in the treatment of patients infected with such organisms. At present, it is tremendously expensive and difficult to create or discover new antimicrobial drugs that are safe for human use. Also, there have been resistant mutant organisms that have evolved challenging all known antimicrobial classes and mechanisms. Hence, few antimicrobials have been able to maintain their long-term effectiveness. Most of the mechanisms of antimicrobial drug resistance are known.

The four main mechanisms by which micro-organisms exhibit resistance to antimicrobials are:
a) Drug inactivation or modification;
b) Alteration of target site;
c) Alteration of metabolic pathway; and
d) Reduced drug accumulation: by decreasing drug permeability and/or increasing active efflux on the cell surface.

Resistant Microbe Example

Staphylococcus aureus (S. aureus) is one of the major resistant bacterial pathogens currently plaguing humanity. This gram positive bacterium is primarily found on the mucous membranes and skin of close to half of the adult world-wide population. S. aureus is extremely adaptable to pressure from all known classes of antibiotics. S. aureus was the first bacterium in which resistance to penicillin was found in 1947. Since then, almost complete resistance has been found to methicillin and oxacillin. The "superbug" MRSA (methicillin resistant Staphylococcus aureus) was first detected in 1961, and is now ubiquitous in hospitals and communities worldwide. Today, more than half of all S.

*aureus* infections in the United States are resistant to penicillin, methicillin, tetracycline and erythromycin. Recently, in what were the new classes of antibiotics (antimicrobials of last resort) glycopeptides and oxazolidinones, there have been reports of significant resistance (Vancomycin since 1996 and Zyvox since 2003).

A new variant CA-MRSA, (community acquired MRSA) has also recently emerged as an epidemic, and is responsible for a group of rapidly progressive, fatal diseases including necrotizing pneumonia, severe sepsis and necrotizing fasciitis. Outbreaks of community-associated (CA)-MRSA infections are reported daily in correctional facilities, athletic teams, military recruits, in newborn nurseries, and among active homosexual men. CA-MRSA infections now appear to be almost endemic in many urban regions and cause most CA-*S. aureus* infections.

The scientific and medical community has been attempting to find potentiators of existing antimicrobial drugs and inhibitors of drug resistance systems in bacteria and fungi. Such potentiators and/or inhibitors, if not toxic to humans, would be very valuable for the treatment of patients infected with pathogenic and drug-resistant microbes. In the United States, as many as 80% of individuals are colonized with *S. aureus* at some point. Most are colonized only intermittently; 20-30% are persistently colonized. Healthcare workers, persons with diabetes, and patients on dialysis all have higher rates of colonization. The anterior nares are the predominant site of colonization in adults; other potential sites of colonization include the axilla, rectum, and perineum.

Selective Pharmacological Alteration of $\Delta\Psi$-Steady in Bacteria

There is a relatively new class of bactericidal antibiotics called the lipopeptides of which daptomycin is the first FDA approved member. This antibiotic has demonstrated (in vitro and in vivo) that it can rapidly kill virtually all clinically relevant gram-positive bacteria (such as MRSA) via a mechanism of action distinct from those of other antibiotics on the market at present.

Daptomycin's mechanism of action involves a calcium-dependent incorporation of the lipopeptide compound into the cytoplasmic membrane of bacteria. On a molecular level, it is calcium binding between two aspartate residues (in the daptomycin molecule) that decreases its net negative charge and permits it to better act with the negatively charged phospholipids that are typically found in the cytoplasmic membrane of gram-positive bacteria. There is generally no interaction with fungi or mammalian cells at therapeutic levels, so it is a very selective molecule.

The effects of daptomycin have been proposed to result from this calcium-dependent action on the bacterial cytoplasmic membrane that dissipates the transmembrane membrane electrical potential gradient $\Delta\mu H^+$. This is in effect selective chemical depolarization of only bacterial membranes. It is well known that the maintenance of a correctly energized cytoplasmic membrane is essential to the survival and growth of bacterial cells, nevertheless depolarization (in this manner) is not in and of itself a bacterially lethal action. For example, the antibiotic valinomycin, which causes depolarization in the presence of potassium ions, is bacteriostatic but not bactericidal as would be the case with CCCP.

Conversely, in the absence of a proton motive force $\Delta p$, the main component of which is the transmembrane electrical potential gradient $\Delta\mu H^+$, cells cannot make ATP or take up necessary nutrients needed for growth and reproduction. The collapse of $\Delta\mu H^+$ explains the dissimilar (detrimental) effects produced by daptomycin (e.g., inhibition of protein, RNA, DNA, peptidoglycan, lipoteichoic acid, and lipid biosynthesis).

Further research into the prior-art concerning the drug daptomycin, suggests that the addition of gentamicin or minocycline (to daptomycin) results in the enhancement of its bactericidal activity against MRSA. As both gentamicin and minocycline can be effluxed out of MRSA cells through energy dependent pumps, and are inhibitors of protein synthesis (an anabolic function) at the level of the 30 S bacterial ribosome. This indicates that dissipation of the transmembrane electrical potential gradient $\Delta\mu H^+$ by daptomycin can potentiate certain antimicrobial drugs. This should occur as a result of resistance mechanisms that are rendered less useful by a reduction in the membrane potential $\Delta\Psi$ and the fact that ATP is not available (i.e., the concomitant lowered $\Delta Gp$) for the anabolic function of protein synthesis.

Based on the above, it would clearly be desirable to be able to optically inhibit the activity of drug efflux pumps and/or anabolic reactions in target cells by safely reducing the membrane potential $\Delta\Psi$ ($\Delta\Psi$-steady+(NIMELS Treatment)$\rightarrow\rightarrow\Delta\Psi$-trans) of the cells in a given target area. Methods according to the present invention accomplish this and other tasks with the use of selected infrared wavelengths, e.g., 870 nm and 930 nm, independent of any exogenous chemical agents such as daptomycin. This is a clear improvement over the existing prior art methods that require a systemic drug to accomplish the same task.

Multidrug Resistance Efflux Pumps

Multidrug resistance efflux pumps are now known to be present in gram-positive bacteria, gram-negative bacteria, fungi, and cancer cells. Efflux pumps generally have a polyspecificity of transporters that confers a broad-spectrum of resistance mechanisms. These can strengthen the effects of other mechanisms of antimicrobial resistance such as mutations of the antimicrobial targets or enzymatic modification of the antimicrobial molecules. Active efflux for antimicrobials can be clinically relevant for $\beta$-lactam antimicrobials, marcolides, fluoroquinolones, tetracyclines and other important antibiotics, along with most antifungal compounds including itraconazole and terbinafine.

With efflux pump resistance, a microbe has the capacity to seize an antimicrobial agent or toxic compound and expel it to the exterior (environment) of the cell, thereby reducing the intracellular accumulation of the agent. It is generally considered that the over-expression of one or more of these efflux pumps prevents the intracellular accumulation of the agent to thresholds necessary for its inhibitory activity. Universally in microbes, the efflux of drugs is coupled to the proton motive force that creates electrochemical potentials and/or the energy necessary (ATP) for the needs of these protein pumps. This includes:

1) Mammalian mitochondrial proton-motive force ($\Delta p$-mito-mam);
2) Fungal mitochondrial proton-motive force ($\Delta p$-mito-fungi);
3) Fungal plasma membrane proton-motive force ($\Delta p$-plas-fungi); and
4) Bacterial plasma membrane proton-motive force ($\Delta p$-plas-bact).

Phylogenetically, bacterial antibiotic efflux pumps belong to five superfamilies:
(i) ABC (ATP-binding cassette), which are primary active transporters energized by ATP hydrolysis;
(ii) SMR [small multidrug resistance subfamily of the DMT (drug/metabolite transporters) superfamily];

(iii) MATE [multi-antimicrobial extrusion subfamily of the MOP (multidrug/oligosaccharidyl-lipid/polysaccharide flippases) superfamily];
(iv) MFS (major facilitator superfamily); and
(v) RND (resistance/nodulation/division superfamily), which are all secondary active transporters driven by ion gradients.

The approach of the current invention to inhibit efflux pumps is a general modification (optical depolarization) of the membranes $\Delta\Psi$ within the irradiated area, leading to lower electrochemical gradients that will lower the phosphorylation potential $\Delta Gp$ and energy available for the pumps functional energy needs. It is also the object of the present invention to have the same photobiological mechanism inhibit the many different anabolic and energy driven mechanisms of the target cells, including absorption of nutrients for normal growth.

Reduction of Efflux Pump Energy: Targeting the Driving Force of the Mechanism

Today, there are no drugs that belong to the "energy-blocker" family of molecules that have been developed for clinical use as efflux pump inhibitors.

There are a couple of molecules that have been found to be "general" inhibitors of efflux pumps. Two such molecules are reserpine and verapamil. These molecules were originally recognized as inhibitors of vesicular monoamine transporters and blockers of transmembrane calcium entry (or calcium ion antagonists), respectively. Verapamil is known as an inhibitor of MDR pumps in cancer cells and certain parasites and also improves the activity of tobramycin.

Reserpine inhibits the activity of Bmr and NorA, two gram-positive efflux pumps, by altering the generation of the membrane proton-motive force $\Delta p$ required for the function of MDR efflux pumps. Although these molecules are able to inhibit the ABC transporters involved in the extrusion of antibiotics (i.e., tetracycline), the concentrations necessary to block bacterial efflux are neurotoxic in humans. To date, there has been no mention in the literature of similar experiments with daptomycin. Fungal drug efflux is mediated primarily by two groups of membrane-bound transport proteins: the ATP-binding cassette (ABC) transporters and the major facilitator superfamily (MFS) pumps.

Bacterial Plasma Trans-Membrane Potential $\Delta\Psi$-Plas-Bact and Cell Wall Synthesis During normal cellular metabolism, protons are extruded through the cytoplasmic membrane to form $\Delta\Psi$-plas-bact. This function also acidifies (lower pH) the narrow region near the bacterial plasma membrane. It has been shown in the gram positive bacterium *Bacillus subtilis*, that the activities of peptidoglycan autolysins are increased (i.e., no longer inhibited) when the electron transport system was blocked by adding proton conductors. This suggests that $\Delta\Psi$-plas-bact and $\Delta\mu H^+$ (independent of storing energy for cellular enzymatic functions) potentially has a profound and exploitable influence on cell wall anabolic functions and physiology.

In addition, it has been shown that $\Delta\Psi$-plas-bact uncouplers inhibit peptidoglycan formation with the accumulation of the nucleotide precursors involved in peptidoglycan synthesis, and the inhibition of transport of N-acetylglucosamine (GlcNAc), one of the major biopolymers in peptidoglycan.

Also, there is reference to an antimicrobial compound called tachyplesin that decreases $\Delta\Psi$-plas-bact in gram positive and gram negative pathogens. (Antimicrobial compositions and pharmaceutical preparations thereof. U.S. Pat. No. 5,610,139, the entire teaching of which is incorporated herein by reference.) This compound was shown at sub-lethal concentrations to have the ability to potentiate the cell wall synthesis inhibitor β-lactam antibiotic ampicillin in MRSA. It is desirable to couple the multiple influences of an optically lowered $\Delta\Psi$-plas-bact (i.e., increased cell wall autolysis, inhibited cell wall synthesis, and cell wall antimicrobial potentiation) to any other relevant antimicrobial therapy that targets bacterial cell walls. This is especially relevant in gram positive bacteria such as MRSA that do not have efflux pumps as resistance mechanisms for cell wall inhibitory antimicrobial compounds.

Cell wall inhibitory compounds do not need to gain entry through a membrane in gram positive bacteria, as is necessary with gram negative bacteria, to exhibit effects against the cell wall. Experimental evidence has proven (see, Example XII) that the NIMELS laser and its concomitant optical $\Delta\Psi$-plas-bact lowering phenomenon is synergistic with cell wall inhibitory antimicrobials in MRSA. This must function via the inhibition of anabolic (periplasmic) ATP coupled functions, as MRSA does not have efflux pumps that function on peptidoglycan inhibitory antimicrobials, as they do not need to enter the cell to be effective.

$\Delta\Psi$-Plas-Fungi and $\Delta\Psi$-Mito-Fungi: Necessities for Correct Cellular function and antifungal resistance During normal cellular metabolism $\Delta\Psi$-mito-fungi is generated in the mitochondria via the electron transport system that then generates ATP via the mitochondrial ATP synthase enzyme system. It is the ATP that then powers the plasma membrane-bound $H^+$-ATPase to generate $\Delta\Psi$-plas-fungi. It has previously been found that fungal mitochondrial ATP synthase is inhibited by the chemical, polygodial, in a dose-dependent manner (Lunde and Kubo, Antimicrob Agents Chemother. 2000 July; 44(7): 1943-1953, the entire teaching of which is incorporated herein by reference.) It was further found that this induced reduction of the cytosolic ATP concentration leads to a suppression of the plasma membrane-bound $H^+$-ATPase that generates $\Delta\Psi$-plas-fungi, and that this impairment further weakens other cellular activities. Additionally, the lowering of the $\Delta\Psi$-plas-fungi will cause plasma membrane bioenergetic and thermodynamic disruption leading to an influx of protons that collapses the proton motive force and hence inhibits nutrient uptake.

Of further importance, ATP is necessary for the biosynthesis of the fungal plasma membrane lipid ergosterol. Ergosterol is the structural lipid that is targeted by the majority of relevant commercial antifungal compounds used in medicine today (i.e., azoles, terbinafine and itraconazole).

Studies have shown that two antimicrobial peptides (Pep2 and Hst5) have the ability to cause ATP to be effluxed out of fungal cells (i.e., depleting intracellular ATP concentrations) and that this lowered cytosolic ATP causes the inactivation of ABC transporters CDR1 and CDR2 which are ATP-dependent efflux pumps of antifungal agents.

There is an advantage to using an optical method to depolarize membranes and deplete cellular ATP in fungus, as a potentiator to efflux pump inhibition and anabolic reactions. Hence, it would be desirable to optically alter either the $\Delta\Psi$-plas-fungi and/or $\Delta\Psi$-mito-fungi to inhibit necessary cellular functions, ATP generation, and potentiate antifungal compounds.

Therefore, one of the strategies for preventing drug resistance (via efflux pumps) is to decrease the level of intracellular ATP which induces inactivation of the ATP-dependent efflux pumps. In fungal pathogens, there have been no acceptable chemical agents to accomplish this task. The NIMELS effect however has the ability to accomplish this goal optically, and experimental evidence has demonstrated that the NIMELS laser and phenomenon in fungi, is synergistic with antifungal compounds. (See, Example XIII).

This NIMELS effect will occur in accordance with methods and systems disclosed herein, without causing thermal or ablative mechanical damage to the cell membranes. This combined and targeted low dose approach is a distinct variation and improvement from all existing methods that would otherwise cause actual mechanical damage to all membranes within the path of a beam of energy.

In a first aspect, the invention provides a method of modifying the dipole potential $\Psi d$ of all membranes within the path of a NIMELS beam ($\Psi$d-plas-mam, $\Psi$d-mito-mam, $\Psi$d-plas-fungi, $\Psi$d-mito-fungi, and $\Psi$d-plas-bact) to set in motion the cascade of further alterations of $\Delta\Psi$ and $\Delta p$ in the same membranes.

The bioenergetic steady-state membrane potentials $\Delta\Psi$-steady of all irradiated cells ($\Delta\Psi$-steady-mam, $\Delta\Psi$-steady-fungi, $\Delta\Psi$-steady-Bact, $\Delta\Psi$-steady-mito-mam and $\Delta\Psi$-steady-mito-fungi) are altered to $\Delta\Psi$-trans values ($\Delta\Psi$-trans-mam, $\Delta\Psi$-trans-fungi, $\Delta\Psi$-trans-Bact, $\Delta\Psi$-trans-mito-mam and $\Delta\Psi$-trans-mito-fungi). This results in a concomitant depolarization and quantifiable alteration in the absolute value of the $\Delta p$ for all irradiated cells ($\Delta p$-mito-mam, $\Delta p$-mito-Fungi, $\Delta p$-plas-Fungi and $\Delta p$-plas-Bact).

These phenomena occur without intolerable risks and/or intolerable adverse effects to biological subjects (e.g., a mammalian tissue, cell or certain biochemical preparations such as a protein preparation) in/at the given target site other than the targeted biological contaminants (bacteria and fungi), by irradiating the target site with optical radiation of desired wavelength(s), power density level(s), and/or energy density level(s).

In certain embodiments, such applied optical radiation may have a wavelength from about 850 nm to about 900 nm, at a NIMELS dosimetry, as described herein. In exemplary embodiments, wavelengths from about 865 nm to about 875 nm are utilized. In further embodiments, such applied radiation may have a wavelength from about 905 nm to about 945 nm at a NIMELS dosimetry. In certain embodiments, such applied optical radiation may have a wavelength from about 925 nm to about 935 nm. In representative non-limiting embodiments exemplified hereinafter, the wavelength employed is 930 nm.

Bioenergetic steady-state membrane potentials may be modified, in exemplary embodiments, as noted below, and may employ multiple wavelength ranges including ranges bracketing 870 and 930 nm, respectively.

The NIMELS Potentiation Magnitude Scale (NPMS)

As discussed in more detail supra, NIMELS parameters include the average single or additive output power of the laser diodes and the wavelengths (870 nm and 930 nm) of the diodes. This information, combined with the area of the laser beam or beams (cm$^2$) at the target site, the power output of the laser system and the time of irradiation, provide the set of information which may be used to calculate effective and safe irradiation protocols according to the invention.

Based on these novel resistance reversal and antimicrobial potentiation interactions available with the NIMELS laser, there needs to be a quantitative value for the "potentiation effect" that will hold true for each unique antimicrobial and laser dosimetry.

A new set of parameters are defined that will take into account the implementation of any different dosimetric value for the NIMELS laser and any MIC value for a given antimicrobial being examined. This can be simply tailored to the NIMELS laser system and methods by creating only a set of variables that quantify CFU's of pathogenic organisms within any given experimental or treatment parameter with the NIMELS system.

These parameters create a scale called the NIMELS Potentiation Magnitude Scale (NPMS) and exploits the NIMELS lasers inherent phenomenon of reversing resistance and/or potentiating the MIC of antimicrobial drugs, while also producing a measure of safety against burning and injuring adjacent tissues, with power, and/or treatment time.

The NPMS scale measures the NIMELS effect number (Ne) between 1 to 10, where the goal is to gain a Ne of $\geq 4$ in reduction of CFU count of a pathogen, at any safe combination of antimicrobial concentration and NIMELS dosimetry. Although CFU count is used here for quantifying pathogenic organism, other means of quantification such as, for example, dye detection methods or polymerase chain reaction (PCR) methods can also be used to obtain values for A, B, and Np parameters.

The NIMELS effect number Ne is an interaction coefficient indicating to what extent the combined inhibitory/bacteriostatic effect of an antimicrobial drug is synergistic with the NIMELS laser against a pathogen target without harm to healthy tissue.

The NIMELS potentiation number (Np) is a value indicating whether the antimicrobial at a given concentration is synergistic, or antagonistic, to the pathogen target without harm to healthy tissue. Hence, within any given set of standard experimental or treatment parameters:

A=CFU Count of pathogen with NIMELS alone;
B=CFU Count of pathogen with antimicrobial alone;
Np=CFU Count of pathogen with (NIMELS+Antimicrobial); and
Ne=(A+B)/2Np;
Interpretation of NIMELS effect number Ne:
where:
If 2Np<A+B then the (given) antimicrobial has been successfully potentiated with the NIMELS laser at the employed concentrations and dosimetries.
then:
If Ne=1 then there is no potentiation effect. If Ne >1 then there is a potentiation effect. If Ne $\geq 2$ then there is at least a 50% potentiation effect on the antimicrobial. If Ne $\geq 4$ then there is at least a 75% potentiation effect on the antimicrobial. If Ne $\geq 10$ then there is at least a 90% potentiation effect on the antimicrobial.

A=110 CFU

B=120 CFU

Np=75 CFU $Ne$=(110 CFU+120 CFU)/2(75)=1.5     Sample calculation 1

A=150 CFU

B=90 CFU

Np=30 CFU $Ne$=(150 CFU+90 CFU)/2(30)=4     Sample calculation 2

In general, it can be advantageous to use a lower dose of antimicrobials when treating microbial infections, as the antimicrobials are expensive and by and large associated with undesirable side effects that can include systemic kidney and/or liver damage. Therefore, it is desirable to devise methods to lower and or potentiate the MIC of antimicrobials. The present invention provides systems and methods to reduce the MIC of antimicrobial molecules when the area being treated is concomitantly treated with the NIMELS laser system.

If the MIC of an antimicrobial is reduced for a localized and resistant focal infection (e.g., skin, diabetic foot, bedsore), the therapeutic efficacy of many of the older, cheaper and safer antimicrobials to treat these infections will be restored. Therefore, decreasing the MIC of an antimicrobial, by the addition of the NIMELS laser (e.g., generating a value of Ne that is in one aspect >1 and in another aspect $\geq 4$ and yet in another aspect $\leq 10$), represents a positive step forward in restoring the once lost therapeutic efficacy of antibiotics.

Therefore, in one aspect, this invention provides methods and systems that will reduced the MIC of antimicrobial molecules necessary to eradicate or at least attenuate microbial pathogens via a depolarization of membranes within the irradiated field which will decrease the membrane potential $\Delta\Psi$ of the irradiated cells. This weakened $\Delta\Psi$ will cause an affiliated weakening of the proton motive force $\Delta p$, and the associated bioenergetics of all affected membranes. It is a further object of the present invention that this "NIMELS effect" potentiate existing antimicrobial molecules against microbes infecting and causing harm to human hosts.

In certain embodiments, such applied optical radiation has a wavelength from about 850 nm to about 900 nm, at a NIMELS dosimetry, as described herein. In exemplary embodiments, wavelengths from about 865 nm to about 875 nm are utilized. In further embodiments, such applied radiation has a wavelength from about 905 nm to about 945 nm at a NIMELS dosimetry. In certain embodiments, such applied optical radiation has a wavelength from about 925 nm to about 935 nm. In one aspect, the wavelength employed is 930 nm.

Microbial pathogens that have their bioenergetic systems affected by the NIMELS laser system according to the present invention include microorganisms such as, for example, bacteria, fungi, molds, mycoplasmas, protozoa, and parasites. Exemplary embodiments, as noted below may employ multiple wavelength ranges including ranges bracketing 870 and 930 nm, respectively.

In the methods according to one aspect of the invention, irradiation by the wavelength ranges contemplated are performed independently, in sequence, in a blended ratio, or essentially concurrently (all of which can utilize pulsed and/or continuous-wave, CW, operation).

Irradiation with NIMELS energy at NIMELS dosimetry to the biological contaminant is applied prior to, subsequent to, or concomitant with the administration of an antimicrobial agent. However, said NIMELS energy at NIMELS dosimetry can be administered after antimicrobial agent has reached a "peak plasma level" in the infected individual or other mammal. It should be noted that the co-administered antimicrobial agent ought to have antimicrobial activity against any naturally sensitive variants of the resistant target contaminant.

The wavelengths irradiated according to the present methods and systems increase the sensitivity of a contaminant to the level of a similar non-resistant contaminant strain at a concentration of the antimicrobial agent of about 0.01 M or less, or about 0.001 M or less, or about 0.0005 M or less.

The methods of the invention slow or eliminate the progression of microbial contaminants in a target site, improve at least some symptoms or asymptomatic pathologic conditions associated with the contaminants, and/or increase the sensitivity of the contaminants to an antimicrobial agent. For example, the methods of the invention result in a reduction in the levels of microbial contaminants in a target site and/or potentiate the activity of antimicrobial compounds by increasing the sensitivity of a biological contaminant to an antimicrobial agent to which the biological contaminant has evolved or acquired resistance, without an adverse effect on a biological subject. The reduction in the levels of microbial contaminants can be, for example, at least 10%, 20%, 30%, 50%, 70% or more as compared to pretreatment levels. With regard to sensitivity of a biological contaminant to an antimicrobial agent, the sensitivity is potentiated by at least 10%.

In another aspect, the invention provides a system to implement the methods according to other aspects of the invention. Such a system includes a laser oscillator for generating the radiation, a controller for calculating and controlling the dosage of the radiation, and a delivery assembly (system) for transmitting the radiation to the treatment site through an application region. Suitable delivery assemblies/systems include hollow waveguides, fiber optics, and/or free space/beam optical transmission components. Suitable free space/beam optical transmission components include collimating lenses and/or aperture stops.

In one form, the system utilizes two or more solid state diode lasers to function as a dual wavelength near-infrared optical source. The two or more diode lasers may be located in a single housing with a unified control. The two wavelengths can include emission in two ranges from about 850 nm to about 900 nm and from about 905 nm to about 945 nm. The laser oscillator of the present invention is used to emit a single wavelength (or a peak value, e.g., central wavelength) in one of the ranges disclosed herein. In certain embodiments, such a laser is used to emit radiation substantially within the about 865-875 nm and the about 925-935 nm ranges.

Systems according to the present invention can include a suitable optical source for each individual wavelength range desired to be produced. For example, a suitable solid stated laser diode, a variable ultra-short pulse laser oscillator, or an ion-doped (e.g., with a suitable rare earth element) optical fiber or fiber laser is used. In one form, a suitable near infrared laser includes titanium-doped sapphire. Other suitable laser sources including those with other types of solid state, liquid, or gas gain (active) media may be used within the scope of the present invention.

According to one embodiment of the present invention, a therapeutic system includes an optical radiation generation system adapted to generate optical radiation substantially in a first wavelength range from about 850 nm to about 900 nm, a delivery assembly for causing the optical radiation to be transmitted through an application region, and a controller operatively connected to the optical radiation generation device for controlling the dosage of the radiation transmitted through the application region, such that the time integral of the power density and energy density of the transmitted radiation per unit area is below a predetermined threshold. Also within this embodiment, are therapeutic systems especially adapted to generate optical radiation substantially in a first wavelength range from about 865 nm to about 875 nm.

According to further embodiments, a therapeutic system includes an optical radiation generation device that is configured to generate optical radiation substantially in a second wavelength range from about 905 nm to about 945 nm; in certain embodiments the noted first wavelength range is simultaneously or concurrently/sequentially produced by the optical radiation generation device. Also within the scope of this embodiment, are therapeutic systems especially adapted to generate optical radiation substantially in a first wavelength range from about 925 nm to about 935 nm.

The therapeutic system can further include a delivery assembly (system) for transmitting the optical radiation in the second wavelength range (and where applicable, the first wavelength range) through an application region, and a controller operatively for controlling the optical radiation generation device to selectively generate radiation substantially in the first wavelength range or substantially in the second wavelength range or any combinations thereof.

According to one embodiment, the delivery assembly comprises one or more optical fibers having an end configured and arranged for insertion in patient tissue at a location within an optical transmission range of the medical device, wherein the radiation is delivered at a NIMELS dosimetry to the tissue surrounding the medical device. The delivery assembly may further comprise a free beam optical system.

According to a further embodiment, the controller of the therapeutic system includes a power limiter to control the dosage of the radiation. The controller may further include memory for storing a patient's profile and dosimetry calculator for calculating the dosage needed for a particular target site based on the information input by an operator. In one aspect, the memory may also be used to store information about different types of diseases and the treatment profile, for example, the pattern of the radiation and the dosage of the radiation, associated with a particular application.

The optical radiation can be delivered from the therapeutic system to the application site in different patterns. The radiation can be produced and delivered as a continuous wave (CW), or pulsed, or a combination of each. For example, in a single wavelength pattern or in a multi-wavelength (e.g., dual-wavelength) pattern. For example, two wavelengths of radiation can be multiplexed (optically combined) or transmitted simultaneously to the same treatment site. Suitable optical combination techniques can be used, including, but not limited to, the use of polarizing beam splitters (combiners), and/or overlapping of focused outputs from suitable mirrors and/or lenses, or other suitable multiplexing/combining techniques. Alternatively, the radiation can be delivered in an alternating pattern, in which the radiation in two wavelengths are alternatively delivered to the same treatment site. An interval between two or more pulses may be selected as desired according to NIMELS techniques of the present invention. Each treatment may combine any of these modes of transmission. The intensity distributions of the delivered optical radiation can be selected as desired.

Exemplary embodiments include top-hat or substantially top-hat (e.g., trapezoidal, etc.) intensity distributions. Other intensity distributions, such as Gaussian may be used.

As used herein, the term "biological contaminant" is intended to mean a contaminant that, upon direct or indirect contact with the target site, is capable of undesired and/or deleterious effect(s) on the target site (e.g., an infected tissue or organ of a patient) or upon a mammal in proximity of the target site (e.g., such as, for example, in the case of a cell, tissue, or organ transplanted in a recipient, or in the case of a device used on a patient). Biological contaminants according to the invention are microorganisms such as, for example, bacteria, fungi, molds, mycoplasmas, protozoa, parasites, known to those of skill in the art to generally be found in the target sites.

One of skill in the art will appreciate that the methods and systems of the invention may be used in conjunction with a variety of biological contaminants generally known to those skilled in the art. The following lists are provided solely for the purpose of illustrating the broad scope of microorganisms which may be targeted according to the methods and devices of the present invention and are not intended to limit the scope of the invention.

Accordingly, illustrative non-limiting examples of biological contaminants (pathogens) include, but are not limited to, any bacteria, such as, for example, *Escherichia, Enterobacter, Bacillus, Campylobacter, Corynebacterium, Klebsiella, Treponema, Vibrio, Streptococcus* and *Staphylococcus*.

To further illustrate, biological contaminants contemplated include, but are not limited to, any fungus, such as, for example, *Trichophyton, Microsporum, Epidermophyton, Candida, Scopulariopsis brevicaulis, Fusarium* spp., *Aspergillus* spp., *Alternaria, Acremonium, Scytalidinum dimidiatum*, and *Scytalidinium hyalinum*. Parasites may also be targeted biological contaminants such as *Trypanosoma* and malarial parasites, including *Plasmodium* species, as well as molds; mycoplasms and prions. Viruses include, for example, human immuno-deficiency viruses and other retroviruses, herpes viruses, parvoviruses, filoviruses, circoviruses, paramyxoviruses, cytomegaloviruses, hepatitis viruses (including hepatitis B and hepatitis C), pox viruses, toga viruses, Epstein-Barr virus and parvoviruses may also be targeted.

It will be understood that the target site to be irradiated need not be already infected with a biological contaminant. Indeed, the methods of the present invention may be used "prophylactically," prior to infection. Further embodiments include use on medical devices such as catheters, (e.g., IV catheter, central venous line, arterial catheter, peripheral catheter, dialysis catheter, peritoneal dialysis catheter, epidural catheter), artificial joints, stents, external fixator pins, chest tubes, gastronomy feeding tubes, etc.

In certain instances, irradiation may be palliative as well as prophylactic. Hence, the methods of the invention are used to irradiate a tissue or tissues for a therapeutically effective amount of time for treating or alleviating the symptoms of an infection. The expression "treating or alleviating" means reducing, preventing, and/or reversing the symptoms of the individual treated according to the invention, as compared to the symptoms of an individual receiving no such treatment.

One of skill in the art will appreciate that the invention is useful in conjunction with a variety of diseases caused by or otherwise associated with any microbial, fungal, and viral infection (see, Harrison's, *Principles of Internal Medicine*, 13th Ed., McGraw Hill, New York (1994), the entire teaching of which is incorporated herein by reference). In certain embodiments, the methods and the systems according to the invention are used in concomitance with traditional therapeutic approaches available in the art (see, e.g., Goodman and Gilman's, The Pharmacological Basis of Therapeutics, 8th ed, 1990, Pergmon Press, the entire teaching of which is incorporated herein by reference.) to treat an infection by the administration of known antimicrobial agent compositions. The terms "antimicrobial composition", "antimicrobial agent" refer to compounds and combinations thereof that are administered to an animal, including human, and which inhibit the proliferation of a microbial infection (e.g., antibacterial, antifungal, and antiviral).

The wide breath of applications contemplated include, for example, a variety of dermatological, podiatric, pediatric, and general medicine to mention but a few.

The interaction between a target site being treated and the energy imparted is defined by a number of parameters including: the wavelength(s); the chemical and physical properties of the target site; the power density or irradiance of beam; whether a continuous wave (CW) or pulsed irradiation is being used; the laser beam spot size; the exposure time, energy density, and any change in the physical properties of the target site as a result of laser irradiation with any of these parameters. In addition, the physical properties (e.g., absorption and scattering coefficients, scattering anisotropy, thermal conductivity, heat capacity, and mechanical strength) of the target site may also affect the overall effects and outcomes.

The NIMELS dosimetry denotes the power density ($W/cm^2$) and the energy density ($J/cm^2$; where 1 Watt=1 Joule/second) values at which a subject wavelength is capable of generating ROS and thereby reducing the level of a biological contaminant in a target site, and/or irradiating the contaminant to increase the sensitivity of the biological contaminant through the lowering of $\Delta\Psi$ with concomitant generation of ROS to an antimicrobial agent that said contaminant is resistant to without intolerable risks and/or intolerable side effects on a biological moiety (e.g., a mammalian cell, tissue, or organ) other than the biological contaminant.

As discussed in Boulnois 1986, (Lasers Med. Sci. 1:47-66 (1986), the entire teaching of which is incorporated herein by reference), at low power densities (also referred to as irradiances) and/or energies, the laser-tissue interactions can be described as purely optical (photochemical), whereas at higher power densities photo-thermal interactions ensue. In certain embodiments, exemplified hereinafter, NIMELS dosimetry parameters lie between known photochemical and photo-thermal parameters in an area traditionally used for photodynamic therapy in conjunction with exogenous drugs, dyes, and/or chromophores, yet can function in the realm of photodynamic therapy without the need of exogenous drugs, dyes, and/or chromophores.

The energy density—also expressible as fluence, or the product (or integral) of particle or radiation flux and time—for medical laser applications in the art typically varies between about 1 J/cm$^2$ to about 10,000 J/cm$^2$ (five orders of magnitude), whereas the power density (irradiance) varies from about $1\times10^{-3}$ W/cm$^2$ to over about $10^{12}$ W/cm$^2$ (15 orders of magnitude). Upon taking the reciprocal correlation between the power density and the irradiation exposure time, it can be observed that approximately the same energy density is required for any intended specific laser-tissue interaction. As a result, laser exposure duration (irradiation time) is the primary parameter that determines the nature and safety of laser-tissue interactions. For example, if one were mathematically looking for thermal vaporization of tissue in vivo (non-ablative) (based on Boulnois 1986), it can be seen that to produce an energy density of 1000 J/cm$^2$ (see, Table 1) one could use any of the following dosimetry parameters:

TABLE 1

Example of Values Derived on the Basis of the Boulnois Table

| POWER DENSITY | TIME | ENERGY DENSITY |
|---|---|---|
| $1 \times 10^5$ W/cm$^2$ | 0.01 sec. | 1000 J/cm$^2$ |
| $1 \times 10^4$ W/cm$^2$ | 0.10 sec. | 1000 J/cm$^2$ |
| $1 \times 10^3$ W/cm$^2$ | 1.00 sec. | 1000 J/cm$^2$ |

This progression describes a suitable method or basic algorithm that can be used for a NIMELS interaction against a biological contaminant in a tissue. In other words, this mathematical relation is a reciprocal correlation to achieve a laser-tissue interaction phenomena. This ratioinale can be used as a basis for dosimetry calculations for the observed antimicrobial phenomenon imparted by NIMELS energies with insertion of NIMELS experimental data in the energy density and time and power parameters.

On the basis of the particular interactions at the target site being irradiated (such as the chemical and physical properties of the target site; whether continuous wave (CW) or pulsed irradiation is being used; the laser beam spot size; and any change in the physical properties of the target site, e.g., absorption and scattering coefficients, scattering anisotropy, thermal conductivity, heat capacity, and mechanical strength, as a result of laser irradiation with any of these parameters), a practitioner is able to adjust the power density and time to obtain the desired energy density.

The examples provided herein show such relationships in the context of both in vitro and in vivo treatments. Hence, in the context of treating, e.g., onychomycosis or infected wounds for spot sizes having a diameter of 1-4 cm, power density values were varied from about 0.5 W/cm$^2$ to about 5 W/cm$^2$ to stay within safe and non-damaging/minimally damaging thermal laser-tissue interactions well below the level of "denaturization" and "tissue overheating". Other suitable spot sizes may be used.

With this reciprocal correlation, the threshold energy density needed for a NIMELS interaction with these wavelengths can be maintained independent of the spot-size so long as the desired energies are delivered. In exemplary embodiments, the optical energy is delivered through a uniform geometric distribution to the tissues (e.g., a flat-top, or top-hat progression). With such a technique, a suitable NIMELS dosimetry sufficient to generate ROS (a NIMELS effect) can be calculated to reach the threshold energy densities required to reduce the level of a biological contaminant and/or to increase the sensitivity of the biological contaminant to an antimicrobial agent that said contaminant is resistant to, but below the level of "denaturization" and "tissue overheating".

NIMELS dosimetries exemplified herein (e.g., Onychomycosis) to target microbes in vivo, were from about 200 J/cm$^2$ to about 700 J/cm$^2$ for approximately 100 to 700 seconds. These power values do not approach power values associated with photoablative or photothermal (laser/tissue) interactions.

The intensity distribution of a collimated laser beam is given by the power density of the beam, and is defined as the ratio of laser output power to the area of the circle in (cm$^2$) and the spatial distribution pattern of the energy. Hence, the illumination pattern of a 1.5 cm irradiation spot with an incident Gaussian beam pattern of the area 1.77 cm$^2$ can produce at least six different power density values within the 1.77 cm$^2$ irradiation area. These varying power densities increase in intensity (or concentration of power) over the surface area of the spot from 1 (on the outer periphery) to 6 at the center point. In certain embodiments of the invention, a beam pattern is provided which overcomes this inherent error associated with traditional laser beam emissions.

NIMELS parameters may be calculated as a function of treatment time (Tn) as follows: Tn=Energy Density/Power Density.

In certain embodiments (see, e.g., the in vitro experiments hereinbelow), Tn is from about 50 to about 300 seconds; in other embodiments, Tn is from about 75 to about 200 seconds; in yet other embodiments, Tn is from about 100 to about 150 seconds. In in vivo embodiments, Tn is from about 100 to about 1200 seconds.

Utilizing the above relationships and desired optical intensity distributions, e.g., flat-top illumination geometries as described herein, a series of in vivo energy parameters have been experimentally proven as effective for NIMELS microbial decontamination therapy in vitro. A key parameter for a given target site has thus been shown to be the energy density required for NIMELS therapy at a variety of different spot sizes and power densities.

"NIMELS dosimetry" encompasses ranges of power density and/or energy density from a first threshold point at which a subject wavelength according to the invention is capable of optically reducing $\Delta\Psi$ in a target site to a second end-point and/or to increase the sensitivity of the biological contaminant to an antimicrobial agent that said contaminant is resistant to via generation of ROS, immediately before those values at which an intolerable adverse risk or effect is detected (e.g., thermal damage such as poration) on a biological moiety. One of skill in the art will appreciate that under certain circumstances adverse effects and/or risks at a target site (e.g., a mammalian cell, tissues, or organ) may be tolerated in view of the inherent benefits accruing from the methods of the invention. Accordingly, the stopping point contemplated are those at which the adverse effects are considerable and, thus, undesired (e.g., cell death, protein denaturation, DNA damage, morbidity, or mortality).

In certain embodiments, e.g., for in vivo applications, the power density range contemplated herein is from about 0.25 to about 40 W/cm$^2$. In other embodiments, the power density range is from about 0.5 W/cm$^2$ to about 25 W/cm$^2$.

In further embodiments, power density ranges can encompass values from about 0.5 W/cm$^2$ to about 10 W/cm$^2$. Power densities exemplified herein are from about 0.5 W/cm$^2$ to about 5 W/cm$^2$. Power densities in vivo from about 1.5 to about 2.5 W/cm$^2$ have been shown to be effective for various microbes.

Empirical data appears to indicate that higher power density values are generally used when targeting a biological contaminant in an in vitro setting (e.g., plates) rather than in vivo (e.g., toe nail).

In certain embodiments (see, in vitro examples below), the energy density range contemplated herein is greater than 50 J/cm$^2$ but less than about 25,000 J/cm$^2$. In other embodiments, the energy density range is from about 750 J/cm$^2$ to about 7,000 J/cm$^2$. In yet other embodiments, the energy density range is from about 1,500 J/cm$^2$ to about 6,000 J/cm$^2$ depending on whether the biological contaminant is to be targeted in an in vitro setting (e.g., plates) or in vivo (e.g., toe nail or surrounding a medical device).

In certain embodiments (see, in vivo examples below), the energy density is from about 100 J/cm$^2$ to about 500 J/cm$^2$. In yet other in vivo embodiments, the energy density is from about 175 J/cm$^2$ to about 300 J/cm$^2$. In yet other embodiments, the energy density is from about 200 J/cm$^2$ to about 250 J/cm$^2$. In some embodiments, the energy density is from about 300 J/cm$^2$ to about 700 J/cm$^2$. In some other embodiments, the energy density is from about 300 J/cm$^2$ to about 500 J/cm$^2$. In yet others, the energy density is from about 300 J/cm$^2$ to about 450 J/cm$^2$.

Power densities empirically tested for various in vitro treatment of microbial species were from about 1 W/cm$^2$ to about 10 W/cm$^2$.

One of skill in the art will appreciate that the identification of particularly suitable NIMELS dosimetry values within the power density and energy density ranges contemplated herein for a given circumstance may be empirically done via routine experimentation. Practitioners (e.g., dentists) using near infrared energies in conjunction with periodontal treatment routinely adjust power density and energy density based on the exigencies associated with each given patient (e.g., adjust the parameters as a function of tissue color, tissue architecture, and depth of pathogen invasion). As an example, laser treatment of a periodontal infection in a light-colored tissue (e.g., a melanine deficient patient) will have greater thermal safety parameters than darker tissue, because the darker tissue will absorb near-infrared energy more efficiently, and hence transform these near-infrared energies to heat in the tissues faster. Hence, the obvious need for the ability of a practitioner to identify multiple different NIMELS dosimetry values for different therapy protocols.

As illustrated infra, it has been found that antibiotic resistant bacteria may be effectively treated according to the methods of the present invention. In addition, it has been found that the methods of this invention may be used to augment traditional approaches, to be used in combination with, in lieu of tradition therapy, or even serially as an effective therapeutic approach. Accordingly, the invention may be combined with antibiotic treatment. The term "antibiotic" includes, but is not limited to, β-lactams, penicillins, and cephalosporins, vancomycins, bacitracins, macrolides (erythromycins), ketolides (telithromycin), lincosamides (clindomycin), chloramphenicols, tetracyclines, aminoglycosides (gentamicins), amphotericns, anilinouracils, cefazolins, clindamycins, mupirocins, sulfonamides and trimethoprim, rifampicins, metronidazoles, quinolones, novobiocins, polymixins, oxazolidinone class (e.g., linezolid), glycylcyclines (e.g., tigecycline), cyclic lipopeptides (e.g., daptomycin), pleuromutilins (e.g., retapamulin) and gramicidins and the like and any salts or variants thereof. It also understood that it is within the scope of the present invention that the tetracyclines include, but are not limited to, immunocycline, chlortetracycline, oxytetracycline, demeclocycline, methacycline, doxycycline and minocycline and the like. It is also further understood that it is within the scope of the present invention that aminoglycoside antibiotics include, but are not limited to, gentamicin, amikacin and neomycin, and the like.

As illustrated below, it has been found that antifungal resistant fungi may be effectively treated according to the methods of the invention. In addition, it has been found that the methods of the present invention may be used to augment traditional approaches, to be used in combination with, in lieu of, traditional therapy, or even serially as an effective therapeutic approach. Accordingly, the invention may be combined with antifungal treatment. The term "antifungal" includes, but is not limited to, polyenes, azoles, imidazoles, triazoles, allylamines, echinocandins, cicopirox, flucytosine, griseofulvin, amorolofine, sodarins and combinations thereof (including salts thereof.

As illustrated below, it has been postulated that antineoplastic resistant cancer may be effectively treated according to the methods of the present invention. In addition, it has been found that the methods of the invention may be used to augment traditional approaches, to be used in combination with, in lieu of tradition therapy, or even serially as an effective therapeutic approach. Accordingly, the invention may be combined with antineoplastic treatment. There term "antineoplastic" includes, but is not limited to, actinomycin, anthracyclines, bleomycin, plicamycin, mitomycin, taxanes, etoposide, teniposide and combinations thereof (including salts thereof).

A common tenet in the prior art of trying to find an inhibitor of drug resistance systems in bacteria and fungi, or a potentiator of antimicrobial agents has always been that such agents must be non-toxic to the mammalian tissues that are infected to have any intrinsic value. Furthermore, it has always been a fact that antimicrobials affect bacterial or fungal cellular processes that are not common to the mammalian host, and, hence, are generally safe and therapeutic in nature and design. In the prior art, if antimicrobials, potentiators, and/or resistance reversal entities were to also affect the mammalian cells in the same manner as they damage the pathogens, they could not be used safely as a therapy.

In the current invention, the experimental data (see, e.g., Examples I-X) supports a universal alteration of $\Delta\Psi$ and $\Delta p$ among all cell types, and hence leads to the notion that not only the electro-mechanical, but also the electro-dynamical aspects of all cell membranes, have no differing properties that can adequately be separated. This indicates that all cells in the path of the beam are affected with depolarization, not only the pathogenic cells (non-desired cells).

By reaffirming what the photobiology and cellular energetics data of the NIMELS system has already illuminated (i.e., that all of membrane energetics are affected in the same way across prokaryotic and eukaryotic species), techniques according to the present invention utilize this universal optical depolarizing effect to be independently exploited in non-desired cells, by adding antimicrobial molecules to a therapeutic regimen, and potentiating such molecules in (only) non-desired cells.

Such a targeted therapeutic outcome can exploit the NIMELS laser's effect of universal depolarization, which can be more graded and transient to the mammalian cells in the path of the therapeutic beam, than to the bacteria and fungi. Hence, as the experimental data suggests, the measures of temporal and energetic robustness of the mammalian cells must be greater in the face of optical depolarization and ROS generation, than is seen in the bacterial or fungal cells.

The examples below provide experimental evidence proving the concept of universal optical membrane depolarization coupled to our current understanding of photobiology and cellular energetics and the conservation of thermodynamics as applied to cellular processes.

EXAMPLES

The following examples are included to demonstrate exemplary embodiments of the present invention and are not intended to limit the scope of the invention. Those of skill in the art, will appreciate that many changes can be made in the specific embodiments and still obtain a like or similar result without departing from the spirit and scope of the present invention.

Example I

TABLE 2

MIC values for Susceptible, Intermediate and Resistant *S. aureus* Minimum Inhibitory Concentration (MIC) Interpretive Standards (μg/ml) for *Staphylococcus* sp.

| Antimicrobial Agent | Susceptible | Intermediate | Resistant |
|---|---|---|---|
| Penicillin | ≦0.12 | — | ≧0.25 |
| Methicillin | ≦8 | — | ≧16 |
| Aminoglycosides | | | |
| Gentamicin | ≦4 | 8 | ≧16 |
| Kanamycin | ≦16 | 32 | ≧64 |
| Macrolides | | | |
| Erythromycin | ≦0.5 | 1-4 | ≧8 |
| Tetracycline | | | |
| Tetracycline | ≦4 | 8 | ≧16 |
| Fluoroquinolone | | | |
| Ciprofloxacin | ≦1 | 2 | ≧4 |
| Folate Pathway Inhibitors | | | |
| Trimethoprim | ≦8 | — | ≧16 |
| Ansamycins | | | |
| Rifampin | ≦1 | 2 | ≧4 |

Example II

Bacterial Methods: NIMELS Treatment Parameters for In Vitro MRSA Experiments

The following parameters illustrate the general bacterial methods according to the invention as applied to MRSA for the in vitro Experiments V and VIII-XII.

A. Experiment Materials and Methods for MRSA:

TABLE 3

Method: for CFU counts

| Time (hrs) | Task | FTE (hrs) |
|---|---|---|
| T −18 | Inoculate overnight culture | 1 |
| | 50 ml directly from glycerol stock | |
| T −4 | Set up starter cultures | 1 |
| | Three dilutions 1:50, 1:125, 1:250 LB Media | |
| | Monitor $OD_{600}$ of starter cultures | 4 |
| T 0 | Preparation of plating culture | 1 |
| | At 10:00 am, the culture which is at $OD_{600}$ = 1.0 | |
| | is diluted 1:300 in PBS (50 mls final volume) and stored | |
| | at RT for 1 hour. (Room temp should be ~25° C.) | |
| T +1 | Seeding of 24-well plates | 1 |
| | 2 ml aliquots are dispensed into pre-designated wells | |
| | in 24-well plates and transferred to NOMIR | |
| T +2 | Dilution of treated samples | 4 |
| to +8 | After laser treatment, 100 μl from each well is | |
| | diluted serially to a final dilution of 1:1000 in PBS. | |
| | Plating of treated samples | 2 |
| | 100 μl of final dilution is plated in quintuplicate (5X) | |
| | on TSB agar with and without antibiotics. | |
| | (10 TSB plates per well) | |
| | Plates are incubated at 37° C. 18-24 hrs. | |
| T +24 | Colonies are counted on each plate | 6 |

Similar cell culture and kinetic protocols were performed for all NIMELS irradiation with *E. coli* and *C. albicans* in vitro tests. Hence, for example, *C. albicans* ATCC 14053 liquid cultures were grown in YM medium (21 g/L, Difco) medium at 37° C. A standardized suspension was aliquoted into selected wells in a 24-well tissue culture plate. Following laser treatments, 100 μL was removed from each well and serially diluted to 1:1000 resulting in a final dilution of 1:5× $10^6$ of initial culture. An aliquot of each final dilution were spread onto separate plates. The plates were then incubated at 37° C. for approximately 16-20 hours. Manual colony counts were performed and recorded.

TABLE 4

Method: for ΔΨ and ROS Assays

| Time (hrs) | Task | FTE (hrs) |
|---|---|---|
| T −18 | Inoculate overnight culture | 1 |
| | 50 ml directly from glycerol stock | |
| T −4 | Set up starter cultures | 1 |
| | Three dilutions 1:50, 1:125, 1:250 LB Media | |
| | Monitor $OD_{600}$ of starter cultures | 4 |
| T 0 | Preparation of plating culture | 1 |
| | At 10:00 am, the culture which is at $OD_{600}$ = 1.0 is | |
| | diluted 1:300 in PBS (50 mls final volume) and stored | |
| | at RT for 1 hour. (Room temp should be ~25° C.) | |
| T +1 | Seeding of 24-well plates for Assays | 1 |
| | 2 ml aliquots are dispensed into pre-designated wells | |
| | in 24-well plates and transferred to NOMIR | |
| T +2 | Dilution of treated samples | 4 |
| to +8 | After laser treatment each control and Lased sample | |
| | were treated as per directions of individual assay. | |

Again, similar cell culture and kinetic protocols were performed for all NIMELS irradiation with *E. coli* and *C. albicans* in vitro assay tests. Hence, for example, *C. albicans* ATCC 14053 liquid cultures were grown in YM medium (21 g/L, Difco) medium at 37° C. A standardized suspension was aliquoted into selected wells in a 24-well tissue culture plate. Following laser treatments each lased and control sample were treated as per directions of individual assay.

Example III

Mammalian Cell Methods: NIMELS Treatment Parameters for In Vitro HEK293 (Human Embryonic Kidney Cell) Experiments The following parameters illustrate the general bacterial methods according to the invention as applied to HEK293 cells for the in vitro experiments.

A. Experiment Materials and Methods for HEK293 Cells.

HEK293 cells were seeded into appropriate wells of a 24-well plate at a density of $1 \times 10^5$ cells/ml (0.7 ml total volume) in Freestyle medium (Invitrogen). Cells were incubated in a humidified incubator at 37° C. in 8% $CO_2$ for approximately 48 hours prior to the experiment. Cells were approximately 90% confluent at the time of the experiment equating to roughly $3 \times 10^5$ total cells. Immediately prior to treatment, cells were washed in pre-warmed phosphate buffer saline (PBS) and overlaid with 2 ml of PBS during treatment.

After laser treatment, cells were mechanically dislodged from the wells and transferred to 1.5 ml centrifuge tubes. Mitochondrial membrane potential and total glutathione was determined according to the kit manufacturer's instructions.

Example IV

NIMELS In Vitro Tests for CRT+(Yellow) and CRT−(White) S. aureus Experiments We conducted experiments with crt− (white) mutants of S. aureus that were genetically engineered with the crt gene (yellow carotenoid pigment) removed, and these mutants were subjected to previously determined non-lethal doses of NIMELS laser against wild type (yellow) S. aureus. The purpose of this experiment was to test for the phenomenon of Radical Oxygen Species (ROS) generation and/or singlet oxygen generation with the NIMELS laser. In the scientific literature, Liu et al. had previously used a similar model, to test the antioxidant protection activity of the yellow S. aureus *caratenoid) pigment against neutrophils. (Liu et al., Staphylococcus aureus golden pigment impairs neutrophil killing and promotes virulence through its antioxidant activity, Vol. 202, No. 2, Jul. 18, 2005 209-215, the entire teaching of which is incorporated herein by reference.)

It has previously been determined that the golden color in S. aureus is imparted by carotenoid (antioxidant) pigments capable of protecting the organism from singlet oxygen, and when a mutant is isolated (crt⁻) that does not produce such carotenoid pigments, the mutant colonies are "white" in appearance and more susceptible to oxidant killing, and have impaired neutrophil survival.

It was found that non-lethal dosimetries of the NIMELS laser (to wild type S. aureus) consistently killed up to 90% of the mutant "white" cells and did not kill the normal S. aureus. The only genetic difference in the two strains of S. aureus is the lack of an antioxidant pigment in the mutant. This experimental data strongly suggests that it is the endogenous generation of radical oxygen species and/or singlet oxygen that are killing the "white" S. aureus.

TABLE 5

Data:
D1-D4 Yellow Wild Type S. aureus.
D5-D6 White "crt−" Mutant S. Aureus.

| Plate No | Output Power (W) | Beam Spot (cm) | Time (sec) | Total Energy Joules | Energy Density (J/cm²) | Power Density (W/cm²) |
|---|---|---|---|---|---|---|
| D1 | 11 | 1.5 | 720 | 7920 | 4481.793 | 6.224712 |
| D2 | 11.5 | 1.5 | 720 | 8280 | 4685.511 | 6.507654 |
| D3 | 12 | 1.5 | 720 | 8640 | 4889.228 | 6.790595 |
| D4 | 12.5 | 1.5 | 720 | 9000 | 5092.946 | 7.073536 |
| D5 | 11 | 1.5 | 720 | 7920 | 4481.793 | 6.224712 |
| D6 | 11.5 | 1.5 | 720 | 8280 | 4685.511 | 6.507654 |
| D7 | 12 | 1.5 | 720 | 8640 | 4889.228 | 6.790595 |
| D8 | 12.5 | 1.5 | 720 | 9000 | 5092.946 | 7.073536 |

Samples D1-D4 Yellow Wild Type S. aureus.
Samples D5-D6 White "crt−" Mutant S. aureus.

TABLE 6

S. Aureus study (ATCC 12600 WT & CRTM−)

| Sample | Control CFU's | Laser-treated CFU' | Percent of Control |
|---|---|---|---|
| D1 | 203 | 44 | 18.48 |
|  | 274 | 55 |  |
|  | 291 | 35 |  |
|  | 241 | 46 |  |
|  | 268 | 56 |  |
| D2 | 270 | 155 | 46.76 |
|  | 303 | 133 |  |
|  | 266 | 110 |  |
|  | 245 | 111 |  |
|  | 321 | 148 |  |
| D3 | 315 | 87 | 25.32 |
|  | 344 | 101 |  |
|  | 310 | 100 |  |
|  | 350 | 71 |  |
|  | 395 | 75 |  |
| D4 | 405 | 23 | 7.21 |
|  | 472 | 31 |  |
|  | 401 | 30 |  |
|  | 403 | 32 |  |
|  | 359 | 31 |  |
| D5 | 530 | 163 | 35.05 |
|  | 534 | 194 |  |
|  | 520 | 192 |  |
|  | 552 | 194 |  |
|  | 520 | 188 |  |
| D6 | 252 | 54 | 20.00 |
|  | 262 | 46 |  |
|  | 248 | 50 |  |
|  | 273 | 70 |  |
|  | 270 | 41 |  |
| D7 | 276 | 40 | 14.68 |
|  | 169 | 30 |  |
|  | 260 | 38 |  |
|  | 259 | 35 |  |
|  | 296 | 42 |  |
| D8 | 323 | 6 | 1.68 |
|  | 348 | 3 |  |
|  | 423 | 9 |  |
|  | 408 | 6 |  |
|  | 340 | 7 |  |

Example V

NIMELS In Vitro Tests for ΔΨ Alteration in MRSA, C. albicans and E. coli

There are selected fluorescent dyes that can be taken up by intact cells and accumulate within the intact cells within 15 to 30 minutes without appreciable staining of other protoplasmic constituents. These dye indicators of membrane potential have been available for many years and have been employed to study cell physiology. The fluorescence intensity of these dyes can be easily monitored, as their spectral fluorescent properties are responsive to changes in the value of the transmembrane potentials $\Delta\Psi$-steady.

These dyes generally operate by a potential-dependent partitioning between the extracellular medium and either the membrane or the cytoplasm of membranes. This occurs by redistribution of the dye via interaction of the voltage potential with an ionic charge on the dye. This fluorescence can be eliminated in about 5 minutes by the protonophore carbonyl cyanide m-chlorophenylhydrazone (CCCP), indicating that maintenance of dye concentration is dependent on the inside-negative transmembrane potential maintained by functional ETS and $\Delta p$.

Hypothesis Testing:

The null hypothesis is $\mu_1 - \mu_2 = 0$:

$\mu_1$ is fluorescence intensity in a control cell culture (no laser) subjected to carbocyanine dye.

$\mu_2$ is fluorescence intensity in the same cell culture pre-irradiated with sub-lethal dosimetry from the NIMELS laser The data indicates that the fluorescence of cells is dissipated (less than control of unirradiated or "unlased" cells) by pre-treatment (of the cells) with the NIMELS laser system, indicating that the NIMELS laser interacted with respiratory processes and oxidative phosphorylation of the cells via the plasma membranes.

$$\mu_1 - \mu_2 = 0$$

Will uphold that the addition sub-lethal NIMEL irradiation on the cell culture has no effect on $\Delta\Psi$-steady.

$$\mu_1 - \mu_2 > 0$$

Will uphold that the addition sub-lethal NIMEL irradiation on the cell culture has a dissipation or depolarization effect on $\Delta\Psi$-steady.

Materials and Methods:

BacLight™ Bacterial Membrane Potential Kit (B34950, Invitrogen U.S.). The BacLight™ Bacterial Membrane Potential Kit provides of carbocyanine dye DiOC2(3) (3,3'-diethyloxacarbocyanine iodide, Component A) and CCCP (carbonyl cyanide 3-chlorophenylhydrazone, Component B), both in DMSO, and a 1×PBS solution (Component C).

DiOC2(3) exhibits green fluorescence in all bacterial cells, but the fluorescence shifts toward red emission as the dye molecules self associate at the higher cytosolic concentrations caused by larger membrane potentials. Proton ionophores such as CCCP destroy membrane potential by eliminating the proton gradient, hence causing higher green fluorescence.

Detection of Membrane Potential $\Delta\Psi$ in MRSA

Green fluorescence emission was calculated using population mean fluorescence intensities for control and lased samples at sub-lethal dosimetry:

TABLE 6

| MRSA Dosimetry Progression First lasing procedure: Both 870 and 930 Second lasing procedure 930 alone | | | |
|---|---|---|---|
| Parameters | Output Power (W) | Beam Spot (cm) | Area of Spot (cm2) | Time (sec) |
| 870 at 4.25 W and 930 at 4.25 W for 16 min followed by | 8.5 | 1.5 | 1.77 | 960 |
| 930 at 8.5 W for 7 min | 8.5 | 1.5 | 1.77 | 420 |

Figure 8:
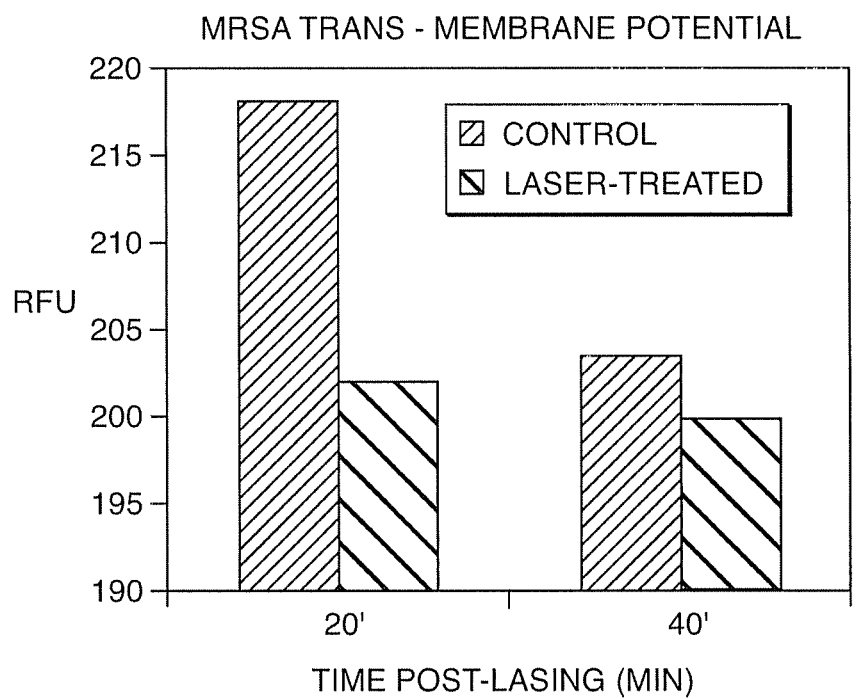
FIG. 8 shows the effects of NIMELS irradiation (at a single dosimetry) on MRSA trans-membrane potential which is measured by green fluorescence emission intensities in control and lased samples as a function of time in minutes post-lasing.

The data shows that $\mu_1 - \mu_2 > 0$ as the lased cells had less "Green fluorescence" as seen in FIG. 8. These MRSA samples showed clear alteration and lowering of $\Delta\Psi$-steady-bact to one of $\Delta\Psi$-trans-bact with sub-lethal NIMELS dosimetry.

Detection of Membrane Potential $\Delta\Psi$ in C. albicans

Green fluorescence emission was calculated using population mean fluorescence intensities for control and lased samples at sub-lethal dosimetry listed in the table below:

TABLE 7

| First lasing procedure: Both 870 and 930 Second lasing procedure 930 alone | | | | |
|---|---|---|---|---|
| Parameters | Output Power (W) | Beam Spot (cm) | Area of Spot (cm2) | Time (sec) |
| Laser #1 | | | | |
| Test (H-1) 870 at 4 W and 930 at 4 W for 18 min followed by | 8.0 | 1.5 | 1.77 | 1080 |
| Test (H-1) 930 at 8 W for 8 min | 8.0 | 1.5 | 1.77 | 480 |
| Laser #2 | | | | |
| Test (H-2) 870 at 4.25 W and 930 at 4.25 W for 18 min followed by | 8.5 | 1.5 | 1.77 | 1080 |
| Test (H-2) 930 at 8.5 W for 8 min | 8.5 | 1.5 | 1.77 | 480 |
| Laser #3 | | | | |
| Test (H-3) 870 at 4 W and 930 at 4 W for 20 min followed by | 8.0 | 1.5 | 1.77 | 1200 |
| Test (H-3) 930 at 8 W for 10 min | 8.0 | 1.5 | 1.77 | 600 |

Figure 9:
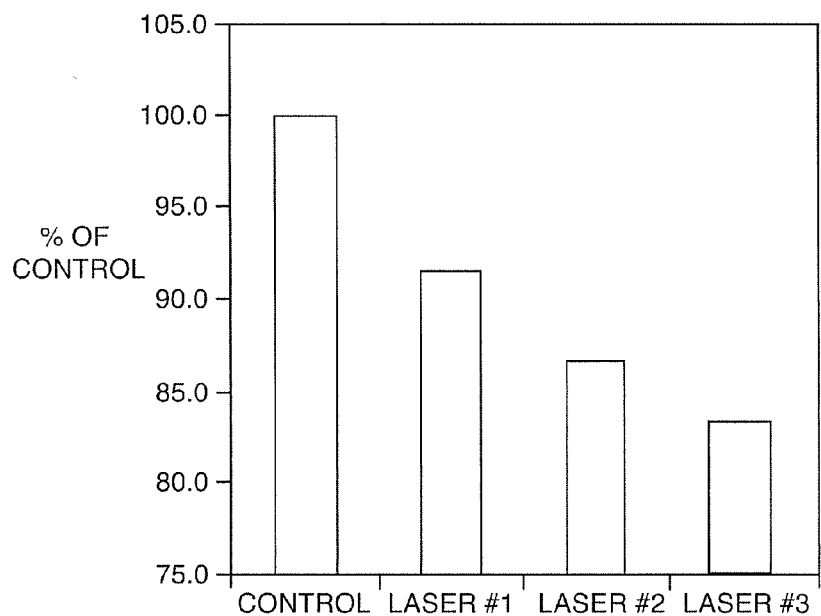
FIG. 9 shows the effects of NIMELS irradiation (at various dosimetries) on *C. albicans* trans-membrane potential which is measured by percent drop in green fluorescence emission intensities in lased samples relative to the control.

The data shows that $\mu_1-\mu_2>0$ as the lased *C. albicans* cells had less "Green fluorescence" as seen in FIG. 9. These *C. albicans* samples showed clear alteration and lowering of $\Delta\Psi$-steady-fungi to one of $\Delta\Psi$-trans-fungi with sub-lethal NIMELS dosimetry with increasing (sub-lethal) NIMELS laser dosimetry.

Detection of Membrane Potential $\Delta\Psi$ in *E. coli*

Figure 19:
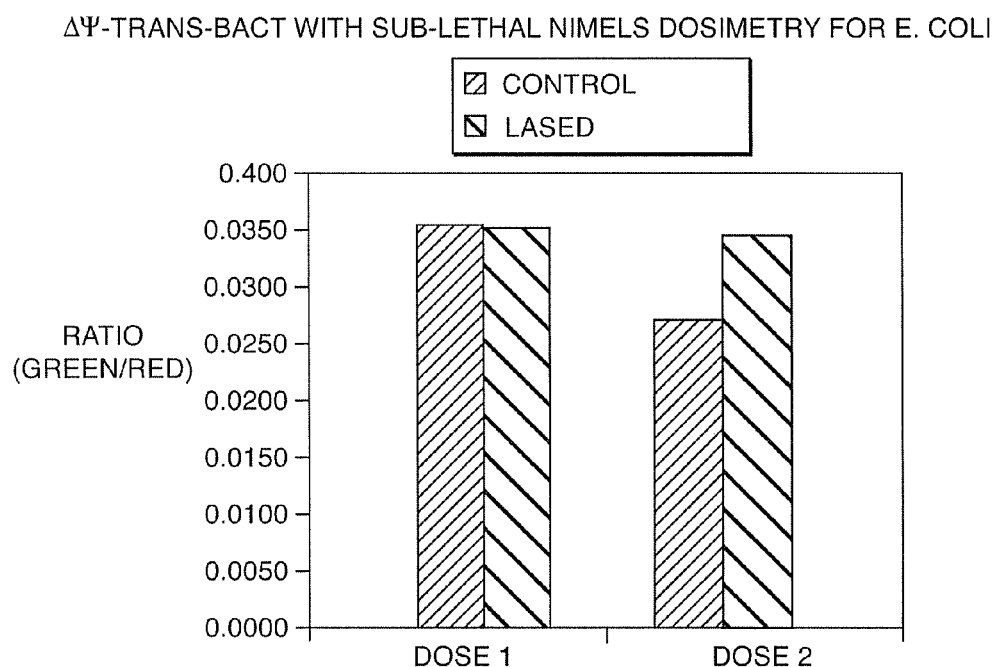
FIG. 19 illustrates the detection of decreased membrane potential in *E. coli* with sub-lethal NIMELS irradiation.

Red/green ratios were calculated using population mean fluorescence intensities for control and lased samples at sub-lethal dosimetry:

The data shows that $\mu_1-\mu_2>0$ as the lased cells had less "Green fluorescence" as seen in FIG. 19. These *E. coli* samples showed clear alteration and lowering of $\Delta\Psi$-steady-bact to one of $\Delta\Psi$-trans-bact with sublethal NIMELS dosimetry.

Example VI

NIMELS In Vitro Tests for $\Delta\Psi$-Mito in *C. albicans* with Sub-Lethal Laser Dosimetry Hypothesis Testing:
The null hypothesis is $\mu_1-\mu_2=0$:
a) $\mu_1$ is fluorescence intensity in a control cell culture mitochondria subjected to a Mitochondrial Membrane Potential Detection Kit.
b) $\mu_2$ is fluorescence intensity in the same cell culture pre-irradiated with sub-lethal dosimetry from the NIMELS laser and subjected to a Mitochondrial Membrane Potential Detection Kit.

The data shows that the fluorescence of mitochondria is dissipated (less than control unlased cells) by pre-treatment (of the cells) with the NIMELS laser system, the results indicate that the NIMELS laser interacted with respiratory processes and oxidative phosphorylation of the cells in mitochondria of fungal and mammalian cells.

$\mu_1-\mu_2=0$

Will uphold that the addition sub-lethal NIMEL irradiation on the cell culture mitochondria has no effect on $\Delta\Psi$-steady-mito.

$\mu_1-\mu_2>0$

Will uphold that the addition sub-lethal NIMEL irradiation on the cell culture has a dissipation or depolarization effect on $\Delta\Psi$-steady-mito.

Materials and Methods:
Mitochondrial Membrane Potential Detection Kit (APO LOGIX JC-1) (Cell Technology Inc., 950 Rengstorff Ave, Suite D; Mountain View Calif. 94043).

The loss of mitochondrial membrane potential ($\Delta\Psi$) is a hallmark for apoptosis. The APO LOGIX JC-1 Assay Kit measures the mitochondrial membrane potential in cells.

In non-apoptotic cells, JC-1 (5,5',6,6'-tetrachloro-1,1',3,3'-tetraethylbenz-imidazolylcarbocyanine iodide) exists as a monomer in the cytosol (green) and also accumulates as aggregates in the mitochondria which stain red. Whereas, in apoptotic and necrotic cells, JC-1 exists in monomeric form and stains the cytosol green.

TABLE 8

*Candida Albicans* Dosimetry Table
First lasing procedure: Both 870 and 930
Second lasing procedure 930 alone

| Test | Parameters | Output Power (W) | Beam Spot (cm) | Area of Spot (cm2) | Time (sec) |
|---|---|---|---|---|---|
| Cand Mito 1 | Test (H-3) 870 at 4.25 W and 930 at 4.25 W for 16 min followed by | 8.5 | 1.5 | 1.77 | 960 |
| | Test (H-3) 930 at 8.5 W for 10 min | 8.5 | 1.5 | 1.77 | 600 |

The (APO LOGIX JC-1) kit measures membrane potential by conversion of green fluorescence to red fluorescence. In FIG. 10A, the appearance of red color has been measured and plotted, which should only occur in cells with intact membranes, and the ratio of green to red is shown in FIG. 10B for both control and lased samples.

Clearly in this test, the red fluorescence is reduced in the lased sample while the ratio of green to red increases, indicating depolarization. These results are the same as the transmembrane $\Delta\Psi$ tests (i.e., both data show depolarization).

These results also show that $\mu_1-\mu_2>0$ and that sub-lethal NIMEL irradiation on the cell mitochondria has a dissipation or depolarization effect on $\Delta\Psi$-steady-mito, indicating a clear reduction of *Candida Albicans* $\Delta\Psi$-steady-mito-fungi to $\Delta\Psi$-trans-mito-fungi.

Example VII

NIMELS In Vitro Tests for $\Delta\Psi$-Mito Human Embryonic Kidney Cells with Sub-Lethal Laser Dosimetry Hypothesis Testing:
The null hypothesis is $\mu_1-\mu_2=0$:
a) $\mu_1$ is fluorescence intensity in a mammalian control cell culture mitochondria (no laser) subjected to a Mitochondrial Membrane Potential Detection Kit.
b) $\mu_2$ is fluorescence intensity in the same mammalian cell culture pre-irradiated with sub-lethal dosimetry from the NIMELS laser and subjected to a Mitochondrial Membrane Potential Detection Kit.

The data shows that the fluorescence of mitochondria is dissipated (less than control unlased cells) by pre-treatment (of the cells) with the NIMELS laser system, the results indicate that the NIMELS laser interacted with respiratory processes and oxidative phosphorylation of the cells in mitochondria of mammalian cells.

$\mu_1-\mu_2=0$

Will uphold that the addition sub-lethal NIMEL irradiation on the mammalian cell culture mitochondria has no effect on $\Delta\Psi$-steady-mito-mam.

$\mu_1-\mu_2>0$

Will uphold that the addition sub-lethal NIMEL irradiation on the mammalian cell culture has a dissipation or depolarization effect on $\Delta\Psi$-steady-mito-mam.

Materials and Methods:
Mitochondrial Membrane Potential Detection Kit (APO LOGIX JC-1) (Cell Technology Inc., 950 Rengstorff Ave, Suite D; Mountain View Calif. 94043). The loss of mitochondrial membrane potential ($\Delta\Psi$) is a hallmark for apoptosis. The APO LOGIX JC-1 Assay Kit measures the mitochondrial membrane potential in cells.

In non-apoptotic cells, JC-1 (5,5',6,6'-tetrachloro-1,1',3,3'-tetraethylbenz-imidazolylcarbocyanine iodide) exists as a monomer in the cytosol (green) and also accumulates as aggregates in the mitochondria which stain red. Whereas, in apoptotic and necrotic cells, JC-1 exists in monomeric form and stains the cytosol green.

TABLE 9

Mamallian Cell Dosimetries
First lasing procedure: Both 870 and 930
Second lasing procedure 930 alone

| Parameters | Output Power (W) | Beam Spot (cm) | Area of Spot (cm2) | Time (sec) |
|---|---|---|---|---|
| Test (H-2) 870 at 4.25 W and 930 at 4.25 W for 18 min followed by | 8.5 | 1.5 | 1.77 | 1080 |
| Test (H-2) 930 at 8.5 W for 10 min | 8.5 | 1.5 | 1.77 | 600 |

Figure 11A:
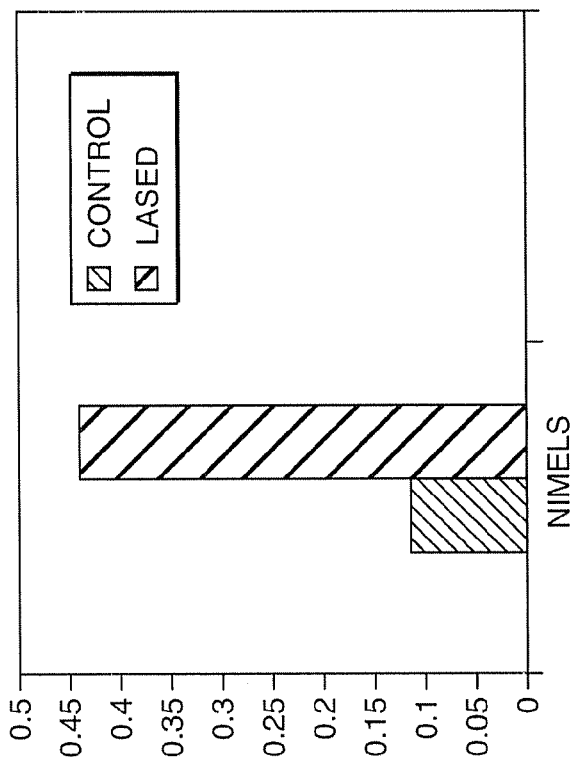
FIG. 11 shows the effects of NIMELS irradiation (at a single dosimetry) on mitochondrial membrane potential of human embryonic kidney cells, which is measured by red fluorescence emission intensities in control and lased samples; and the effects of NIMELS irradiation (at a single dosimetry) on mitochondrial membrane potential of human embryonic kidney cells, which is measured as ratio of red to green fluorescence in control and lased samples.
Figure 11B:
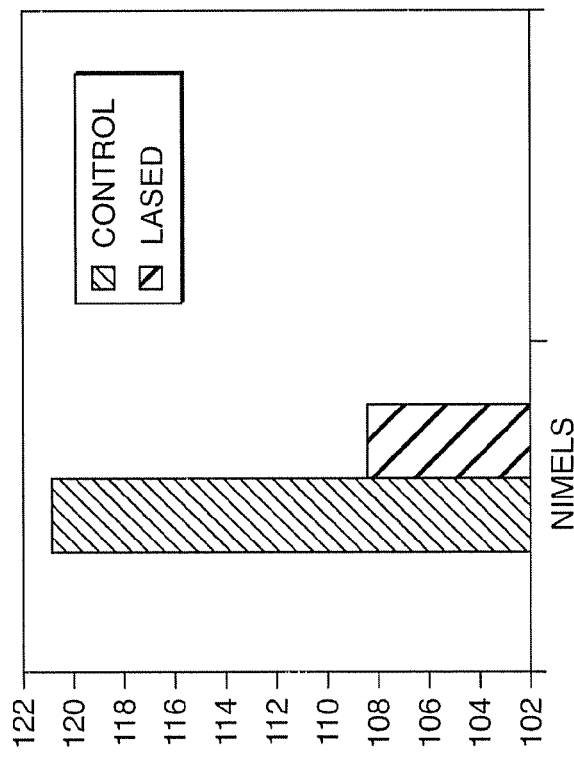

HEK-293 (Human Embryonic Kidney Cells) $\Delta\Psi$-mito tests:

The (APO LOGIX JC-1) kit measures membrane potential by conversion of green fluorescence to red fluorescence. In FIG. 11A, the appearance of red color has been measured and plotted, which should only occur in cells with intact membranes, and the ratio of green to red is shown in FIG. 11B for both control and lased samples.

Clearly in this test, the red fluorescence is reduced in the lased sample while the ratio of green to red increases, indicating depolarization. These results show that $\mu_1 - \mu_2 > 0$ and that sub-lethal NIMELS irradiation on the mammalian cell mitochondria has a dissipation or depolarization effect on $\Delta\Psi$-steady-mito-mam, indicating a clear reduction in mammalian $\Delta\Psi$-steady-mito-mam to $\Delta\Psi$-trans-mito-mam.

Example VIII

NIMELS In Vitro Tests for Reactive Oxygen Species (ROS)

These in vitro tests for generation of reactive oxygen species (ROS) were carried on after laser alteration of bacterial trans-membrane $\Delta\Psi$-steady-bact to $\Delta\Psi$-trans-bact, $\Delta\Psi$-steady-mito-fungi to $\Delta\Psi$-trans-mito-fungi, and $\Delta\Psi$-steady-mito-mam to $\Delta\Psi$-trans-mito-mam with sub-lethal laser dosimetry comparable to those used in $\Delta\Psi$ tests above in previous examples.

Materials and Methods:

Total Glutathione Quantification Kit (Dojindo Laboratories; Kumamoto Techno Research Park, 2025-5 Tabaru, Mashiki-machi, Kamimashiki-gun; Kumamoto 861-2202, JAPAN)

Glutathione (GSH) is the most abundant thiol (SH) compound in animal tissues, plant tissues, bacteria and yeast. GSH plays many different roles such as protection against reactive oxygen species and maintenance of protein SH groups. During these reactions, GSH is converted into glutathione disulfide (GSSG: oxidized form of GSH). Since GSSG is enzymatically reduced by glutathione reductase, GSH is the dominant form in organisms. DTNB (5,5'-Dithio-bis(2-nitrobenzoic acid)), known as Ellman's Reagent, was developed for the detection of thiol compounds. In 1985, it was suggested that the glutathione recycling system by DTNB and glutathione reductase created a highly sensitive glutathione detection method. DTNB and glutathione (GSH) react to generate 2-nitro-5-thiobenzoic acid and glutathione disulfide (GSSG). Since 2-nitro-5-thiobenzoic acid is a yellow colored product, GSH concentration in a sample solution can be determined by the measurement at 412 nm absorbance. GSH is generated from GSSG by glutathione reductase, and reacts with DTNB again to produce 2-nitro-5-thiobenzoic acid. Therefore, this recycling reaction improves the sensitivity of total glutathione detection.

At significant concentrations ROS will react rapidly and specifically with the target at a rate exceeding the rate of its reduction by the components of the glutathione antioxidant system (catalases, peroxidases, GSH).

Figure 12:
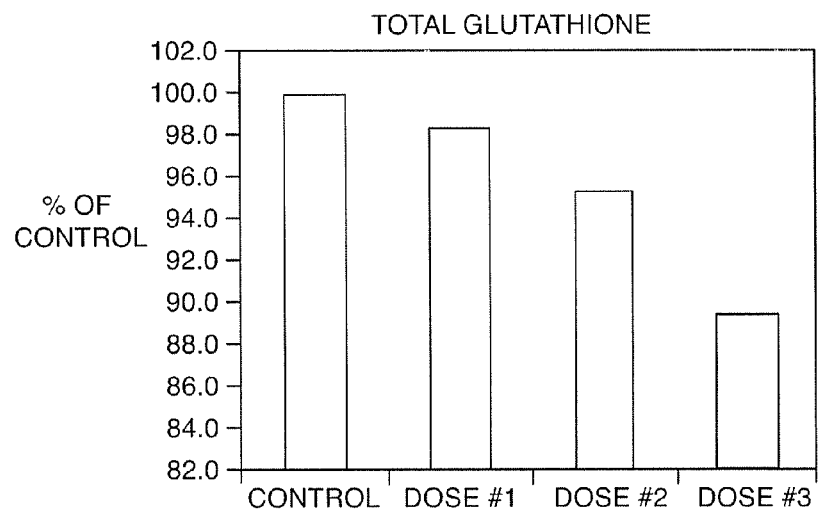
FIG. 12 shows the reduction in total glutathione concentration in MRSA as it correlates with reactive oxygen species (ROS) generation in these cells as the result of NIMELS irradiation (at several dosimetries); the decrease in glutathione concentration in lased samples is shown as percentage relative to the control.

Detection of Glutathione in MRSA at Sub-Lethal NIMELS Dosimetry that Alters $\Delta\Psi$-Steady-Bact to One of $\Delta\Psi$-Trans-Bact The results as shown in FIG. 12 clearly show a reduction in total glutathione in MRSA at sub-lethal NIMELS dosimetry that alters that alters $\Delta\Psi$-steady-bact to one of $\_\Delta\Psi$-trans-bact, which is a proof of generation of ROS with sub-lethal alteration of Trans-membrane $\Delta\Psi$-steady-bact to one of $\Delta\Psi$-trans-bact.

Figure 20:
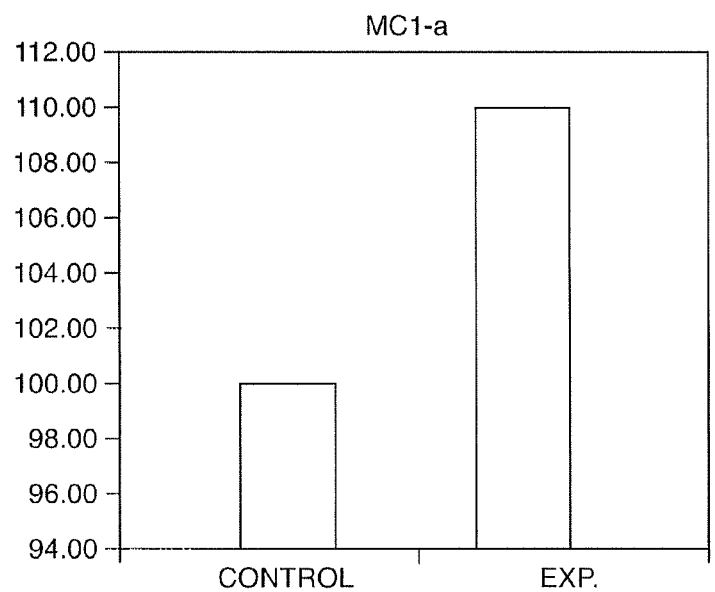
FIG. 20 illustrates the detection of increased glutathione in *E. coli* with sub-lethal NIMELS irradiation.

Detection of Glutathione in *E. coli* at Sub-Lethal NIMELS Dosimetry that Alters Trans-Membrane $\Delta\Psi$-Steady to One of $\Delta\Psi$-Trans The results as shown in FIG. 20 clearly shows a reduction in total glutathione in *E. coli* at sub-lethal NIMELS dosimetry that alters $\Delta\Psi$-steady-bact to one of $\Delta\Psi$-trans-bact, which is evidence of generation of ROS with sub-lethal alteration of Trans-membrane $\Delta\Psi$-steady-bact to one of $\Delta\Psi$-trans-bact.

Detection of glutathione in *C. albicans* at sub-lethal NIMELS that alters $\Delta\Psi$-steady-mito-fungi to $\Delta\Psi$-trans-mito-fungi and subsequently $\Delta\Psi$-steady-fungi to one of $\Delta\Psi$-trans-fungi.

Figure 13:
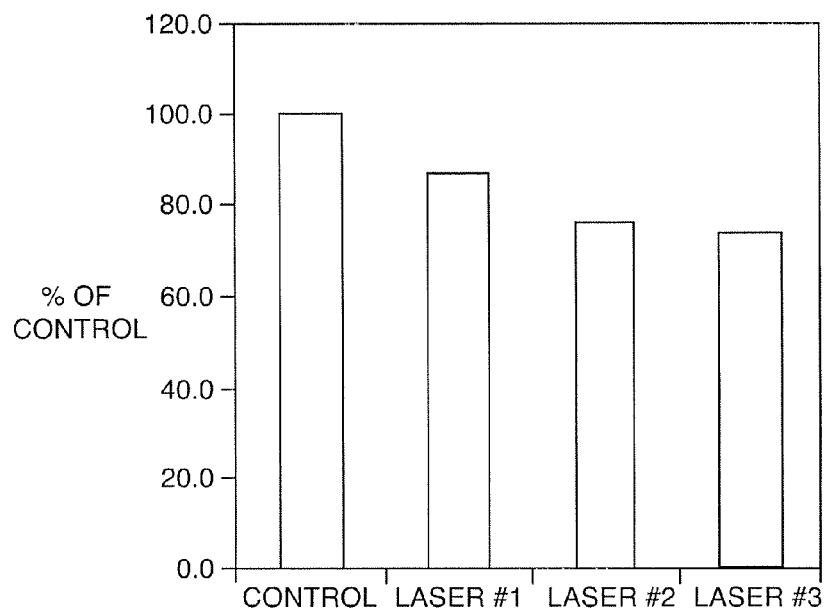
FIG. 13 shows the reduction in total glutathione concentration in *C. albicans* as it correlates with reactive oxygen species (ROS) generation in these cells as the result of NIMELS irradiation (at several dosimetries); the decrease in glutathione concentration in lased samples is shown as percentage relative to the control.

Detection of Glutathione in *C. albicans* at Sub-Lethal NIMELS Dosimetry that Alters $\Delta\Psi$-Steady-Mito-Fungi to $\Delta\Psi$-Trans-Mito-Fungi and Subsequently $\Delta\Psi$-Steady-Fungi to One of $\Delta\Psi$-Trans-Fungi The results as shown in FIG. 13 clearly show a reduction in total glutathione in *C. albicans* at sub-lethal NIMELS dosimetry that alters $\Delta\Psi$-steady-mito-fungi to $\Delta\Psi$-trans-mito-fungi and subsequently $\Delta\Psi$-steady-fungi to one of $\Delta\Psi$-trans-fungi, which is a proof of generation of ROS with sub-lethal alteration of Trans-membrane $\Delta\Psi$-steady-mito-fungi to $\Delta\Psi$-trans-mito-fungi and subsequently $\Delta\Psi$-steady-fungi to one of $\Delta\Psi$-trans-fungi.

Figure 14:
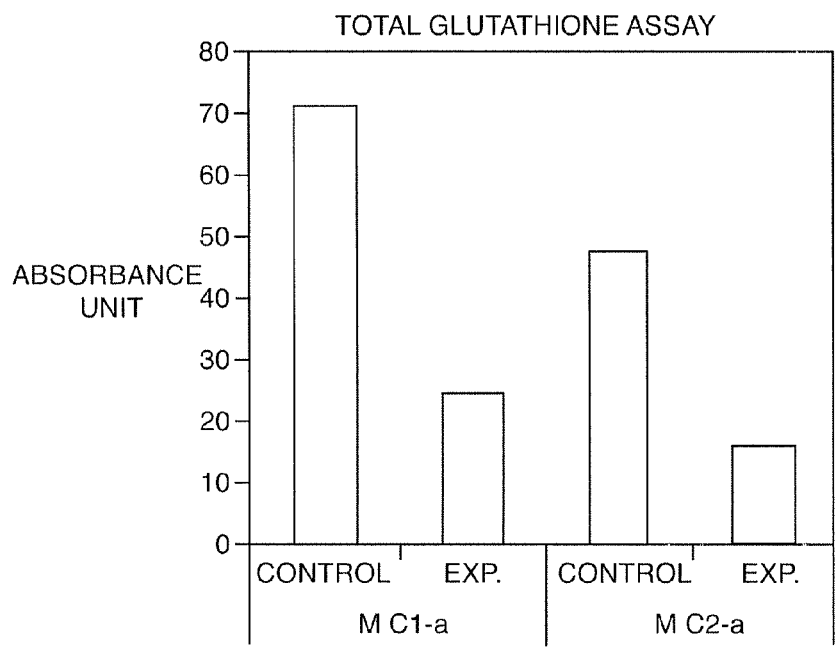
FIG. 14 shows the reduction in total glutathione concentration in human embryonic kidney cells as it correlates with reactive oxygen species (ROS) generation in these cells as the result of NIMELS irradiation (at two different dosimetries); the decrease in glutathione concentration in lased samples is shown as percentage relative to the control.

Detection of Glutathione in HEK-293 (Human Embryonic Kidney Cells) at Sub-Lethal NIMELS Dosimetry that Alters $\Delta\Psi$-Steady-Mito-Mam to $\Delta\Psi$-Trans-Mito-Mam The results as shown in FIG. 14 clearly show a reduction in total Glutathione in HEK-293 (Human Embryonic Kidney Cells) with sub-lethal NIMELS dosimetry that alters $\Delta\Psi$-steady-mito-mam to $\Delta\Psi$-trans-mito-mam, which is proof of generation of ROS with NIMELS-mediated sub-lethal alteration of Trans-membrane $\Delta\Psi$-steady-mito-mam to $\Delta\Psi$-trans-mito-mam.

Example IX

Assessment of the Impact of Sub-Lethal Doses of NIMELS Laser on MRSA with Erythromycin and Trimethoprim In this example, it was determined whether a sub-lethal dose of the NIMEL laser will potentiate the effect of the antibiotic erythromycin more than the antibiotic trimethoprim in MRSA. Efflux pumps play a major factor in erythromycin resistance. There are no reported trimethoprim efflux pump resistance mechanisms in the gram positive *S. aureus*.

Background: Erythromycin is a marcolide antibiotic that has an antibacterial spectrum of action very similar to that of the β-lactam penicillin. In the past, it has been effective in the treatment of a wide range of gram-positive bacterial infections effecting the skin and respiratory tract, and has been considered one of the safest antibiotics to use. In the past, erythromycin has been used for people with allergies to penicillins.

Erythromycin's mechanism of action is to prevent growth and replication of bacteria by obstructing bacterial protein synthesis. This is accomplished because erythromycin binds to the 23 S rRNA molecule in the 50 S of the bacterial ribosome, thereby blocking the exit of the growing peptide chain thus inhibiting the translocation of peptides. Erythromycin resistance (as with other marcolides) is rampant, wide spread, and is accomplished via two significant resistance systems:
A) modification of the 23 S rRNA in the 50 S ribosomal subunit to insensitivity
B) efflux of the drug out of cells Trimethoprim is an antibiotic that has historically been used in the treatment of urinary tract infections. It is a member of the class of antimicrobials known as dihydrofolate reductase inhibitors. Trimethoprim's mechanism of action is to interfere with the system of bacterial dihydrofolate reductase (DHFR), because it is an analog of dihydrofolic acid. This causes competitive inhibition of DHFR due to a 1000 fold higher affinity for the enzyme than the natural substrate.

Thus, trimethoprim inhibits synthesis of the molecule tetrahydrofolic acid. Tetrahydrofolic acid is an essential precursor in the de novo synthesis of the DNA nucleotide thymidylate. Bacteria are incapable of taking up folic acid from the environment (i.e., the infection host) and are thus dependent on their own de novo synthesis of tetrahydrofolic acid. Inhibition of the enzyme ultimately prevents DNA replication.

Trimethoprim resistance generally results from the overproduction of the normal chromosomal DHFR, or drug resistant DHFR enzymes. Reports of trimethoprim resistance *S. aureus* have indicated that the resistance is chromosomally of the mediated type or is encoded on large plasmids. Some strains have been reported to exhibit both chromosomal and plasmid-mediated trimethoprim resistance.

In the gram positive pathogen *S. aureus*, resistance to trimethoprim is due to genetic mutation, and there have been no reports that trimethoprim is actively effluxed out of cells.

Efflux Pumps in Bacteria

A major route of drug resistance in bacteria and fungi is the active export (efflux) of antibiotics out of the cells such that a therapeutic concentration in not obtained in the cytoplasm of the cell.

Active efflux of antibiotics (and other deleterious molecules) is mediated by a series of transmembrane proteins in the cytoplasmic membrane of gram positive bacteria and the outer membranes of gram negative bacteria.

Clinically, antibiotic resistance that is mediated via efflux pumps, is most relevant in gram positive bacteria for marcolides, tetracyclines and fluoroquinolones. In gram negative bacteria, β-lactam efflux mediated resistance is also of high clinical relevance.

Hypothesis Testing

The null hypothesis is $\mu_1 - \mu_2 = 0$ and $\mu_1 - \mu_3 = 0$ where:
a) $\mu_1$ is sub-lethal dosimetry from the NIMEL laser system on MRSA as a control and;
b) $\mu_2$ is the same sub-lethal dosimetry from the NIMEL laser system on MRSA with the addition of trimethoprim at resistant MIC just below effectiveness level and;
c) $\mu_3$ is the same sub-lethal dosimetry from the NIMEL laser system on MRSA with the addition of erythromycin at resistant MIC just below effectiveness level.

The data shows that the addition of the antibiotic trimethoprim or erythromycin, after sub-lethal irradiation, results in the reduction in growth of these MRSA colonies, as follows:

$\mu_1 - \mu_2 = 0$

Will uphold that the addition of trimethoprim produces no deleterious effect after sub-lethal NIMEL irradiation, on normal growth of MRSA colonies.

$\mu_1 - \mu_2 > 0$

Will uphold that the addition of trimethoprim produces a deleterious effect after sub-lethal NIMEL irradiation, on normal growth of MRSA colonies.

$\mu_1 - \mu_3 = 0$

Will uphold that the addition of erythromycin produces no deleterious effect after sub-lethal NIMEL irradiation, on normal growth of MRSA colonies.

$\mu_1 - \mu_3 > 0$

Will uphold that the addition of erythromycin produces a deleterious effect after sub-lethal NIMEL irradiation, on normal growth of MRSA colonies.

TABLE 10

| EXPERIMENTAL | | | | CONTROL (no laser) | | |
|---|---|---|---|---|---|---|
| | AGAR | trimeth 2 ug/ml | erythro 4 ug/ml | | AGAR | trimeth 2 ug/ml | erythro 4 ug/ml |
| B-4 1 | 84 | 110 | 39 | B-4 1 | 180 | 213 | 196 |
| B-4 2 | 88 | 125 | 35 | B-4 2 | 230 | 198 | 168 |
| B-4 3 | 120 | 138 | 39 | B-4 3 | 241 | 240 | 175 |
| B-4 4 | 114 | 115 | 28 | B-4 4 | 220 | 220 | 177 |
| B-4 5 | 117 | 100 | 27 | B-4 5 | smeared | 145 | 195 |

Results:

This experiment clearly showed that under sub-lethal laser parameters with the NIMELS system, $\mu_1 - \mu_2 = 0$ and $\mu_1 - \mu_3 \geq 0$. This indicates that an efflux pump is being inhibited, and resistance to erythromycin being reversed by the NIMELS effect on $\Delta\Psi$-steady-bact of the MRSA.

Example X

Assessment of the Impact of Sub-Lethal Doses of NIMELS Laser on MRSA with Tetracycline and Rifampin The purpose of this experiment was to observe if a sub-lethal dose of the NIMEL laser will potentiate the effect of the antibiotic tetracycline more than the antibiotic rifampin in MRSA. Efflux pumps are well researched, and play a major factor in tetracycline resistance. However, there are no reported rifampin efflux pump resistance mechanisms in the gram positive *S. aureus*.

This experiment was also previously run with erythromycin and trimethoprim, with data indicating that the NIMELS effect is able to damage efflux pump resistance mechanisms in erythromycin.

Tetracycline:

Tetracycline is considered a bacteriostatic antibiotic, meaning that it hampers the growth of bacteria by inhibiting protein synthesis. Tetracycline accomplishes this by inhibiting action of the bacterial 30 S ribosome through the binding of the enzyme aminoacyl-tRNA. Tetracycline resistance is often due to the acquisition of new genes, which code for energy-dependent efflux of tetracyclines, or for a protein that protects bacterial ribosomes from the action of tetracyclines.

Rifampin:

Rifampin is a bacterial RNA polymerase inhibitor, and functions by directly blocking the elongation of RNA. Rifampicin is typically used to treat mycobacterial infections, but also plays a role in the treatment of methicillin-resistant *Staphylococcus aureus* (MRSA) in combination with fusidic acid, a bacteriostatic protein synthesis inhibitor. There are no reports of rifampin resistance via efflux pumps in MRSA.

Hypothesis:

The null hypothesis is $\mu_1-\mu_2=0$ and $\mu_1-\mu_3=0$ where:

a) $\mu_1$ is sub-lethal dosimetry from the NIMEL laser system on MRSA as a control and;
b) μ2 is the same sub-lethal dosimetry from the NIMEL laser system on MRSA with the addition of tetracycline at resistant MIC just below effectiveness level and;
c) $\mu_3$ is the same sub-lethal dosimetry from the NIMEL laser system on MRSA with the addition of rifampin at resistant MIC just below effectiveness level.

The data shows that the addition of the antibiotic tetracycline or rifampin, after sub-lethal irradiation, results in the reduction in growth of these MRSA colonies, as follows:

$\mu_1-\mu_2=0$

Will uphold that the addition of tetracycline produces no deleterious effect after sub-lethal NIMEL irradiation, on normal growth of MRSA colonies.

$\mu_1-\mu_2>0$

Will uphold that the addition of tetracycline produces a deleterious effect after sub-lethal NIMEL irradiation, on normal growth of MRSA colonies.

$\mu_1-\mu_3=0$

Will uphold that the addition of rifampin produces no deleterious effect after sub-lethal NIMEL irradiation, on normal growth of MRSA colonies.

$\mu_1-\mu_3>0$

Will uphold that the addition of rifampin produces a deleterious effect after sub-lethal NIMEL irradiation, on normal growth of MRSA colonies.

Results:

This experiment clearly showed that under sub-lethal laser parameters with the NIMELS system, $\mu_1-\mu_2=0$ and $\mu_1-\mu_3>=0$. This indicates that an efflux pump is being inhibited, and resistance to tetracycline is being reversed by the NIMELS effect on $\Delta\Psi$-steady-bact of the MRSA.

Example XI

Assessment of the Impact of Sub-Lethal Doses of NIMELS Laser on MRSA with Methicillin and $\Delta\Psi$-Plas-Bact Inhibition of Cell Wall Synthesis Methicillin:

Methicillin is a β-lactam that was previously used to treat infections caused by gram-positive bacteria, particularly β-lactamase-producing organisms such as *S. aureus* that would otherwise be resistant to most penicillins, but is no longer clinically used. The term methicillin-resistant *S. aureus* (MRSA) continues to be used to describe *S. aureus* strains resistant to all penicillins.

Mechanism of Action

Like other β-lactam antibiotics, methicillin acts by inhibiting the synthesis of peptidoglycan (bacterial cell walls).

It has been shown in the gram positive bacterium *Bacillus subtilis*, that the activities of peptidoglycan autolysins are increased (i.e., no longer inhibited) when the ETS was blocked by adding proton conductors. This suggests that $\Delta\Psi$-plas-bact and $\Delta\mu H^+$ (independent of storing energy for cellular enzymatic functions) potentially has a profound and exploitable influence on cell wall anabolic functions and physiology.

In addition, it has been reported that $\Delta\Psi$-plas-bact uncouplers inhibit peptidoglycan formation with the accumulation of the nucleotide precursors involved in peptidoglycan synthesis, and the inhibition of transport of N-acetylglucosamine (GlcNAc), one of the major biopolymers in peptidoglycan.

Hypothesis Testing:

Bacitracin will potentiate the multiple influences of an optically lowered $\Delta\Psi$-plas-bact on a growing cell wall (i.e., increased cell wall autolysis, inhibited cell wall synthesis). This is especially relevant in gram positive bacteria such as MRSA, that do not have efflux pumps as resistance mechanisms for cell wall inhibitory antimicrobial compounds.

TABLE 11

| | EXPERIMENTAL | | | | CONTROL | | |
| --- | --- | --- | --- | --- | --- | --- | --- |
| | AGAR | rifampin 90 ug/ml | tetracyc. 4 ug/ml | | AGAR | rifampin 90 ug/ml | tetracyc. 4 ug/ml |
| E1-1 | 307 | 210 | 42 | E1-1 | 270 | 183 | 240 |
| E1-2 | 300 | 200 | 56 | E1-2 | 210 | 210 | 256 |
| E1-3 | 300 | 280 | 46 | E1-3 | 224 | 166 | 268 |
| E1-4 | 310 | 378 | 48 | E1-4 | semared | 228 | 310 |
| E1-5 | 250 | 280 | 42 | E1-5 | 215 | 188 | 255 |
| E2-1 | 246 | 272 | 18 | E2-1 | 240 | 274 | 280 |
| E2-2 | 254 | 320 | 28 | E2-2 | 310 | 210 | 283 |
| E2-3 | 174 | 330 | 27 | E2-3 | 190 | 180 | 263 |
| E2-4 | 170 | semared | 16 | E2-4 | 257 | 240 | 260 |
| E2-5 | 240 | 284 | 18 | E2-5 | 275 | | 310 |
| E3-1 | 310 | 270 | 72 | E3-1 | 280 | 288 | 368 |
| E3-2 | 280 | 225 | 67 | E3-2 | 320 | 280 | 380 |
| E3-3 | 260 | 284 | 45 | E3-3 | 310 | 210 | 375 |
| E3-4 | 210 | 200 | 47 | E3-4 | 320 | 290 | 390 |
| E3-5 | 220 | smeared | 74 | E3-5 | 320 | 300 | smeared |

The null hypothesis is $\mu_1-\mu_2=0$ and $\mu_1-\mu_3=0$ where:
a) $\mu_1$ is sub-lethal dosimetry from the NIMEL laser system on MRSA as a control and;
b) $\mu_2$ is the same sub-lethal dosimetry from the NIMEL laser system on MRSA with the addition of methicillin at resistant MIC just below effectiveness level and;

$$\mu_1-\mu_2=0$$

Will uphold that the addition of methicillin produces no deleterious effect after sub-lethal NIMEL irradiation, on normal growth of MRSA colonies.

$$\mu_1-\mu_2>0$$

Figure 15:
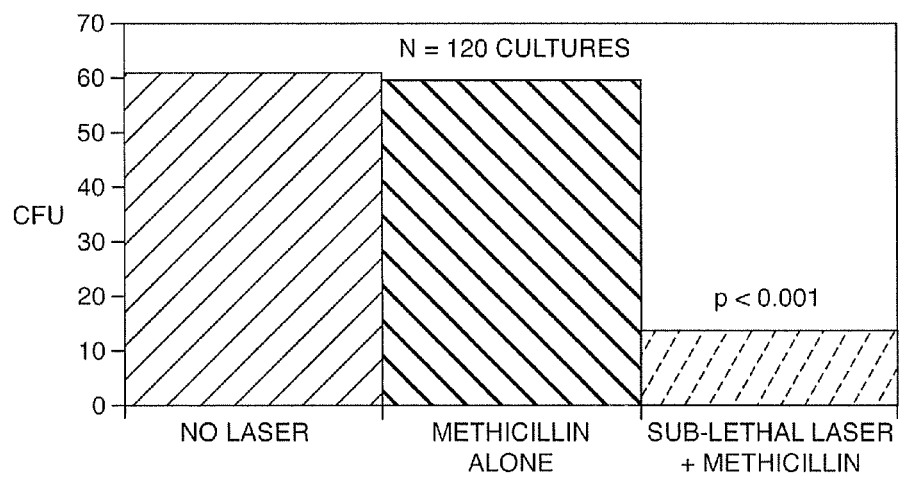
FIG. 15 shows the synergistic effects of NIMELS and methicillin in growth inhibition of MRSA colonies; data show methicillin is being potentiated by sub-lethal NIMELS dosimetry.

Will uphold that the addition of methicillin produces a deleterious effect after sub-lethal NIMEL irradiation, on normal growth of MRSA colonies.
Results:
As shown in FIG. 15, this experiment clearly showed that under sub-lethal laser parameters with the NIMELS system, $\mu_1-\mu_2>=0$, meaning that the addition of methicillin produces a deleterious effect after sub-lethal NIMEL irradiation on normal growth of MRSA colonies as shown by CFU count. This suggest that methicillin (independent of an efflux pump) is being potentiated by the NIMELS effect on $\Delta\Psi$-steady-bact of the MRSA.

Hence, the NIMELS laser and its concomitant optical $\Delta\Psi$-plas-bact lowering phenomenon is synergistic with cell wall inhibitory antimicrobials in MRSA. Without wishing to be bound by theory, this must function via the inhibition of anabolic (periplasmic) ATP coupled functions, as MRSA does not have efflux pumps for methicillin.

Example XII

Assessment of the Impact of Sub-Lethal Doses of NIMELS Laser on MRSA with Bacitracin and $\Delta\Psi$-Plas-Bact Inhibition of Cell Wall Synthesis Bacitracin is a mixture of cyclic polypeptides produced by *Bacillus subtilis*. As a toxic and difficult-to-use antibiotic, bacitracin cannot generally be used orally, but used topically.
Mechanism of Action:
Bacitracin interferes with the dephosphorylation of the $C_{55}$-isoprenyl pyrophosphate, a molecule which carries the building blocks of the peptidoglycan bacterial cell wall outside of the inner membrane in gram negative organisms and the plasma membrane in gram positive organism.

It has been shown in the gram positive bacterium *Bacillus subtilis*, that the activities of peptidoglycan autolysins are increased (i.e., no longer inhibited) when the ETS was blocked by adding proton conductors. This indicates that $\Delta\Psi$-plas-bact and $\Delta\mu H^+$ (independent of storing energy for cellular enzymatic functions) potentially has a profound and exploitable influence on cell wall anabolic functions and physiology.

In addition, it has been reported that $\Delta\Psi$-plas-bact uncouplers inhibit peptidoglycan formation with the accumulation of the nucleotide precursors involved in peptidoglycan synthesis, and the inhibition of transport of N-acetylglucosamine (GlcNAc), one of the major biopolymers in peptidoglycan.
Hypothesis Testing:
Bacitracin potentiates the multiple influences of an optically lowered $\Delta\Psi$-plas-bact on a growing cell wall (i.e., increased cell wall autolysis, inhibited cell wall synthesis). This is especially relevant in gram positive bacteria such as MRSA, that do not have efflux pumps as resistance mechanisms for cell wall inhibitory antimicrobial compounds.

The null hypothesis is $\mu_1-\mu_2=0$ and $\mu_1-\mu_3=0$ where:
a) $\mu_1$ is sub-lethal dosimetry from the NIMEL laser system on MRSA as a control and;
b) $\mu_2$ is the same sub-lethal dosimetry from the NIMEL laser system on MRSA with the addition of bacitracin at resistant MIC just below effectiveness level and;

$$\mu_1-\mu_2=0$$

Will uphold that the addition of bacitracin produces no deleterious effect after sub-lethal NIMEL irradiation, on normal growth of MRSA colonies.

$$\mu_1-\mu_2>0$$

Will uphold that the addition of bacitracin produces a deleterious effect after sub-lethal NIMEL irradiation, on normal growth of MRSA colonies.
Results:
As shown in FIG. 16, this experiment clearly showed that under sub-lethal laser parameters with the NIMELS system, $\mu_1-\mu_2>=0$, meaning that the addition of bacitracin produces a deleterious effect after sub-lethal NIMEL irradiation, on normal growth of MRSA colonies. In FIG. 16, arrows point to MRSA growth or a lack thereof in the two samples shown. This indicates that bacitracin (independent of an efflux pump) is being potentiated by the NIMELS effect on $\Delta\Psi$-steady-bact of the MRSA.

Hence, the NIMELS laser and its concomitant optical $\Delta\Psi$-plas-bact lowering phenomenon is synergistic with cell wall inhibitory antimicrobials in MRSA. Without wishing to be bound by theory, this most likely functions via the inhibition of anabolic (periplasmic) ATP coupled functions as MRSA does not have efflux pumps for bacitracin.

Example XIII

Assessment of the Impact of Sub-Lethal Doses of NIMELS Laser on *C. albicans* with Lamisil and Sporanox The purpose of this experiment was to observe if a sub-lethal dose of the NIMEL laser will potentiate the effect of the antifungal compounds Lamisil and/or sporanox in *C. albicans*.
Introduction:
It has been found that a reduction of the cytosolic ATP concentration in fungal cells leads to a suppression of the plasma membrane-bound $H^+$-ATPase that generates $\Delta\Psi$p-fungi, and that this impairment weakens other cellular activities. Additionally, the lowering of the $\Delta\Psi$p-fungi causes plasma membrane bioenergetic and thermodynamic disruption, leading to an influx of protons that collapse the proton motive force and, hence, inhibits nutrient uptake. Of further note, ATP is necessary for the biosynthesis of the fungal plasma membrane lipid ergosterol. Ergosterol is the structural lipid that is targeted by the majority of relevant commercial antifungal compounds used in medicine today (i.e., azoles, terbinafine and itraconazole) including lamisil and sporanox (and generic counterparts thereof).

Also, recently, it has bee shown that two novel antimicrobial peptides (Pep2 and Hst5) have the ability to cause ATP to be effluxed out of fungal cells (i.e., depleting intracellular ATP concentrations) and that this lowered cytosolic ATP causes the inactivation of ABC transporters CDR1 and CDR2 which are ATP-dependent efflux pumps of antifungal agents.
Lamisil:

Lamisil (like other allylamines) inhibits ergosterol synthesis by inhibiting squalene epoxidase, an enzyme that is part of the fungal cell wall synthesis pathway.
Sporanox:

The mechanism of action of itraconazole (Sporanox) is the same as the other azole antifungals: it inhibits the fungal cytochrome P450 oxidase-mediated synthesis of ergosterol.
Hypothesis:

The NIMELS laser at sub-lethal dosimetry on *C. albicans* potentiates lamisil and sporanox due to of an optically lowered $\Delta\Psi$-plas-fungi and/or $\Delta\Psi$-mito-fungi by depolarizing the membranes and depleting cellular ATP in the fungus.

The null hypothesis is $\mu_1-\mu_2=0$ and $\mu_1-\mu_3=0$ where:

a) $\mu_1$ is sub-lethal dosimetry from the NIMEL laser system on *C. albicans* as a control and;

b) $\mu_2$ is the same sub-lethal dosimetry from the NIMEL laser system on *C. albicans* with the addition of Sporanos at resistant MIC just below effectiveness level and;

c) $\mu_3$ is the same sub-lethal dosimetry from the NIMEL laser system on *C. albicans* with the addition of Lamisil at resistant MIC just below effectiveness level.

The data indicates that the addition of the antifungal lamisil and/or sporanox after sub-lethal irradiation, results in the reduction in growth of these *C. albicans* colonies, as follows:

$\mu_1-\mu_2=0$

Will uphold that the addition of Sporanox produces no deleterious effect after sub-lethal NIMEL irradiation, on normal growth of *C. albicans* colonies.

$\mu_1-\mu_2>0$

Will uphold that the addition of Sporanox produces a deleterious effect after sub-lethal NIMEL irradiation, on normal growth of *C. albicans* colonies.

$\mu_1-\mu_3=0$

Will uphold that the addition of Lamisil produces no deleterious effect after sub-lethal NIMEL irradiation, on normal growth of *C. albicans* colonies.

$\mu_1-\mu_3>0$

Will uphold that the addition of Lamisil produces a deleterious effect after sub-lethal NIMEL irradiation, on normal growth of *C. albicans* colonies.

TABLE 12

*Candida Albicans* NIMELS Dosimetry Charts
First lasing procedure: Both 870 and 930
Second lasing procedure 930 alone

| Test | Parameters | Output Power (W) | Beam Spot (cm) | Area of Spot (cm2) | Time (sec) |
|---|---|---|---|---|---|
| AF-8 | Test (H-1) 870 at 4.25 W and 930 at 4.25 W for 18 min followed by | 8.0 | 1.5 | 1.77 | |
| AF-8 | Test (H-1) 930 at 8.5 W for 12 min | 8.0 | 1.5 | 1.77 | |

TABLE 13

| | | Colony Counts: | | | | | |
|---|---|---|---|---|---|---|---|
| | | Control | | | Experimental | | |
| Group | Replicate | AGAR | Lamisil 0.5 ug/ml | Sporanox 0.5 ug/ml | AGAR | Lamisil 0.5 ug/ml | Sporanox 0.5 ug/ml |
| AF8 | 1 | 220 | 280 | 311 | n.d. | 78 | 80 |
| | 2 | 320 | n.d. | 295 | 249 | 74 | 107 |
| | 3 | 266 | 290 | 360 | 330 | 101 | 110 |
| | 4 | 248 | 335 | 332 | 209 | 70 | 86 |
| | 5 | 190 | 334 | 320 | 244 | 90 | 91 |

Results:

This experiment clearly showed that under sub-lethal laser parameters using the NIMELS system, $\mu_1-\mu_2=0$ and $\mu_1-\mu_3>0$, meaning that the addition of lamisil produces a deleterious effect after sub-lethal NIMEL irradiation, on normal growth of *C. albicans* colonies. This suggest that egosterol biosynthesis inhibitors (lamisil and sporanox) are potentiated by a sub-lethal dosimetry irradiation of the NIMELS Laser system.

Example XIV

NIMELS Dosimetry Calculations

The examples that follow describe selected experiments depicting the ability of the NIMELS approach to impact upon the viability of various commonly found microorganisms at the wavelengths described herein. The microorganisms exemplified include *E. coli* K-12, multi-drug resistant *E. coli*, *Staphylococcus aureus*, methicillin-resistant *S. aureus*, *Candida albicans*, and *Trichophyton rubrum*.

As discussed in more details supra, NIMELS parameters include the average single or additive output power of the laser diodes, and the wavelengths (870 nm and 930 nm) of the diodes. This information, combined with the area of the laser beam or beams (cm$^2$) at the target site, provide the initial set of information which may be used to calculate effective and safe irradiation protocols according to the invention.

The power density of a given laser measures the potential effect of NIMELS at the target site. Power density is a function of any given laser output power and beam area, and may be calculated with the following equations:

For a single wavelength:

$$\text{Power Density}(W/cm^2) = \frac{\text{Laser Output Power}}{\text{Beam Diameter}(cm^2)} \quad 1)$$

For dual wavelength treatments:

$$\text{Power Density(W/cm}^2) = \frac{\text{Laser(1) Output Power}}{\text{Beam Diameter(cm}^2)} + \frac{\text{Laser(2) Output Power}}{\text{Beam Diameter(cm}^2)} \quad 2)$$

Beam area can be calculated by either:

$$\text{Beam Area (cm}^2) = \text{Diameter (cm)}^2 * 0.7854 \text{ or Beam Area (cm}^2) = \text{Pi}*\text{Radius (cm)}^2 \quad 3)$$

The total photonic energy delivered into the tissue by one NIMELS laser diode system operating at a particular output power over a certain period is measured in Joules, and is calculated as follows:

$$\text{Total Energy (Joules)} = \text{Laser Output Power (Watts)} * \text{Time (Secs.)} \quad 4)$$

The total photonic energy delivered into the tissue by both NIMELS laser diode systems (both wavelengths) at the same time, at particular output powers over a certain period, is measured in Joules, and is calculated as follows:

$$\text{Total Energy (joules)} = [\text{Laser(1)Output Power (Watts)}*\text{Time (Secs)}] + [\text{Laser (2) Output Power (Watts)}*\text{Time(Secs)}] \quad 5)$$

In practice, it is useful (but not necessary) to know the distribution and allocation of the total energy over the irradiation treatment area, in order to correctly measure dosage for maximal NIMELS beneficial response. Total energy distribution may be measured as energy density (joules/cm$^2$). As discussed infra, for a given wavelength of light, energy density is the most important factor in determining the tissue reaction. Energy density for one NIMELS wavelength may be derived as follows:

$$\text{Energy Density(Joules/cm}^2) = \frac{\text{Laser Output power(Watts)} * \text{Time(secs)}}{\text{Beam Area(cm}^2)} \quad 6)$$

$$\text{Energy Density (Joule/cm}^2) = \text{Power Density (W/cm}^2) * \text{Time (secs)} \quad 7)$$

When two NIMELS wavelengths are being used, the energy density may be derived as follows:

$$\text{Energy Density(Joules/cm}^2) = \frac{\text{Laser(1) Output power(Watts)}*\text{Time(secs)}}{\text{Beam Area(cm}^2)} + \frac{\text{Laser(2) Output power(Watts)}*\text{Time(secs)}}{\text{Beam Area(cm}^2)} \quad 8)$$

or, $$\text{Energy Density (Joule/cm2)} = \text{Power Density (1)(W/cm}^2)*\text{Time (Secs)} + \text{Power Density(2) (W/cm}^2)*\text{Time (Secs)} \quad 9)$$

To calculate the treatment time for a particular dosage, a practitioner may use either the energy density (J/cm$^2$) or energy (J), as well as the output power (W), and beam area (cm$^2$) using either one of the following equations:

$$\text{Treatment Time(seconds)} = \frac{\text{Energy Density(Joules/cm}^2)}{\text{Output power Density(W/cm}^2)} \quad 10)$$

$$\text{Treatment Time(seconds)} = \frac{\text{Energy(Joules)}}{\text{Laser Output Power(Watts)}} \quad 11)$$

Because dosimetry calculations such as those exemplified in this Example can become burdensome, the therapeutic system may also include a computer database storing all researched treatment possibilities and dosimetries. The computer (a dosimetry and parameter calculator) in the controller is preprogrammed with algorithms based on the above-described formulas, so that any operator can easily retrieve the data and parameters on the screen, and input additional necessary data (such as: spot size, total energy desired, time and pulse width of each wavelength, tissue being irradiated, bacteria being irradiated) along with any other necessary information, so that any and all algorithms and calculations necessary for favorable treatment outcomes can be generated by the dosimetry and parameter calculator and hence run the laser.

In the examples that follow, in summary, when the bacterial cultures were exposed to the NIMELS laser, the bacterial kill rate (as measured by counting Colony Forming Units or CFU on post-treatment culture plates) ranged from 93.7% (multi-drug resistant E. coli) to 100% (all other bacteria and fungi).

Example XV

Bacterial Methods: NIMELS Treatment Parameters for In Vitro E. coli Targeting

The following parameters illustrate the methods according to the invention as applied to E. coli, at final temperatures well below those associated in the literature with thermal damage.

A. Experiment Materials and Methods for E. coli K-12:

E. coli K12 liquid cultures were grown in Luria Bertani (LB) medium (25 g/L). Plates contained 35 mL of LB plate medium (25 g/L LB, 15 g/L bacteriological agar). Culture dilutions were performed using PBS. All protocols and manipulations were performed using sterile techniques.

B. Growth Kinetics

Drawing from a seed culture, multiple 50 mL LB cultures were inoculated and grown at 37° C. overnight. The next morning, the healthiest culture was chosen and used to inoculate 5% into 50 mL LB at 37° C. and the O.D.$_{600}$ was monitored over time taking measurements every 30 to 45 minutes until the culture was in stationary phase.

C. Master Stock Production Starting with a culture in log phase (O.D.$_{600}$ approximately 0.75), 10 mL were placed at 4° C. 10 mL of 50% glycerol were added and was aliquoted into 20 cryovials and snap frozen in liquid nitrogen. The cryovials were then stored at −80° C.

D. Liquid Cultures

Liquid cultures of E. coli K12 were set up as described previously. An aliquot of 100 μL was removed from the subculture and serially diluted to 1:1200 in PBS. This dilution was allowed to incubate at room temperature approximately 2 hours or until no further increase in O.D.$_{600}$ was observed in order to ensure that the cells in the PBS suspension would reach a static state (growth) with no significant doubling and a relatively consistent number of cells could be aliquoted further for testing.

Once it was determined that the K12 dilution was in a static state, 2 mL of this suspension were aliquoted into selected wells of 24-well tissue culture plates for selected NIMELS experiments at given dosimetry parameters. The plates were incubated at room temperature until ready for use (approximately 2 hrs).

Following laser treatments, 100 µl was removed from each well and serially diluted to 1:1000 resulting in a final dilution of 1:12×10$^5$ of initial K12 culture. Aliquots of 3×200 L of each final dilution were spread onto separate plates in triplicate. The plates were then incubated at 37° C. for approximately 16 hours. Manual colony counts were performed and recorded. A digital photograph of each plate was also taken.

removed from each well and spread onto separate plates. The plates were then incubated at 37° C. for approximately 91 hours. Manual colony counts were performed and recorded after 66 hours and 91 hours of incubation. While control wells all grew the organism, 100% of laser-treated wells as described herein had no growth. A digital photograph of each plate was also taken.

Thermal tests performed on PBS solution, starting from room temperature. Ten (10) Watts of NIMELS laser energy were available for use in a 12 minute lasing cycle, before the temperature of the system is raised close to the critical threshold of 44° C.

TABLE 14

Time & Temperature measurements for In Vitro NIMELS Dosimetries

| NIMEL OUTPUT POWER (W) | BEAM SPOT 1.5 CM DIAMETER OVERLAP AREA (CM$^2$) | TREATMENT TIME (SEC) | TOTAL ENERGY (JOULES) | ENERGY DENSITY (RADIANT EXPOSURE) (J/CM$^2$) | POWER DENSITY (IRRADIANCE) (W/CM$^2$) | TEMPERATURE START | TEMP FINISH |
|---|---|---|---|---|---|---|---|
| Plate 1-N -- 3.0 + 3.0 = 6.0 W | 1.76 | 720 | 4320 | 2448 | 3.40 | 20.5° C. | 34.0° C. |
| Plate 2-N -- 3.5 + 3.5 = 7.0 W | 1.76 | 720 | 5040 | 2858 | 3.97 | 20.7° C. | 36.5° C. |
| Plate 3-N - 4.0 + 4.0 = 8.0 W | 1.76 | 720 | 5760 | 3268 | 4.54 | 21.0° C. | 38.5° C. |
| Plate 4-N - 4.5 + 4.5 = 9.0 W | 1.76 | 720 | 6480 | 3679 | 5.11 | 2.0° C. | 41.0° C. |
| Plate 5-N - 5.0 + 5.0 = 10. W | 1.76 | 720 | 7200 | 4089 | 5.68 | 21.0° C. | 40.5° C. |
| Plate 6-N - 5.5 + 5.5 = 11 W | 1.76 | 720 | 7920 | 4500 | 6.25 | 21.0° C. | 46.0° C. |
| Plate 7-N - 7.0 + 7.0 = 14.0 W | 1.76 | 360 | 5040 | 2863 | 7.95 | 21.0° C. | 47.0° C. |
| Plate 8-N - 7.5 + 7.5 = 15 W | 1.76 | 360 | 5400 | 3068 | 8.52 | 21.7° C. | 47.2° C. |

Similar cell culture and kinetic protocols were performed for all NIMELS irradiation tests with *S. aureus* and *C. albicans* in vitro tests. For example, *C. albicans* ATCC 14053 liquid cultures were grown in YM medium (21 g/L, Difco) medium at 37° C. A standardized suspension was aliquoted into selected wells in a 24-well tissue culture plate. Following laser treatments, 100 µL was removed from each well and serially diluted to 1:1000 resulting in a final dilution of 1:5× 10$^5$ of initial culture. 3×100 µL of each final dilution were spread onto separate plates. The plates were then incubated at 37° C. for approximately 16-20 hours. Manual colony counts were performed and recorded. A digital photograph of each plate was also taken.

*T. rubrum* ATCC 52022 liquid cultures were grown in peptone-dextrose (PD) medium at 37° C. A standardized suspension was aliquoted into selected wells in a 24-well tissue culture plate. Following laser treatments, aliquots were Example XVI Dosimetry Values for NIMELS Laser Wavelength 930 nm for *E. coli* In Vitro Targeting The instant experiment demonstrates that the NIMELS single wavelength λ=930 nm is associated with quantitatable antibacterial efficacy against *E. coli* in vitro within safe thermal parameters for mammalian tissues.

Experimental data in vitro demonstrates that if the threshold of total energy into the system with 930 nm alone of 5400 J and an energy density of 3056 J/cm$^2$ is met in 25% less time, 100% antibacterial efficacy is still achievable.

TABLE 15

Sub-thermal NIMELS (λ = 930) Dosimetry for In Vitro *E. coli* Targeting

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) | *E-COLI* KILL PERCENTAGE |
|---|---|---|---|---|---|---|
| 7.0 | 1.5 | 720 | 5040 | 2852 | 3.96 | 40.2% |
| 8.0 | 1.5 | 720 | 5760 | 3259 | 4.53 | 100.0% |
| 10.0 | 1.5 | 540 | 5400 | 3056 | 5.66 | 100.0% |

Experimental data in vitro also demonstrates that treatments using a single energy with λ=930 nm has antibacterial in vitro efficacy against the bacterial species *S. aureus* within safe thermal parameters for mammalian tissues.

It is also believed that if the threshold of total energy into the system of 5400 J and an energy density of 3056 J/cm² is met in 25% less time with *S. aureus* and other bacterial species, that 100% antibacterial efficacy will still be achieved.

TABLE 16

Sub-thermal NIMELS ($\lambda$ = 930) Dosimetry for In Vitro *S. aureus* Targeting

| OUTPUT POWER (W) | BEAM SPOT (CM) | TIME (SEC) | TOTAL ENERGY JOULES | ENERGY DENSITY (J/CM²) | POWER DENSITY (W/CM²) | *S AUREUS* KILL PERCENTAGE |
|---|---|---|---|---|---|---|
| 7.0 | 1.5 | 720 | 5040 | 2852 | 3.96 | 24.1% |
| 8.0 | 1.5 | 720 | 5760 | 3259 | 4.53 | 100.0% |

Experimental in vitro data also showed that the NIMELS single wavelength of $\lambda$=930 nm has anti-fungal efficacy against in vitro *C. albicans* at ranges within safe thermal parameters for mammalian tissues.

It is also believed that if the threshold of total energy into the system of 5400 J and an energy density of 3056 J/cm² is met in 25% less time, that 100% antifungal efficacy will still be achieved.

TABLE 17

Sub-thermal NIMELS ($\lambda$ = 930) Dosimetry for In Vitro *C. albicans* Targeting

| OUTPUT POWER (W) | BEAM SPOT (CM) | TIME (SEC.) | TOTAL ENERGY JOULES | ENERGY DENSITY (J/CM²) | POWER DENSITY (W/CM²) | *CANDIDA ALBICANS* KILL PERCENTAGE |
|---|---|---|---|---|---|---|
| 8.0 | 1.5 | 720 | 5760 | 3259 | 4.53 | 100.0% |
| 9.0 | 1.5 | 720 | 6840 | 3681 | 5.11 | 100.0% |

Example XVII

Dosimetry Values for NIMELS Laser Wavelength 870 nm In Vitro

Experimental in vitro data also demonstrates that no significant kill is achieved up to a total energy of 7200 J, and energy density of 4074 J/cm² and a power density of 5.66 0 W/cm² with the wavelength of 870 nm alone against *E. coli*.

Example XVIII

NIMELS Unique Alternating Synergistic Effect Between 870 nm and 930 nm Optical Energies Experimental in vitro data also demonstrates that there is an additive effect between the two NIMELS wavelengths ($\lambda$=870 nm and 930 nm) when they are alternated (870 nm before 930 nm). The presence of the 870 nm NIMELS wavelength as a first irradiance has been found to enhance the effect of the antibacterial efficacy of the second 930 nm NIMELS wavelength irradiance.

Experimental in vitro data demonstrates that this synergistic effect (combining the 870 nm wavelength to the 930 nm wavelength) allows for the 930 nm optical energy to be reduced. As shown herein, the optical energy was reduced to approximately ⅓ of the total energy and energy density required for NIMELS 100% *E. coli* antibacterial efficacy, when the (870 nm before 930 nm) wavelengths are combined in an alternating manner.

Experimental in vitro data also demonstrates that this synergistic mechanism can allow for the 930 nm optical energy (total energy and energy density) to be reduced to approximately ½ of the total energy density necessary for NIMELS 100% *E. coli* antibacterial efficacy if equal amounts of 870 nm optical energy are added to the system before the 930 nm energy at 20% higher power densities.

TABLE 18

*E. coli* Studies - Single wavelength $\lambda$ = 870 nm

| OUTPUT POWER (W) | BEAM SPOT (CM) | TIME (SEC.) | TOTAL ENERGY JOULES | ENERGY DENSITY (J/CM²) | POWER DENSITY (W/CM²) | CONTROL CFUs | NIMELS CFUs | DIFFERENCE CONTROL – NIMEL | *E. COLI* KILL PERCENTAGE |
|---|---|---|---|---|---|---|---|---|---|
| 6.0 | 1.5 | 720 | 4320 | 2445 | 3.40 | 90 | 95 | (5) | −5.6% |
| 7.0 | 1.5 | 720 | 5040 | 2852 | 3.96 | 94 | 94 | 0 | 0.0% |
| 8.0 | 1.5 | 720 | 5760 | 3259 | 4.53 | 93 | 118 | (25) | −26.9% |
| 9.0 | 1.5 | 720 | 6480 | 3667 | 5.09 | 113 | 112 | 1 | 0.9% |
| 10.0 | 1.5 | 720 | 7200 | 4074 | 5.66 | 103 | 111 | (8) | −7.8% |
| 10.0 | 1.5 | 540 | 5400 | 3056 | 5.66 | 120 | 101 | 19 | 15.8% |

Comparable results using radiation having $\lambda$ = 870 nm alone were also observed with *S. aureus*.

TABLE 19

*E. coli* data from Alternating NIMELS Wavelengths

| OUTPUT POWER (W) | SPOT (CM) | TIME (SEC.) | TOTAL ENERGY JOULES | ENERGY DENSITY (J/CM$^2$) | POWER DENSITY (W/CM$^2$) | *E. COLI* KILL PERCENTAGE |
|---|---|---|---|---|---|---|
| 8 W/8 W | 1.5 | 540/180 12 min. | 4320/1440 = 5760 | 2445/815 = 3529 | 4.53/4.53 | 100.0% |
| 10 W/10 W | 1.5 | 240/240 8 min. | 2400/2400 = 4800 | 1358/1358 = 2716 | 5.66/5.66 | 100.0% |

This synergistic ability is significant to human tissue safety, as the 930 nm optical energy, heats up a system at a greater rate than the 870 nm optical energy, and it is beneficial to a mammalian system to produce the least amount of heat possible during treatment.

It is also believed that if the NIMELS optical energies (870 nm and 930 nm) are alternated in the above manner with other bacterial species, that the 100% antibacterial effect will be essentially the same.

Experimental in vitro data also demonstrates that there is also an additive effect between the two NIMELS wavelengths (870 nm and 930 nm) when they are alternated (870 nm before 930 nm) while irradiating fungi. The presence of the 870 nm NIMELS wavelength as a first irradiance mathematically enhances the effect of the anti-fungal efficacy of the second 930 nm NIMELS wavelength irradiance.

Experimental in vitro data (see, table infra) demonstrates that this synergistic mechanism can allow for the 930 nm optical energy (total energy and energy density) to be reduced to approximately ½ of the total energy density necessary for NIMELS 100% antifungal efficacy if equal amounts of 870 nm optical energy is added to the system before the 930 nm energy at 20% higher power densities than is required for bacterial species antibacterial efficacy.

It is also believed that if the NIMELS optical energies (870 nm and 930 nm) are alternated in the above manner with other fungi species, that the 100% anti-fungal effect will be essentially the same.

Example XIX

NIMELS Unique Simultaneous Synergistic Effect Between λ=870 nm and λ=930 nm Optical Energies Experimental in vitro data also demonstrates that there is an additive effect between the two NIMELS wavelengths (870 nm and 930 nm) when they are used simultaneously (870 nm combined with 930 nm). The presence of the 870 nm NIMELS wavelength and the 930 nm NIMELS wavelength as a simultaneous irradiance absolutely enhances the effect of the antibacterial efficacy of the NIMELS system.

TABLE 20

*C. albicans* Data from Alternating NIMEL Wavelengths

| OUTPUT POWER (W) | SPOT (CM) | TIME (SEC) | TOTAL ENERGY JOULES | ENERGY DENSITY (J/CM$^2$) | POWER DENSITY (W/CM$^2$) | *CANDIDA ALBICANS* KILL PERCENTAGE |
|---|---|---|---|---|---|---|
| 10 W/10 W | 1.5 | 240/240 8 min | 2400/2400 = 4800 | 1358/1358 = 2716 | 5.66/5.66 | 100.0%* |

This synergistic effect is significant to human tissue safety, as the 930 nm optical energy, heats up a system at a greater rate than the 870 nm optical energy, and it is beneficial to a mammalian system to produce the least amount of heat possible during treatment.

In vitro experimental data (see, for example, Tables IX and X below) demonstrated that by combining λ=870 nm and λ=930 nm (in this example used simultaneously) effectively reduces the 930 nm optical energy and density by about half of the total energy and energy density required when using a single treatment according to the invention.

TABLE 21

*E. coli* data from Combined NIMEL Wavelengths

| OUTPUT POWER (W) 870 NM/ 930 NM | BEAM SPOT (CM) | TIME (SEC) | TOTAL ENERGY JOULES | ENERGY DENSITY (J/CM$^2$) | POWER DENSITY (W/CM$^2$) | *E-COLI* KILL PERCENTAGE |
|---|---|---|---|---|---|---|
| 5 W + 5 W = 10 | 1.5 | 720 | 3600 (×2) = 7200 | 2037 (×2) = 4074 | 5.66 | 100% |

TABLE 22

S. aureus data from Combined NIMELS Wavelengths

| OUTPUT POWER (W) 870 NM/ 930 NM | BEAM SPOT (CM) | TIME (SEC) | TOTAL ENERGY JOULES | ENERGY DENSITY (J/CM$^2$) | POWER DENSITY (W/CM$^2$) | S. AUREUS KILL PERCENTAGE |
|---|---|---|---|---|---|---|
| 5 W + 5 W = 10 W | 1.5 | 720 | 3600 (×2) = 7200 | 2037 (×2) = 4074 | 5.66 | 98.5% |
| 5.5 W + 5.5 = 11 W | 1.5 | 720 | 3960 (×2) = 7920 | 2241 (×2) = 4482 | 6.22 | 100% |

This simultaneous synergistic ability is significant to human tissue safety, as the 930 nm optical energy, heats up a system at a greater rate than the 870 nm optical energy, and it is beneficial to a mammalian system to produce the least amount of heat possible during treatment.

Figure 17:
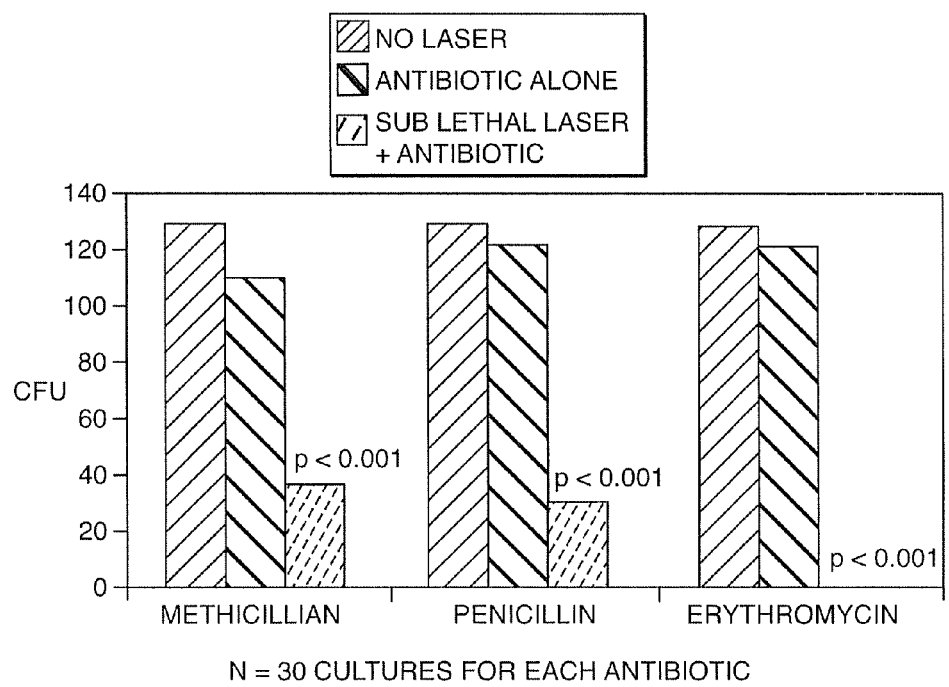
FIG. 17 shows a bar chart depicting the synergistic effects, as indicated by experimental data, of NIMELS with methicillin, penicillin and erythromycin in growth inhibition of MRSA colonies

It is also believed that if the NIMELS optical energies (870 nm and 930 nm) are used simultaneously in the above manner with other bacterial species, that the 100% antibacterial effect will be essentially the same. (See, FIGS. 17, 18, and 19.)

Experimental in vitro data also demonstrates that there is an additive effect between the two NIMELS wavelengths (870 nm and 930 nm) when they are used simultaneously on fungi. The presence of the 870 nm NIMELS wavelength and the 930 nm NIMELS wavelength as a simultaneous irradiance have been found to enhance the effect of the anti-fungal efficacy of the NIMELS system.

Experimental in vitro data demonstrates that this synergistic effect (connecting the 870 nm wavelength to the 930 nm wavelength for simultaneous irradiation) allows for the 930 nm optical energy to be reduced to approximately ½ of the total energy and energy density required for NIMELS 100% C. albicans anti-fungal efficacy, when the (870 nm before 930 nm) wavelengths are combined in a simultaneous manner.

TABLE 23

Candida albicans from Combined NIMELS Wavelengths

| OUTPUT POWER (W) 870 NM/ 930 NM | BEAM SPOT (CM) | TIME (SEC) | TOTAL ENERGY JOULES | ENERGY DENSITY (J/CM$^2$) | POWER DENSITY (W/CM$^2$) | C. ALBICANS KILL PERCENTAGE |
|---|---|---|---|---|---|---|
| 5 W + 5 W = 10 | 1.5 | 720 | 3600 (×2) = 7200 | 2037 (×2) = 4074 | 5.66 | 100% | such modes thereby reducing the exposure at the λ=930 associated with temperature increases which are minimized.

Experimental in vitro data also demonstrates that when E. coli is irradiated alone with a (control) wavelength of λ=830 nm, at the following parameters, the control 830 nm laser produced zero antibacterial efficacy for 12 minutes irradiation cycles, at identical parameters to the minimum NIMELS dosimetry associated with 100% antibacterial and anti-fungal efficacy with radiation of λ=930 nm.

TABLE 24

E. coli Single Wavelength λ = 830 nm

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|
| 8.0 | 1.5 | 720 | 5760 | 3259 | 4.53 |
| 9.0 | 1.5 | 720 | 6480 | 3667 | 5.09 |

Experimental in vitro data also demonstrates that when applied at safe thermal dosimetries, there is little additive effect when using radiance of λ=830 nm in combination with λ=930 nm. The presence of the 830 nm control wavelength as a first irradiance is far inferior to the enhancement effect of the 870 nm NIMELS wavelength in producing synergistic antibacterial efficacy with the second 930 nm NIMELS wavelength.

Thus, NIMELS wavelengths (λ=870 nm and 930 nm) may be used to achieve antibacterial and anti-fungal efficacy in an alternating mode or simultaneously or in any combination of

TABLE 25

E. coli data from Substituted alternating 830 nm control Wavelength

| OUTPUT POWER (W) 830 NM/ 930 NM | BEAM SPOT (CM) | TIME (SEC) | TOTAL ENERGY JOULES | ENERGY DENSITY (J/CM$^2$) | POWER DENSITY (W/CM$^2$) | E. COLI KILL PERCENTAGE |
|---|---|---|---|---|---|---|
| 8 W/8 W | 1.5 | 540/180 12 min | 4320/1440 = 5760 | 2445/815 = 3529 | 4.53/4.53 | 0% |
| 10 W/10 W | 1.5 | 240/240 8 min | 2400/2400 = 4800 | 1358/1358 = 2716 | 5.66/5.66 | 65% |

Experimental in vitro data also demonstrates that when applied at safe thermal dosimetries, there is less additive effect with the 830 nm wavelength, and the NIMELS 930 nm wavelength when they are used simultaneously. In fact, experimental in vitro data demonstrates that 17% less total energy, 17% less energy density, and 17% less power density is required to achieve 100% E. coli antibacterial efficacy when 870 nm is combined simultaneously with 930 nm vs. the commercially available 830 nm. This, again, substantially reduces heat and harm to an in vivo system being treated with the NIMELS wavelengths.

TABLE 26

E. coli data from Substituted Simultaneous 830 nm control Wavelength

| OUTPUT POWER (W) 830 NM/ 930 NM | BEAM SPOT (CM) | TIME (SEC) | TOTAL ENERGY JOULES | ENERGY DENSITY (J/CM$^2$) | POWER DENSITY (W/CM$^2$) | E-COLI KILL PERCENTAGE |
|---|---|---|---|---|---|---|
| 5 W + 5 W = 10 | 1.5 | 720 | 3600 (×2) = 7200 | 2037 (×2) = 4074 | 5.66 | 91% |
| 5.5 W + 5.5 = 11 W | 1.5 | 720 | 3960 (×2) = 7920 | 2250 (×2) = 4500 | 6.25 | 90% |
| 6 W + 6 W = 12 W | 1.5 | 720 | 3960 (×2) f = 8640* | 2454 (×2) = 4909* | 6.81* | 100% |

Amount of Bacteria Killed:

In vitro data also showed that the NIMELS laser system in vitro is effective (within thermal tolerances) against solutions of bacteria containing 2,000,000 (2×10$^6$) Colony Forming Units (CFU's) of E. coli and S. aureus. This is a 2× increase over what is typically seen in a 1 gm sample of infected human ulcer tissue. Brown et al. reported that microbial cells in 75% of the diabetic patients tested were all at least 100,000 CFU/gm, and in 37.5% of the patients, quantities of microbial cells were greater than 1,000,000 (1×10$^6$)CFU (see Brown et al., Ostomy Wound Management, 401:47, issue 10, (2001), the entire teaching of which is incorporated herein by reference).

Thermal Parameters:

Experimental in vitro data also demonstrates that the NIMELS laser system can accomplish 100% antibacterial and anti-fungal efficacy within safe thermal tolerances for human tissues.

Example XX

The Effects of Lower Temperatures on NIMELS

Cooling of Bacterial Species:

Experimental in vitro data also demonstrated that by substantially lowering the starting temperature of bacterial samples to 4° C. for two hours in PBS before lasing cycle, that optical antibacterial efficacy was not achieved at any currently reproducible antibacterial energies with the NIMELS laser system.

Example XXI

Nimels Effects on *Trychophyton rubrum*

This example demonstrates the effects NIMELS wavelengths (870 nm and 930 nm) when used in alternating or simultaneous modes.

TABLE 27

NIMELS *T. rubrum* Tests Alternating Wavelengths

| EXP. NO. | OUTPUT POWER (W) 870 NM/ 930 NM | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 1 | 8 W/8 W | 1.5 | 540/180 12 min. | 4320/1440 = 5760 | 2445/815 = 3529 | 4.53/4.53 |

TABLE 27-continued

NIMELS *T. rubrum* Tests Alternating Wavelengths

| EXP. NO. | OUTPUT POWER (W) 870 NM/ 930 NM | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 2 | 10 W/10 W | 1.5 | 240/240 8 min. | 2400/2400 = 4800 | 1358/1358 = 2716 | 5.66/5.66 |

Experiment No. 1 = Minimal Effect
Experiment No. 2 = 100% Kill in all plates

TABLE 28

NIMELS *T. rubrum* - Simultaneous Wavelengths

| EX NO. | OUTPUT POWER (W) 870 NM & 930 NM | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 3 | 5 + 5 = 10 | 1.5 | 720 12 min. | 3600 (×2) = 7200 | 2037 (×2) = 4074 | 5.66 |
| 4 | 5.5 W + 5.5 W = 11 W | 1.5 | 720 | 3960 (×2) = 7920 | 2250 (×2) = 4500 | 6.25 |
| 5 | 6 W + 6 W = 12 W | 1.5 | 720 | 3960 (×2) = 8640 | 2454 (×2) = 4909 | 6.81 |

Experiments Nos. 3, 4, and 5 = 100% Kill in all plates

TABLE 29

NIMELS *T. rubrum* - Single Wavelength

| EXP NO λ = 930 | OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|---|
| 6 | 8.0 | 1.5 | 720 | 5760 | 3259 | 4.53 |
| 7 | 9.0 | 1.5 | 720 | 6840 | 3681 | 5.11 |

Experiments Nos. 6 and 7 = 100% Kill in all plates

TABLE 30

Control *T. rubrum* - 830 nm/930 nm Alternating

| EXPERIMENT NO. λ 830 & λ = 930 | OUTPUT POWER (W) | BEAM SPOT (CM) | TIME (MIN.) | TOTAL ENERGY JOULES | ENERGY DENSITY (J/CM$^2$) | POWER DENSITY (W/CM$^2$) |
|---|---|---|---|---|---|---|
| 8 | 8 W/8 W | 1.5 | 540/180 12 min | 4320/1440 = 5760 | 2445/815 = 3529 | 4.53/4.53 |
| 9 | 10 W/10 W | 1.5 | 240/240 8 min | 2400/2400 = 4800 | 1358/1358 = 2716 | 5.66/5.66 |

Experiment No. 8 = No Effect
Experiment No. 9 = 100% Kill

Treatments as described in the above Table XVIII resulted in 100% kill.

TABLE 31

In Vitro Targeting of *T. rubrum* using λ = 830 nm and 930 nm

| OUTPUT POWER (W) | BEAM SPOT (CM) | TIME (SEC.) | TOTAL ENERGY JOULES | ENERGY DENSITY (J/CM$^2$) | POWER DENSITY (W/CM$^2$) |
|---|---|---|---|---|---|
| 5 + 5 = 10 | 1.5 | 720 | 3600 (×2) = 7200 | 2037 (×2) = 4074 | 5.66 |

Example XXII

MRSA/Antimicrobial Potentiation

This example shows the use of NIMELS wavelengths ($\lambda$=830 nm and 930 nm) in in vitro targeting of MRSA to increase antimicrobial sensitivity to methicillin. Four separate experiments have been performed. The data sets for these four experiments are presented in the tables that follow. See, also, FIG. 17, which shows: (a) the synergistic effects of NIMELS with methicillin, penicillin and erythromycin in growth inhibition of MRSA colonies; data show that penicillin and methicillin is being potentiated by sub-lethal NIMELS dosimetry by inhibiting the Bacterial Plasma Membrane Proton-motive force ($\Delta$p-plas-Bact) thereby inhibiting peptidoglycan synthesis anabolic processes that are co-targeted with the drug; and (b) that erythromycin is potentiated to a greater extent, because the Nimels effect is inhibiting the Bacterial Plasma Membrane Proton-motive force ($\Delta$p-plas-Bact) that supplies the energy for protein synthesis anabolic processes and erythromycin resistance efflux pumps.

Materials:

TABLE 32

| Bacteria | | | |
|---|---|---|---|
| ATCC ® Number: Top of Form Bottom of Form | BAA-43 ™ | Price: | |
| Organism: | *Staphylococcus aureus* subsp. *aureus* Rosenbach; deposited as *Staphylococcus aureus* Rosenbach | | |
| Designations: | HSJ216 | Isolation: | hospital, Lisbon, Portugal, 1998 [51476] |
| Depositor: | H De Lencastre | | |
| Biosafety Level: | 2 | Shipped: | freeze-dried |
| Growth Conditions: | ATCC medium 260: Trypticase soy agar with defibrinated sheep blood Growth conditions: aerobic Temperature: 37.0 C. | | |
| Permits/Forms: | In addition to the MTA mentioned above, other ATCC and/or regulatory permits may be required for the transfer of this ATCC material. Anyone purchasing | | |

TABLE 32-continued

| Bacteria | | | |
|---|---|---|---|
| ATCC ® Number: Top of Form Bottom of Form | BAA-43 ™ | Price: | |
| | ATCC material is ultimately responsible for obtaining the permits. Please click here for information regarding the specific requirements for shipment to your location. Related Products | | |
| Comments: | Brazilian clone of MRSA [12386] | | |
| Applications: | resistant to methicillin [51476] | | |
| References: | 51476: de Sousa MA, et al. Intercontinental spread of a multidrug-resistant methicillin-resistant *Staphylococcus aureus* clone. J. Clin. Microbiol. 36: 2590-2596, 1998. PubMed: 9705398 12386: Herminia De Lencastre, personal communication, the entire teaching is incorporated herein by reference. | | |

General Methods for CFU Counts:

TABLE 33

| Time (hrs) | Task | TE (hrs) |
|---|---|---|
| −18 | Inoculate overnight culture 50 ml directly from glycerol stock | |
| −4 | Set up starter cultures Three dilutions 1:50, 1:125, 1:250 Monitor $OD_{600}$ of starter cultures | |
| 0 | Preparation of plating culture At 10:00 am, the culture which is at $OD_{600}$ = 1.0 is diluted 1:300 in PBS (50 mls final volume) and stored at RT for 1 hour. (Room temp should be ~25° C.) | |
| +1 | Seeding of 24-well plates 2 ml aliquots are dispensed into pre-designated wells in 24-well plates and transferred to NOMIR (8 24-well plates total) | |
| +2 | Dilution of treated samples | |
| to +8 | After laser treatment, 100 μl from each well is diluted serially to a final dilution of 1:1000 in PBS. Plating of treated samples 100 μl of final dilution is plated in triplicate on TSB agar with and without 30 μg/ml methicillin. (6 TSB plates per well) Plates are incubated at 37° C. 18-24 hrs. | |
| +24 | Colonies are counted on each plate (96 plates total) | |

TABLE 34

MRSA Dosimetry Progression Nov. 6, 2006 Experiment #1
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm²) | Power Density (W/cm²) | Temp Initial C. | Temp Final C. |
|---|---|---|---|---|---|---|---|---|---|
| Test (1) 870 at 5 W and 930 at 5 W for 12 min followed by | 10.0 | 1.5 | 1.77 | 720 | 7200 | 4074 | 5.66 | 24.4 | 44 |
| Test (1) 930 at 8 W for 6 min | 8.0 | 1.5 | 1.77 | 360 | 2880 | 1630 | 4.53 | 44 | 46.8 |
| Test (2) 870 at 5.5 W and 930 at 5.5 W for 12 min followed by | 11.0 | 1.5 | 1.77 | 720 | 7920 | 4482 | 6.22 | 26.5 | 48.1 |
| Test (2) 930 at 8 W for 6 min | 8.0 | 1.5 | 1.77 | 360 | 2880 | 1630 | 4.53 | 48.1 | 47.4 |
| Test (3) 870 at 5.5 W and 930 at 5.5 W for 10 min followed by | 10.0 | 1.5 | 1.77 | 600 | 6000 | 3395 | 5.66 | 25.7 | 43.1 |
| Test (3) 930 at 8 W for 4 min | 8.0 | 1.5 | 1.77 | 240 | 1920 | 1086 | 4.53 | 43.1 | 44.8 |
| Test (4) 870 at 5.5 W and 930 at 5.5 W for 10 min followed by | 11.0 | 1.5 | 1.77 | 600 | 6600 | 3735 | 6.22 | 22.9 | 45.2 |
| Test (4) 930 at 8 W for 4 min | 8.0 | 1.5 | 1.77 | 240 | 1920 | 1086 | 4.53 | 45.2 | 45.3 |
| Test (5) 870 at 5 W and 930 at 5 W for 8 min followed by | 10.0 | 1.5 | 1.77 | 480 | 4800 | 2716 | 5.66 | 24.2 | 43.2 |

TABLE 34-continued

MRSA Dosimetry Progression Nov. 6, 2006 Experiment #1
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (5) 930 at 7 W for 4 min | 7.0 | 1.5 | 1.77 | 240 | 1680 | 951 | 3.96 | 43.2 | 43.8 |
| Test (6) 870 at 5.5 W and 930 at 5.5 W for 8 min followed by | 11.0 | 1.5 | 1.77 | 480 | 5280 | 2988 | 6.22 | 25.3 | 42.7 |
| Test (6) 930 at 7 W for 4 min | 7.0 | 1.5 | 1.77 | 240 | 1680 | 951 | 3.96 | 42.7 | 44.9 |
| Test (7) 870 at 5 W and 930 at 5 W for 6 min followed by | 10.0 | 1.5 | 1.77 | 360 | 3600 | 2037 | 5.66 | 26.2 | 40.6 |
| Test (7) 930 at 7 W for 4 min | 7.0 | 1.5 | 1.77 | 240 | 1680 | 951 | 3.96 | 40.6 | 44 |
| Test (8) 870 at 5.5 W and 930 at 5.5 W for 6 min followed by | 11.0 | 1.5 | 1.77 | 360 | 3960 | 2241 | 6.22 | 26 | 42 |
| Test (8) 930 at 7 W for 4 min | 7.0 | 1.5 | 1.77 | 240 | 1680 | 951 | 3.96 | 42 | 44.2 |

Independent Report for MRSA studies, 07 Nov. 2006 (MRSA Data Progression Nov. 7, 2006 Experiment #1)

Experiment 1—Design:

Eight different laser dosages were used to treat a saline-suspension of logarithmically growing MRSA, labeled A1 to H1.

The treated and a control untreated suspension were diluted and plated in triplicate on trypic soy agar with or without 30 μg/ml methicillin.

After 24 hrs of growth at 37° C. colonies were counted.

CFU (colony forming units) were compared between the plates with and without methicillin for both control (untreated) and treated MRSA.

Experiment 1—Results:

Conditions D1 through H1 showed a similar reduction in CFU on the methicillin plates in treated and untreated samples.

Conditions A1, B1 and C1 showed 30%, 33%, or 67% fewer CFU in the laser treated samples compared to the untreated controls, respectively.

This indicates that the treatments performed on sample A1, B1 and C1 sensitized the MRSA to the effects of methicillin.

TABLE 35

MRSA Data Progression Nov. 7, 2006 Experiment #1

| | | Methicillin (Meth) | | CFU | AVG | CFU/ml | Meth Effect | Laser Effect (+Meth) |
|---|---|---|---|---|---|---|---|---|
| A1 | Cont | no | 1 | 224 | 203.7 | 6.11E+08 | | |
| | | | 2 | 266 | | | | |
| | | | 3 | 121 | | | | |
| | | yes | 1 | 207 | 141.7 | 4.25E+08 | 0.695581 | |
| | | | 2 | 137 | | | | |
| | | | 3 | 81 | | | | |
| | Exp | no | 1 | 132 | 134.3 | 4.03E+08 | | |
| | | | 2 | 143 | | | | |
| | | | 3 | 128 | | | | |
| | | yes | 1 | 99 | 99.7 | 2.99E+08 | 0.741935 | 0.7035 |
| | | | 2 | 96 | | | | |
| | | | 3 | 104 | | | | |
| B1 | Cont | no | 1 | 235 | 188.3 | 5.65E+08 | | |
| | | | 2 | 220 | | | | |
| | | | 3 | 110 | | | | |
| | | yes | 1 | 166 | 169.3 | 5.08E+08 | 0.899115 | |
| | | | 2 | 192 | | | | |
| | | | 3 | 150 | | | | |
| | Exp | no | 1 | 213 | 200.3 | 6.01E+08 | | |
| | | | 2 | 199 | | | | |
| | | | 3 | 189 | | | | |
| | | yes | 1 | 102 | 113.3 | 3.40E+08 | 0.565724 | 0.6693 |
| | | | 2 | 107 | | | | |
| | | | 3 | 131 | | | | |
| C1 | Cont | no | 1 | 280 | 320.3 | 9.61E+08 | | |
| | | | 2 | 242 | | | | |
| | | | 3 | 439 | | | | |
| | | yes | 1 | 240 | 406 | 1.22E+09 | 1.26743 | |
| | | | 2 | 466 | | | | |
| | | | 3 | 512 | | | | |
| | Exp | no | 1 | 187 | 184 | 5.52E+08 | | |
| | | | 2 | 189 | | | | |
| | | | 3 | 176 | | | | |
| | | yes | 1 | 95 | 132.3 | 3.97E+08 | 0.719203 | 0.3259 |
| | | | 2 | 176 | | | | |
| | | | 3 | 126 | | | | |

TABLE 35-continued

| | | MRSA Data Progression Nov. 7, 2006 Experiment #1 | | | | | | |
|---|---|---|---|---|---|---|---|---|
| | | Methicillin (Meth) | | CFU | AVG | CFU/ml | Meth Effect | Laser Effect (+Meth) |
| D1 | Cont | no | 1 | 251 | 184 | 5.52E+08 | | |
| | | | 2 | 125 | | | | |
| | | | 3 | 176 | | | | |
| | | yes | 1 | 171 | 154 | 4.62E+08 | 0.836957 | |
| | | | 2 | 141 | | | | |
| | | | 3 | 150 | | | | |
| | Exp | no | 1 | 221 | 203.7 | 6.11E+08 | | |
| | | | 2 | 180 | | | | |
| | | | 3 | 210 | | | | |
| | | yes | 1 | 164 | 155.3 | 4.66E+08 | 0.762684 | 1.0087 |
| | | | 2 | 153 | | | | |
| | | | 3 | 149 | | | | |
| E1 | Cont | no | 1 | 142 | 225.3 | 6.76E+08 | | |
| | | | 2 | 268 | | | | |
| | | | 3 | 266 | | | | |
| | | yes | 1 | 147 | 131.3 | 3.94E+08 | 0.58284 | |
| | | | 2 | 121 | | | | |
| | | | 3 | 126 | | | | |
| | Exp | no | 1 | 226 | 258.3 | 7.75E+08 | | |
| | | | 2 | 217 | | | | |
| | | | 3 | 332 | | | | |
| | | yes | 1 | 181 | 214.3 | 6.43E+08 | 0.829677 | 1.632 |
| | | | 2 | 232 | | | | |
| | | | 3 | 230 | | | | |
| F1 | Cont | no | 1 | 223 | 226.7 | 6.80E+08 | | |
| | | | 2 | 260 | | | | |
| | | | 3 | 197 | | | | |
| | | yes | 1 | 197 | 198 | 5.94E+08 | 0.873529 | |
| | | | 2 | 188 | | | | |
| | | | 3 | 209 | | | | |
| | Exp | no | 1 | 223 | 237.7 | 7.13E+08 | | |
| | | | 2 | 256 | | | | |
| | | | 3 | 234 | | | | |
| | | yes | 1 | 206 | 197 | 5.91E+08 | 0.828892 | 0.9949 |
| | | | 2 | 179 | | | | |
| | | | 3 | 206 | | | | |
| G1 | Cont | no | 1 | 214 | 224 | 6.72E+08 | | |
| | | | 2 | 217 | | | | |
| | | | 3 | 241 | | | | |
| | | yes | 1 | 246 | 219.3 | 6.58E+08 | 0.979167 | |
| | | | 2 | 222 | | | | |
| | | | 3 | 190 | | | | |
| | Exp | no | 1 | 243 | 242.7 | 7.28E+08 | | |
| | | | 2 | 261 | | | | |
| | | | 3 | 224 | | | | |
| | | yes | 1 | 193 | 210.7 | 6.32E+08 | 0.868132 | 0.9605 |
| | | | 2 | 237 | | | | |
| | | | 3 | 202 | | | | |
| H1 | Cont | no | 1 | 252 | 255.3 | 7.66E+08 | | |
| | | | 2 | 267 | | | | |
| | | | 3 | 247 | | | | |
| | | yes | 1 | 188 | 192.3 | 5.77E+08 | 0.753264 | |
| | | | 2 | 206 | | | | |
| | | | 3 | 183 | | | | |
| | Exp | no | 1 | 232 | 245 | 7.35E+08 | | |
| | | | 2 | 232 | | | | |
| | | | 3 | 271 | | | | |
| | | yes | 1 | 211 | 199.7 | 5.99E+08 | 0.814966 | 1.0381 |
| | | | 2 | 212 | | | | |
| | | | 3 | 176 | | | | |

TABLE 36

MRSA Dosimetry Progression Nov. 7, 2006 Experiment #2
MRSA Dosimetry Progression
Nov. 7, 2006
First lasing procedure: Both 870 and 930
Second lasing procedure 930 alone

| Parameters | Output Power (W) | Beam Spot (cm) | Area of Spot(cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5 W and 930 at 5 W for 12 min followed by | 10.0 | 1.5 | 1.77 | 720 | 7200 | 4074 | 5.66 | 23.4 | 45.3 |
| Test (1) 930 at 8 W for 6 min | 8.0 | 1.5 | 1.77 | 360 | 2880 | 1630 | 4.53 | 45.3 | 46.8 |
| Test (2) 870 at 5 W and 930 at 5 W for 12 min followed by | 10.0 | 1.5 | 1.77 | 720 | 7200 | 4074 | 5.66 | 21.2 | 45.5 |
| Test (2) 930 at 8 W for 6 min | 8.0 | 1.5 | 1.77 | 360 | 2880 | 1630 | 4.53 | 45.5 | 47.7 |
| Test (3) 870 at 5 W and 930 at 5 W for 12 min followed by | 10.0 | 1.5 | 1.77 | 720 | 7200 | 4074 | 5.66 | 21.6 | 47.0 |
| Test (3) 930 at 8 W for 6 min | 8.0 | 1.5 | 1.77 | 360 | 2880 | 1630 | 4.53 | 47.0 | 49.0 |
| Test (4) 870 at 5.5 W and 930 at 5.5 W for 12 min followed by | 11.0 | 1.5 | 1.77 | 720 | 7920 | 4482 | 6.22 | 20.4 | 50.3 |
| Test (4) 930 at 8 W for 6 min | 8.0 | 1.5 | 1.77 | 360 | 2880 | 1630 | 4.53 | 50.3 | 50.1 |
| Test (5) 870 at 5.5 W and 930 at 5.5 W for 12 min followed by | 11.0 | 1.5 | 1.77 | 720 | 7920 | 4482 | 6.22 | 24.0 | 50.9 |
| Test (5) 930 at 8 W for 6 min | 8.0 | 1.5 | 1.77 | 360 | 2880 | 1630 | 4.53 | 50.9 | 50.2 |
| Test (6) 870 at 5.5 W and 930 at 5.5 W for 12 min followed by | 11.0 | 1.5 | 1.77 | 720 | 7920 | 4482 | 6.22 | 23.0 | 48.2 |
| Test (6) 930 at 8 W for 6 min | 8.0 | 1.5 | 1.77 | 360 | 2880 | 1630 | 4.53 | 48.2 | 48.3 |
| Test (7) 870 at 5 W and 930 at 5 W for 14 min followed by | 10.0 | 1.5 | 1.77 | 840 | 8400 | 4753 | 5.66 | 22.0 | 48.3 |
| Test (7) 930 at 7 W for 8 min | 7.0 | 1.5 | 1.77 | 480 | 3360 | 1901 | 3.96 | 48.3 | 44.2 |
| Test (8) 870 at 5 W and 930 at 5 W for 14 min followed by | 11.0 | 1.5 | 1.77 | 840 | 9240 | 5229 | 6.22 | 22.0 | 47.6 |
| Test (8) 930 at 7 W for 8 min | 7.0 | 1.5 | 1.77 | 480 | 3360 | 1901 | 3.96 | 47.6 | 46.2 |

Independent Report for MRSA studies, 08 Nov. 2006 (MRSA Data Progression Aug. 11 2006 Experiment #2)

Experiment 2—Design:

Eight different laser dosages based on an effective dose established in experiment 1 and previously were used to treat a saline-suspension of logarithmically growing MRSA, labeled A2 to H2.

The treated and a control untreated suspension were diluted and plated in triplicate on trypic soy agar with or without 30 μg/ml methicillin.

After 24 hrs of growth at 37° C. colonies were counted.

Experiment 2—Results:

Comparison of CFU on plates with and without methicillin showed a significant increase in the effectiveness of methicillin in all laser treated samples with the exception of A2 and B2. This data is summarized in tabular form below.

TABLE 37

| Grouping | Fold increase in methicillin sensitivity |
|---|---|
| A2 | 0.84 |
| B2 | 0.91 |
| C2 | 3.20 |
| D2 | 2.44 |
| E2 | 4.33 |
| F2 | 2.13 |
| G2 | 3.47 |
| H2 | 1.62 |

TABLE 38

MRSA Data Progression Nov. 8, 2006 Experiment #2
NOMIR MRSA Study 07-08 Nov. 2006

| | Methicillin (Meth) | | CFU | AVG | CFU/ml | Meth Effect | Laser Effect (+Meth) |
|---|---|---|---|---|---|---|---|
| A2 Cont | no | 1 | 51 | 49.3 | 1.48E+08 | | |
| | | 2 | 43 | | | | |
| | | 3 | 54 | | | | |
| | yes | 1 | 35 | 35.7 | 1.07E+08 | 0.72 | |
| | | 2 | 47 | | | | |
| | | 3 | 25 | | | | |
| Exp | no | 1 | 49 | 47 | 1.41E+08 | | |
| | | 2 | 45 | | | | |
| | | 3 | 47 | | | | |
| | yes | 1 | 39 | 41 | 1.23E+08 | 0.87 | 1.15 |
| | | 2 | 48 | | | | |
| | | 3 | 36 | | | | |

TABLE 38-continued

MRSA Data Progression Nov. 8, 2006 Experiment #2
NOMIR MRSA Study 07-08 Nov. 2006

| | Methicillin (Meth) | | CFU | AVG | CFU/ml | Meth Effect | Laser Effect (+Meth) |
|---|---|---|---|---|---|---|---|
| B2 Cont | no | 1 | 97 | 71.3 | 2.14E+08 | | |
| | | 2 | 47 | | | | |
| | | 3 | 70 | | | | |
| | yes | 1 | 47 | 49.7 | 1.49E+08 | 0.7 | |
| | | 2 | 56 | | | | |
| | | 3 | 46 | | | | |
| Exp | no | 1 | 32 | 34.7 | 1.04E+08 | | |
| | | 2 | 34 | | | | |
| | | 3 | 38 | | | | |
| | yes | 1 | 27 | 26.7 | 8.00E+07 | 0.77 | 0.54 |
| | | 2 | 28 | | | | |
| | | 3 | 25 | | | | |
| C2 Cont | no | 1 | 60 | 55.7 | 1.67E+08 | | |
| | | 2 | 65 | | | | |
| | | 3 | 42 | | | | |
| | yes | 1 | 42 | 55.3 | 1.66E+08 | 0.99 | |
| | | 2 | 71 | | | | |
| | | 3 | 53 | | | | |
| Exp | no | 1 | 35 | 40.3 | 1.21E+08 | | |
| | | 2 | 38 | | | | |
| | | 3 | 48 | | | | |
| | yes | 1 | 16 | 12.7 | 3.80E+07 | 0.31 | 0.23 |
| | | 2 | 12 | | | | |
| | | 3 | 10 | | | | |
| D2 Cont | no | 1 | 108 | 85.3 | 2.56E+08 | | |
| | | 2 | 85 | | | | |
| | | 3 | 63 | | | | |
| | yes | 1 | 20 | 52 | 1.56E+08 | 0.61 | |
| | | 2 | 65 | | | | |
| | | 3 | 71 | | | | |
| Exp | no | 1 | 9 | 9.3 | 2.80E+07 | | |
| | | 2 | 9 | | | | |
| | | 3 | 10 | | | | |
| | yes | 1 | 5 | 2.3 | 7.00E+06 | 0.25 | 0.04 |
| | | 2 | 1 | | | | |
| | | 3 | 1 | | | | |
| E2 Cont | no | 1 | 52 | 59.7 | 1.79E+08 | | |
| | | 2 | 60 | | | | |
| | | 3 | 67 | | | | |
| | yes | 1 | 68 | 62.3 | 1.87E+08 | 1.04 | |
| | | 2 | 66 | | | | |
| | | 3 | 53 | | | | |
| Exp | no | 1 | 8 | 11 | 3.30E+07 | | |
| | | 2 | 12 | | | | |
| | | 3 | 13 | | | | |
| | yes | 1 | 2 | 2.7 | 8.00E+06 | 0.24 | 0.04 |
| | | 2 | 2 | | | | |
| | | 3 | 4 | | | | |
| F2 Cont | no | 1 | 125 | 87.7 | 2.63E+08 | | |
| | | 2 | 73 | | | | |
| | | 3 | 65 | | | | |
| | yes | 1 | 62 | 71 | 2.13E+08 | 0.81 | |
| | | 2 | 64 | | | | |
| | | 3 | 87 | | | | |
| Exp | no | 1 | 37 | 41 | 1.23E+08 | | |
| | | 2 | 43 | | | | |
| | | 3 | 43 | | | | |
| | yes | 1 | 13 | 15.7 | 4.70E+07 | 0.38 | 0.22 |
| | | 2 | 15 | | | | |
| | | 3 | 19 | | | | |
| G2 Cont | no | 1 | 77 | 80 | 2.40E+08 | | |
| | | 2 | 110 | | | | |
| | | 3 | 53 | | | | |
| | yes | 1 | 75 | 83.3 | 2.50E+08 | 1.04 | |
| | | 2 | 92 | | | | |
| | | 3 | 83 | | | | |
| Exp | no | 1 | 26 | 28 | 8.40E+07 | | |
| | | 2 | 28 | | | | |
| | | 3 | 30 | | | | |
| | yes | 1 | 10 | 8.3 | 2.50E+07 | 0.3 | 0.1 |
| | | 2 | 7 | | | | |
| | | 3 | 8 | | | | |

TABLE 38-continued

MRSA Data Progression Nov. 8, 2006 Experiment #2
NOMIR MRSA Study 07-08 Nov. 2006

| | Methicillin (Meth) | | CFU | AVG | CFU/ml | Meth Effect | Laser Effect (+Meth) |
|---|---|---|---|---|---|---|---|
| H2 Cont | no | 1 | 77 | 105.7 | 3.17E+08 | | |
| | | 2 | 156 | | | | |
| | | 3 | 84 | | | | |
| | yes | 1 | 76 | 76.7 | 2.30E+08 | 0.73 | |
| | | 2 | 72 | | | | |
| | | 3 | 82 | | | | |
| Exp | no | 1 | 28 | 28.3 | 8.50E+07 | | |
| | | 2 | 36 | | | | |
| | | 3 | 21 | | | | |
| | yes | 1 | 13 | 12.7 | 3.80E+07 | 0.45 | 0.17 |
| | | 2 | 12 | | | | |
| | | 3 | 13 | | | | |

TABLE 39

Outlined Protocol for NOMIR MRSA study - Nov. 09, 2006
(Nov. 09, 2006 Experiment #3)
Method:

| Time (hrs) | Task | FTE (hrs) |
|---|---|---|
| T −18 | Inoculate overnight culture | 1 |
| | 50 ml directly from glycerol stock | |
| T −4 | Set up starter cultures | 1 |
| | Three dilutions 1:50, 1:125, 1:250 | |
| | Monitor $OD_{600}$ of starter cultures | 4 |
| T 0 | Preparation of plating culture | 1 |
| | At 10:00 am, the culture which is at $OD_{600}$ = 1.0 is diluted 1:300 in PBS (50 mls final volume) and stored at RT for 1 hour. | |
| | (Room temp should be ~25° C.) | |
| T +1 | Seeding of 24-well plates (8 plates in total) | 1 |
| | 2 ml aliquots are dispensed into pre-designated wells in 24-well plates and transferred to NOMIR (8 24-well plates total) | |
| T +2 to +8 | Dilution of treated samples | 4 |
| | After laser treatment, 100 µl from each well is diluted serially to a final dilution of 1:1000 in PBS. | |
| | Plating of treated samples | 2 |
| | 100 µl of final dilution is plated in quintuplicate (5X) on TSB agar with and without 30 µg/ml methicillin. (10 TSB plates per well) | |
| | Plates are incubated at 37° C. 18-24 hrs. | |
| T +24 | Colonies are counted on each plate (160 plates total) | 6 |

TABLE 40

MRSA Dosimetry Progression Nov. 9, 2006 Experiment #3
MRSA Dosimetry Progression
Nov. 9, 2006
First lasing procedure: Both
870 and 930
Second lasing procedure 930
alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5.5 W and 930 at 5.5 W for 12 min followed by | 11.0 | 1.5 | 1.77 | 720 | 7920 | 4482 | 6.22 | 22.0 | 48.1 |
| Test (1) 930 at 8 W for 6 min | 8.0 | 1.5 | 1.77 | 360 | 2880 | 1630 | 4.53 | 48.1 | 47.7 |
| Test (2) 870 at 5.5 W and 930 at 5.5 W for 12 min followed by | 11.0 | 1.5 | 1.77 | 720 | 7920 | 4482 | 6.22 | 22.9 | 48.8 |
| Test (2) 930 at 8 W for 6 min | 8.0 | 1.5 | 1.77 | 360 | 2880 | 1630 | 4.53 | 48.8 | 48.7 |
| Test (3) 870 at 5.5 W and 930 at 5.5 W for 12 min followed by | 11.0 | 1.5 | 1.77 | 720 | 7920 | 4482 | 6.22 | 22.8 | 48.9 |
| Test (3) 930 at 8 W for 6 min | 8.0 | 1.5 | 1.77 | 360 | 2880 | 1630 | 4.53 | 48.9 | 48.9 |
| Test (4) 870 at 5.5 W and 930 at 5.5 W for 12 min followed by | 11.0 | 1.5 | 1.77 | 720 | 7920 | 4482 | 6.22 | 24.0 | 50.3 |
| Test (4) 930 at 8 W for 6 min | 8.0 | 1.5 | 1.77 | 360 | 2880 | 1630 | 4.53 | 50.3 | 50.5 |
| Test (5) 870 at 5 W and 930 at 5 W for 14 min followed by | 10.0 | 1.5 | 1.77 | 840 | 8400 | 4753 | 5.66 | 23.7 | 48.4 |
| Test (5) 930 at 6 W for 9 min | 6.0 | 1.5 | 1.77 | 540 | 3240 | 1833 | 3.40 | 48.4 | 45.0 |
| Test (6) 870 at 5 W and 930 at 5 W for 14 min followed by | 10.0 | 1.5 | 1.77 | 840 | 8400 | 4753 | 5.66 | 23.5 | 49.2 |
| Test (6) 930 at 6 W for 9 min | 6.0 | 1.5 | 1.77 | 540 | 3240 | 1833 | 3.40 | 42.9 | 46.3 |

TABLE 40-continued

MRSA Dosimetry Progression Nov. 9, 2006 Experiment #3
MRSA Dosimetry Progression
Nov. 9, 2006
First lasing procedure: Both
870 and 930
Second lasing procedure 930
alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (7) 870 at 5 W and 930 at 5 W for 14 min followed by | 10.0 | 1.5 | 1.77 | 840 | 8400 | 4753 | 5.66 | 25.6 | 49.9 |
| Test (7) 930 at 6 W for 9 min | 6.0 | 1.5 | 1.77 | 540 | 3240 | 1833 | 3.40 | 49.9 | 46.3 |
| Test (8) 870 at 5 W and 930 at 5 W for 14 min followed by | 10.0 | 1.5 | 1.77 | 840 | 8400 | 4753 | 5.66 | 22.1 | 48.0 |
| Test (8) 930 at 6 W for 9 min | 6.0 | 1.5 | 1.77 | 540 | 3240 | 1833 | 3.40 | 48.0 | 46.0 |

Independent Report for MRSA studies, 09-10 Nov. 2006 MRSA Data Progression Nov. 10, 2006 Experiment #3

Experiment 3—Design:

Eight different laser dosages based on an effective dose established in experiments 1 and 2 and previously were used to treat a saline-suspension of logarithmically growing MRSA, labeled A3 to H3.

The treated and a control untreated suspension were diluted and plated in pentuplicate on trypic soy agar with or without 30 μg/ml methicillin.

After 24 hrs of growth at 37° C. colonies were counted.

Experiment 3—Results:

Comparison of CFU on plates with and without methicillin showed a significant increase in the effectiveness of methicillin in all laser treated samples. This data is summarized in tabular form below.

TABLE 41

| Grouping | Fold increase in methicillin sensitivity |
|---|---|
| A3 | 1.98 |
| B3 | 1.62 |
| C3 | 1.91 |
| D3 | 2.59 |
| E3 | 2.09 |
| F3 | 2.08 |
| G3 | 3.16 |
| H3 | 2.97 |

TABLE 42

MRSA Data Progression Nov. 10, 2006 Experiment #3
NOMIR MRSA Study 09-10 Nov. 2006

| | | Methicillin (Meth) | | CFU | AVG | CFU/ml | Meth Effect | Laser Effect (+M) |
|---|---|---|---|---|---|---|---|---|
| A3 | Cont | no | 1 | 41 | 47 | 1.41E+08 | | |
| | | | 2 | 63 | | | | |
| | | | 3 | 46 | | | | |
| | | | 4 | 49 | | | | |
| | | | 5 | 36 | | | | |
| | | yes | 1 | 35 | 48.4 | 1.45E+08 | 1.03 | |
| | | | 2 | 45 | | | | |
| | | | 3 | 52 | | | | |
| | | | 4 | 66 | | | | |
| | | | 5 | 44 | | | | |
| | Exp | no | 1 | 24 | 31.4 | 9.42E+07 | | |
| | | | 2 | 34 | | | | |
| | | | 3 | 26 | | | | |
| | | | 4 | 33 | | | | |
| | | | 5 | 40 | | | | |
| | | yes | 1 | 23 | 16.2 | 4.86E+07 | 0.52 | 0.33 |
| | | | 2 | 15 | | | | |
| | | | 3 | 14 | | | | |
| | | | 4 | 16 | | | | |
| | | | 5 | 13 | | | | |
| B3 | Cont | no | 1 | 109 | 72 | 2.16E+08 | | |
| | | | 2 | 61 | | | | |
| | | | 3 | 59 | | | | |
| | | | 4 | 61 | | | | |
| | | | 5 | 70 | | | | |
| | | yes | 1 | 61 | 71.4 | 2.14E+08 | 0.99 | |
| | | | 2 | 79 | | | | |
| | | | 3 | 51 | | | | |
| | | | 4 | 68 | | | | |
| | | | 5 | 98 | | | | |
| | Exp | no | 1 | 27 | 31.2 | 9.36E+07 | | |
| | | | 2 | 25 | | | | |

TABLE 42-continued

MRSA Data Progression Nov. 10, 2006 Experiment #3
NOMIR MRSA Study 09-10 Nov. 2006

| | Methicillin (Meth) | | CFU | AVG | CFU/ml | Meth Effect | Laser Effect (+M) |
|---|---|---|---|---|---|---|---|
| | | 3 | 39 | | | | |
| | | 4 | 24 | | | | |
| | | 5 | 41 | | | | |
| | yes | 1 | 9 | 19 | 5.70E+07 | 0.61 | 0.27 |
| | | 2 | 22 | | | | |
| | | 3 | 23 | | | | |
| | | 4 | 25 | | | | |
| | | 5 | 16 | | | | |
| C3 Cont | no | 1 | 46 | 57.6 | 1.73E+08 | | |
| | | 2 | 60 | | | | |
| | | 3 | 60 | | | | |
| | | 4 | 66 | | | | |
| | | 5 | 56 | | | | |
| | yes | 1 | 70 | 58.4 | 1.75E+08 | 1.01 | |
| | | 2 | 54 | | | | |
| | | 3 | 52 | | | | |
| | | 4 | 51 | | | | |
| | | 5 | 65 | | | | |
| Exp | no | 1 | 52 | 38.2 | 1.15E+08 | | |
| | | 2 | 34 | | | | |
| | | 3 | 38 | | | | |
| | | 4 | 34 | | | | |
| | | 5 | 33 | | | | |
| | yes | 1 | 12 | 20.2 | 6.06E+07 | 0.53 | 0.35 |
| | | 2 | 26 | | | | |
| | | 3 | 22 | | | | |
| | | 4 | 24 | | | | |
| | | 5 | 17 | | | | |
| D3 Cont | no | 1 | 50 | 50.6 | 1.52E+08 | | |
| | | 2 | 45 | | | | |
| | | 3 | 55 | | | | |
| | | 4 | 54 | | | | |
| | | 5 | 49 | | | | |
| | yes | 1 | 58 | 51.2 | 1.54E+08 | 1.01 | |
| | | 2 | 46 | | | | |
| | | 3 | 43 | | | | |
| | | 4 | 59 | | | | |
| | | 5 | 50 | | | | |
| Exp | no | 1 | 7 | 9.2 | 2.76E+07 | | |
| | | 2 | 10 | | | | |
| | | 3 | 8 | | | | |
| | | 4 | 9 | | | | |
| | | 5 | 12 | | | | |
| | yes | 1 | 6 | 3.6 | 1.08E+07 | 0.39 | 0.07 |
| | | 2 | 3 | | | | |
| | | 3 | 1 | | | | |
| | | 4 | 5 | | | | |
| | | 5 | 3 | | | | |
| E3 Cont | no | 1 | 47 | 54.8 | 1.64E+08 | | |
| | | 2 | 55 | | | | |
| | | 3 | 71 | | | | |
| | | 4 | 45 | | | | |
| | | 5 | 56 | | | | |
| | yes | 1 | 56 | 50.6 | 1.52E+08 | 0.92 | |
| | | 2 | 48 | | | | |
| | | 3 | 48 | | | | |
| | | 4 | 52 | | | | |
| | | 5 | 49 | | | | |
| Exp | no | 1 | 50 | 53.2 | 1.60E+08 | | |
| | | 2 | 65 | | | | |
| | | 3 | 49 | | | | |
| | | 4 | 46 | | | | |
| | | 5 | 56 | | | | |
| | yes | 1 | 15 | 23.6 | 7.08E+07 | 0.44 | 0.47 |
| | | 2 | 24 | | | | |
| | | 3 | 26 | | | | |
| | | 4 | 27 | | | | |
| | | 5 | 26 | | | | |
| F3 Cont | no | 1 | 57 | 72.4 | 2.17E+08 | | |
| | | 2 | 142 | | | | |
| | | 3 | 62 | | | | |
| | | 4 | 52 | | | | |
| | | 5 | 49 | | | | |

TABLE 42-continued

MRSA Data Progression Nov. 10, 2006 Experiment #3
NOMIR MRSA Study 09-10 Nov. 2006

|  | Methicillin (Meth) | CFU | | AVG | CFU/ml | Meth Effect | Laser Effect (+M) |
|---|---|---|---|---|---|---|---|
|  | yes | 1 | 65 | 53.2 | 1.60E+08 | 0.73 |  |
|  |  | 2 | 50 |  |  |  |  |
|  |  | 3 | 54 |  |  |  |  |
|  |  | 4 | 40 |  |  |  |  |
|  |  | 5 | 57 |  |  |  |  |
| Exp | no | 1 | 29 | 28.4 | 8.52E+07 |  |  |
|  |  | 2 | 39 |  |  |  |  |
|  |  | 3 | 25 |  |  |  |  |
|  |  | 4 | 23 |  |  |  |  |
|  |  | 5 | 26 |  |  |  |  |
|  | yes | 1 | 13 | 9.8 | 2.94E+07 | 0.35 | 0.18 |
|  |  | 2 | 10 |  |  |  |  |
|  |  | 3 | 14 |  |  |  |  |
|  |  | 4 | 5 |  |  |  |  |
|  |  | 5 | 7 |  |  |  |  |
| G3 Cont | no | 1 | 60 | 57.8 | 1.73E+08 |  |  |
|  |  | 2 | 53 |  |  |  |  |
|  |  | 3 | 54 |  |  |  |  |
|  |  | 4 | 66 |  |  |  |  |
|  |  | 5 | 56 |  |  |  |  |
|  | yes | 1 | 56 | 67.6 | 2.03E+08 | 1.17 |  |
|  |  | 2 | 56 |  |  |  |  |
|  |  | 3 | 70 |  |  |  |  |
|  |  | 4 | 63 |  |  |  |  |
|  |  | 5 | 93 |  |  |  |  |
| Exp | no | 1 | 23 | 22.8 | 6.84E+07 |  |  |
|  |  | 2 | 24 |  |  |  |  |
|  |  | 3 | 21 |  |  |  |  |
|  |  | 4 | 21 |  |  |  |  |
|  |  | 5 | 25 |  |  |  |  |
|  | yes | 1 | 9 | 8.4 | 2.52E+07 | 0.37 | 0.12 |
|  |  | 2 | 11 |  |  |  |  |
|  |  | 3 | 5 |  |  |  |  |
|  |  | 4 | 8 |  |  |  |  |
|  |  | 5 | 9 |  |  |  |  |
| H3 Cont | no | 1 | 64 | 72.4 | 2.17E+08 |  |  |
|  |  | 2 | 86 |  |  |  |  |
|  |  | 3 | 72 |  |  |  |  |
|  |  | 4 | 45 |  |  |  |  |
|  |  | 5 | 95 |  |  |  |  |
|  | yes | 1 | 72 | 75.2 | 2.26E+08 | 1.04 |  |
|  |  | 2 | 75 |  |  |  |  |
|  |  | 3 | 71 |  |  |  |  |
|  |  | 4 | 79 |  |  |  |  |
|  |  | 5 | 79 |  |  |  |  |
| Exp | no | 1 | 20 | 23.8 | 7.14E+07 |  |  |
|  |  | 2 | 17 |  |  |  |  |
|  |  | 3 | 23 |  |  |  |  |
|  |  | 4 | 28 |  |  |  |  |
|  |  | 5 | 31 |  |  |  |  |
|  | yes | 1 | 6 | 8.4 | 2.52E+07 | 0.35 | 0.11 |
|  |  | 2 | 12 |  |  |  |  |
|  |  | 3 | 4 |  |  |  |  |
|  |  | 4 | 9 |  |  |  |  |
|  |  | 5 | 11 |  |  |  |  |

TABLE 43

Outlined Protocol for NOMIR MRSA study - Nov. 10, 2006
Method:

| Time (hrs) | Task | FTE (hrs) |
|---|---|---|
| T −18 | Inoculate overnight culture | 1 |
|  | 50 ml directly from glycerol stock |  |
| T −4 | Set up starter cultures | 1 |
|  | Three dilutions 1:50, 1:125, 1:250 |  |
|  | Monitor $OD_{600}$ of starter cultures | 4 |
| T 0 | Preparation of plating culture | 1 |
|  | At 10:00 am, the culture which is at $OD_{600} = 1.0$ is |  |
|  | diluted 1:300 in PBS (50 mls final volume) and stored |  |
|  | at RT for 1 hour. |  |
|  | (Room temp should be ~25° C.) |  |
| T +1 | Seeding of 24-well plates (6 plates in total) | 1 |
|  | 2 ml aliquots are dispensed into pre-designated wells |  |
|  | in 24-well plates and transferred to NOMIR (6 24-well |  |
|  | plates total) |  |

TABLE 43-continued

Outlined Protocol for NOMIR MRSA study - Nov. 10, 2006
Method:

| Time (hrs) | Task | FTE (hrs) |
|---|---|---|
| T +2 to +8 | Dilution of treated samples<br>After laser treatment, 100 μl from each well is diluted serially to a final dilution of 1:1000 in PBS.<br>Plating of treated samples<br>100 μl of final dilution is plated in Quintuplicate (5X) on TSB agar in the following manner:<br>24 well Plate # 1 and 2 with and without 30 μg/ml methicillin.<br>24 well Plate # 3 and 4 with and without μg/ml Penicillin<br>24 well Plate # 5 and 6 with and without μg/ml Erythromycin<br>(10 TSB plates per well)<br>Plates are incubated at 37° C. 18-24 hrs. | 4<br><br>2 |
| T +24 | Colonies are counted on each plate (120 plates total) | 6 |

Experiment 4—Results:

Laser treatment increases sensitivity of MRSA to each antibiotic tested by several fold. This data is summarized below.

| Series | Drug |
|---|---|
| A4 | Methicillin |
| B4 | Methicillin |
| C4 | Penicillin |
| D4 | Penicillin |
| E4 | Erythromycin |
| F4 | Erythromycin |

TABLE 45

| Grouping | Fold increase in antibiotic sensitivity |
|---|---|
| A4 | 2.19 |
| B4 | 2.63 |
| C4 | 2.21 |
| D4 | 3.45 |
| E4 | 50.50 |
| F4 | 9.67 |

TABLE 44

MRSA Dosimetry Progression Nov. 10, 2006 Experiment #4
MRSA Dosimetry Progression
Nov. 10, 2006
First lasing procedure: Both 870 and 930
Second lasing procedure 930 alone

| Parameters | Output Power (W) | Beam Spot (cm) | Area of Spot (cm2) | Time (sec) | Total Energy Joules | Energy Density (J/cm$^2$) | Power Density (W/cm$^2$) | Temp Initial C. | Temp Final C. |
|---|---|---|---|---|---|---|---|---|---|
| Test (1) 870 at 5.5 W and 930 at 5.5 W for 12 min followed by | 11.0 | 1.5 | 1.77 | 720 | 7920 | 4482 | 6.22 | 22.3 | 46.3 |
| Test (1) 930 at 8 W for 6 min (METHICILLIN PLATES) | 8.0 | 1.5 | 1.77 | 360 | 2880 | 1630 | 4.53 | 46.3 | 47.6 |
| Test (2) 870 at 5 W and 930 at 5 W for 14 min followed by | 10.0 | 1.5 | 1.77 | 840 | 8400 | 4753 | 5.66 | 23.1 | 47.1 |
| Test (2) 930 at 6 W for 9 min (METHICILLIN PLATES) | 6.0 | 1.5 | 1.77 | 540 | 3240 | 1833 | 3.40 | 47.1 | 44.3 |
| Test (3) 870 at 5.5 W and 930 at 5.5 W for 12 min followed by | 11.0 | 1.5 | 1.77 | 720 | 7920 | 4482 | 6.22 | 24.4 | 48.4 |
| Test (3) 930 at 8 W for 6 min (PENICILLIN G PLATES) | 8.0 | 1.5 | 1.77 | 360 | 2880 | 1630 | 4.53 | 48.4 | 47.1 |
| Test (4) 870 at 5 W and 930 at 5 W for 14 min followed by | 10.0 | 1.5 | 1.77 | 840 | 8400 | 4753 | 5.66 | 23.3 | 47.9 |
| Test (4) 930 at 6 W for 9 min (PENICILLIN G PLATES) | 6.0 | 1.5 | 1.77 | 540 | 3240 | 1833 | 3.40 | 47.9 | 45.0 |
| Test (5) 870 at 5.5 W and 930 at 5.5 W for 12 min followed by | 11.0 | 1.5 | 1.77 | 720 | 7920 | 4482 | 6.22 | 22.9 | 50.2 |
| Test (5) 930 at 8 W for 6 min (ERYTHROMYCIN PLATES) | 8.0 | 1.5 | 1.77 | 360 | 2880 | 1630 | 4.53 | 50.2 | 51.6 |
| Test (6) 870 at 5 W and 930 at 5 W for 14 min followed by | 10.0 | 1.5 | 1.77 | 840 | 8400 | 4753 | 5.66 | 24.2 | 50.3 |
| Test (6) 930 at 6 W for 9 min (ERYTHROMYCIN PLATES) | 6.0 | 1.5 | 1.77 | 540 | 3240 | 1833 | 3.40 | 50.3 | 43.6 |

Independent Report for MRSA studies, 10-11 Nov. 2006 (MRSA Data Progression Nov. 10, 2006 Experiment #4)

Experiment 4—Design:

Two different laser dosages based on an effective dose established in previous experiments were used to treat a saline-suspension of logarithmically growing MRSA, labeled A4 to F4.

The treated and a control untreated suspension were diluted and plated in pentuplicate on trypic soy agar with or without 30 μg/ml methicillin (Groups A4 and B4), 0.5 μg/ml penicillin G (Groups C4 and D4) or 4 μg/ml erythromycin (Groups E4 and F4).

After 24 hrs of growth at 37° C. colonies were counted.

TABLE 46

MRSA Data Progression Nov. 10, 2006 Experiment #4
NOMIR MRSA Study 10-11 Nov. 2006

| | | Drug? | | CFU | AVG | CFU/ml | Drug Effect | Laser Effect (+Drug) |
|---|---|---|---|---|---|---|---|---|
| A4 | Cont | no | 1 | 84 | 92 | 2.76E+08 | | |
| | | | 2 | 95 | | | | |
| | | | 3 | 69 | | | | |
| | | | 4 | 106 | | | | |
| | | | 5 | 106 | | | | |
| | | yes | 1 | 97 | 86.2 | 2.59E+08 | 0.94 | |
| | | | 2 | 104 | | | | |
| | | | 3 | 82 | | | | |
| | | | 4 | 58 | | | | |
| | | | 5 | 90 | | | | |
| | Exp | no | 1 | 82 | 84.4 | 2.53E+08 | | |
| | | | 2 | 80 | | | | |
| | | | 3 | 85 | | | | |
| | | | 4 | 90 | | | | |
| | | | 5 | 85 | | | | |
| | | yes | 1 | 37 | 36.2 | 1.09E+08 | 0.43 | 0.42 |
| | | | 2 | 33 | | | | |
| | | | 3 | 36 | | | | |
| | | | 4 | 39 | | | | |
| | | | 5 | 36 | | | | |
| B4 | Cont | no | 1 | 86 | 105 | 3.15E+08 | | |
| | | | 2 | 142 | | | | |
| | | | 3 | 105 | | | | |
| | | | 4 | 97 | | | | |
| | | | 5 | 95 | | | | |
| | | yes | 1 | 149 | 132.6 | 3.98E+08 | 1.26 | |
| | | | 2 | 101 | | | | |
| | | | 3 | 119 | | | | |
| | | | 4 | 153 | | | | |
| | | | 5 | 141 | | | | |
| | Exp | no | 1 | 73 | 88.8 | 2.66E+08 | | |
| | | | 2 | 84 | | | | |
| | | | 3 | 109 | | | | |
| | | | 4 | 89 | | | | |
| | | | 5 | 89 | | | | |
| | | yes | 1 | 46 | 42.4 | 1.27E+08 | 0.48 | 0.32 |
| | | | 2 | 34 | | | | |
| | | | 3 | 42 | | | | |
| | | | 4 | 44 | | | | |
| | | | 5 | 46 | | | | |
| C4 | Cont | no | 1 | 211 | 143.8 | 4.31E+08 | | |
| | | | 2 | 138 | | | | |
| | | | 3 | 114 | | | | |
| | | | 4 | 145 | | | | |
| | | | 5 | 111 | | | | |
| | | yes | 1 | 106 | 108.4 | 3.25E+08 | 0.75 | |
| | | | 2 | 99 | | | | |
| | | | 3 | 102 | | | | |
| | | | 4 | 113 | | | | |
| | | | 5 | 122 | | | | |
| | Exp | no | 1 | 84 | 90.2 | 2.71E+08 | | |
| | | | 2 | 84 | | | | |
| | | | 3 | 87 | | | | |
| | | | 4 | 107 | | | | |
| | | | 5 | 89 | | | | |
| | | yes | 1 | 25 | 30.4 | 9.12E+07 | 0.34 | 0.28 |
| | | | 2 | 33 | | | | |
| | | | 3 | 19 | | | | |
| | | | 4 | 33 | | | | |
| | | | 5 | 42 | | | | |
| D4 | Cont | no | 1 | 111 | 123.6 | 3.71E+08 | | |
| | | | 2 | 110 | | | | |
| | | | 3 | 135 | | | | |
| | | | 4 | 107 | | | | |
| | | | 5 | 155 | | | | |
| | | yes | 1 | 101 | 132.8 | 3.98E+08 | 1.07 | |
| | | | 2 | 111 | | | | |
| | | | 3 | 138 | | | | |
| | | | 4 | 132 | | | | |
| | | | 5 | 182 | | | | |
| | Exp | no | 1 | 73 | 75.6 | 2.27E+08 | | |
| | | | 2 | 86 | | | | |
| | | | 3 | 93 | | | | |
| | | | 4 | 74 | | | | |
| | | | 5 | 52 | | | | |
| | | yes | 1 | 14 | 23.8 | 7.14E+07 | 0.31 | 0.18 |
| | | | 2 | 23 | | | | |
| | | | 3 | 22 | | | | |
| | | | 4 | 29 | | | | |
| | | | 5 | 31 | | | | |
| E4 | Cont | no | 1 | 122 | 125.6 | 3.77E+08 | | |
| | | | 2 | 154 | | | | |
| | | | 3 | 127 | | | | |
| | | | 4 | 116 | | | | |
| | | | 5 | 109 | | | | |
| | | yes | 1 | 199 | 127 | 3.81E+08 | 1.01 | |
| | | | 2 | 125 | | | | |
| | | | 3 | 103 | | | | |
| | | | 4 | 101 | | | | |
| | | | 5 | 107 | | | | |
| | Exp | no | 1 | 17 | 17.6 | 5.28E+07 | | |
| | | | 2 | 20 | | | | |
| | | | 3 | 18 | | | | |
| | | | 4 | 21 | | | | |
| | | | 5 | 12 | | | | |
| | | yes | 1 | 0 | 0.4 | 1.20E+06 | 0.02 | 0 |
| | | | 2 | 1 | | | | |
| | | | 3 | 0 | | | | |
| | | | 4 | 0 | | | | |
| | | | 5 | 1 | | | | |
| F4 | Cont | no | 1 | 117 | 177.8 | 5.33E+08 | | |
| | | | 2 | 126 | | | | |
| | | | 3 | 318 | | | | |
| | | | 4 | 166 | | | | |
| | | | 5 | 162 | | | | |
| | | yes | 1 | 186 | 155.4 | 4.66E+08 | 0.87 | |
| | | | 2 | 170 | | | | |
| | | | 3 | 121 | | | | |
| | | | 4 | 132 | | | | |
| | | | 5 | 168 | | | | |
| | Exp | no | 1 | 60 | 66.4 | 1.99E+08 | | |
| | | | 2 | 54 | | | | |
| | | | 3 | 60 | | | | |
| | | | 4 | 102 | | | | |
| | | | 5 | 56 | | | | |
| | | yes | 1 | 2 | 5.8 | 1.74E+07 | 0.09 | 0.04 |
| | | | 2 | 7 | | | | |
| | | | 3 | 6 | | | | |
| | | | 4 | 6 | | | | |
| | | | 5 | 8 | | | | |

Example XXIII

In Vivo Safety Testing - Human Patient

Following the in vitro fibroblast studies, the inventor performed a dosimetry titration on himself to ascertain the safe, maximum level of energy and time of exposure that could be delivered to human dermal tissue without burning or otherwise damaging the irradiated tissues.

The methodology he used was to irradiate his great toe for varying lengths of time and power settings with the NIMELS laser. The results of this self-exposure experiment are described below.

TABLE 47

| | Combined Wavelength Dosimetries | | | | | | |
|---|---|---|---|---|---|---|---|
| PARAMETERS | OUTPUT POWER (W) | BEAM SPOT (CM) | AREA OF SPOT (CM²) | TIME (SEC) | TOTAL ENERGY JOULES | ENERGY DENSITY (J/CM²) | POWER DENSITY (W/CM²) |
| 870 nm | 1.5 | 1.5 | 1.77 | 250 | 375 | 212 | 0.85 |
| 930 nm | 1.5 | 1.5 | 1.77 | 250 | 375 | 212 | 0.85 |
| Combined | 3.0 | 1.5 | 1.77 | 250 | 750 | 424 | 1.70 |

TABLE 48

| | Dosimetry at $\lambda$ = 930 nm | | | | | | |
|---|---|---|---|---|---|---|---|
| PARAMETERS | OUTPUT POWER (W) | BEAM SPOT (CM) | AREA OF SPOT (CM2) | TIME (SEC) | TOTAL ENERGY JOULES | ENERGY DENSITY (J/CM²) | POWER DENSITY (W/CM²) |
| 930 nm | 3.0 | 1.5 | 1.77 | 120 | 360 | 204 | 1.70 |

Time/Temperature assessments were charted to ensure the thermal safety of these laser energies on human dermal tissues (data not shown). In one laser procedure, he exposed his great toe to both 870 nm and 930 nm for up to 233 seconds, while measuring toenail surface temperature with a laser infrared thermometer. He found that using the above dosimetries, at a surface temperature of 37.5° C., with 870 nm and 930 nm together with a combined Power Density of 1.70 W/cm², pain resulted and the laser was turned off.

In a second laser procedure, he exposed his great toe to 930 nm for up to 142 seconds, while again measuring toenail surface temperature with a laser infrared thermometer. He found that, at a surface temperature of 36° C., with 930 nm alone at a Power Density of 1.70 W/cm², pain resulted and the laser was turned off.

Example XXIV

In Vivo Safety Testing - Limited Clinical Pilot Study

Following the experiment above, additional patients with onychomycosis of the feet were treated. These patients were all unpaid volunteers, who provided signed informed consent. The principle goal of this limited pilot study was to achieve the same level of fungal decontamination in vivo, as was obtained in vitro with the NIMELS laser device. We also decided to apply the maximum time exposure and temperature limit that was tolerated by the inventor during his self-exposure experiment.

In a highly controlled and monitored environment, three to five laser exposure procedures were performed on each subject. Four subjects were recruited and underwent the treatment. Subjects provided signed informed consent, were not compensated, and were informed they could withdraw at any time, even during a procedure.

The dosimetry that was used for the treatment of the first subject was the same as that used during the inventor's self-exposure (shown above). The temperature parameters on the surface of the nail also were equivalent to the temperatures found by the inventor on self-exposure.

The treated toes showed significantly reduced Tinea pedis and scaling surrounding the nail beds, which indicated a decontamination of the nail plate that was acting as a reservoir for the fungus. The control nails were scraped with a cross-cut tissue bur, and the shavings were saved to be plated on mycological media. The treated nails were scraped and plated in the exact same manner.

For culturing the nail scrapings, Sabouraud dextrose agar (2% dextrose) medium was prepared with the following additions: chloramphenicol (0.04 mg/ml), for general fungal testing; chloramphenicol (0.04 mg/ml) and cycloheximide (0.4 g/ml), which is selective for dermatophytes; chloramphenicol (0.04 mg/ml) and griseofulvin (20 μg/ml), which served as a negative control for fungal growth.

Nine-day mycological results for Treatment #1 and Treatment #2 (performed three days after Treatment #1) were the same, with a dermatophyte growing on the control toenail plates, and no growth on the treated toenail plates. Treated plates did not show any growth whereas untreated control culture plates showed significant growth.

Figure 18:
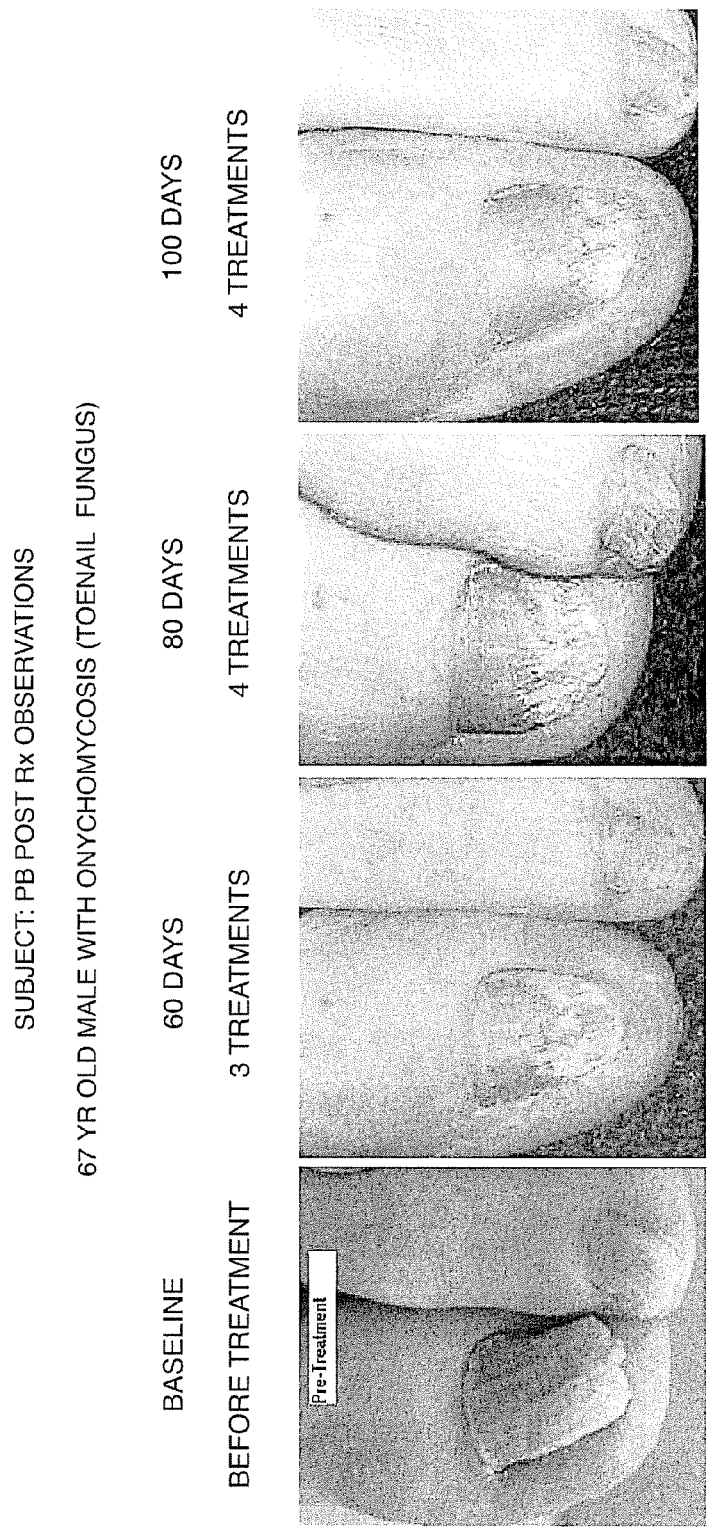
FIG. 18 is a composite showing the improvement over time in the appearance of the nail of a typical onychomycosis patient treated according to the methods of the invention. Panel A shows the baseline, an infected toenail before treatment; panel B shows the toenail 60 days post treatment; panel C shows the toenail 80 days post treatment; and panel D shows the toenail 100 days post treatment.

The first subject was followed for 120 days, and received four treatments under the same protocol. FIG. 18 shows a comparison of the pretreatment (A), 60 days post-treatment (B), 80 days post-treatment (C), and 120 days post-treatment (D) toenails. Notably, healthy and non-infected nail plate was covering 50% of the nail area and growing from healthy cuticle after 120 days.

While certain embodiments have been described herein, it will be understood by one skilled in the art that the methods, systems, and apparatus of the present invention may be embodied in other specific forms without departing from the spirit thereof. The present embodiments are therefore to be considered in all respects as illustrative and not restrictive of the present invention. It is understood that the Human nail acts as a refractory lens, and disperses and/or reflects portions of the NIMELS infrared energy. Hence, Porcine skin dose/tolerance studies were performed to titrate maximum NIMELS dosimetry without burn/damage to tissues. Porcine skin was used as a model for human skin. These studies were carried out in compliance with the Animal Protection Act and according to the NIH Guide for the Care and Use of Laboratory Animals. These tests are shown below.

Porcine Skin Dose/Tolerance Studies

TABLE 49

| Dose ID | Parameters (nm) | Output Power (W) | Beam Spot (cm) | Area of Spot (cm2) | Time (sec) | Total Energy (Joules) | Energy Density (J/cm2) | Power Density (W/cm2) |
|---|---|---|---|---|---|---|---|---|
| 1 | 870 | 1.3 | 1.5 | 1.77 | 120 | 156 | 88 | 0.74 |
|   | 930 | 1.3 | 1.5 | 1.77 | 120 | 156 | 88 | 0.74 |
|   | Combined | 2.6 | 1.5 | 1.77 | 120 | 312 | 177 | 1.47 |
|   | 930 Alone | 2.6 | 1.5 | 1.77 | 50 | 130 | 74 | 1.47 |
| 2 | 870 | 1.3 | 1.5 | 1.77 | 140 | 182 | 103 | 0.74 |
|   | 930 | 1.3 | 1.5 | 1.77 | 140 | 182 | 103 | 0.74 |
|   | Combined | 2.6 | 1.5 | 1.77 | 140 | 364 | 206 | 1.47 |
|   | 930 Alone | 2.6 | 1.5 | 1.77 | 60 | 156 | 88 | 1.47 |
| 3 | 870 | 1.3 | 1.5 | 1.77 | 160 | 208 | 118 | 0.74 |
|   | 930 | 1.3 | 1.5 | 1.77 | 160 | 208 | 118 | 0.74 |
|   | Combined | 2.6 | 1.5 | 1.77 | 160 | 416 | 235 | 1.47 |
|   | 930 Alone | 2.6 | 1.5 | 1.77 | 70 | 182 | 103 | 1.47 |
| 4 | 870 | 1.3 | 1.5 | 1.77 | 180 | 234 | 132 | 0.74 |
|   | 930 | 1.3 | 1.5 | 1.77 | 180 | 234 | 132 | 0.74 |
|   | Combined | 2.6 | 1.5 | 1.77 | 180 | 468 | 265 | 1.47 |
|   | 930 Alone | 2.6 | 1.5 | 1.77 | 80 | 208 | 118 | 1.47 |
| 5 | 870 | 1.5 | 1.5 | 1.77 | 100 | 150 | 85 | 0.85 |
|   | 930 | 1.5 | 1.5 | 1.77 | 100 | 150 | 85 | 0.85 |
|   | Combined | 3 | 1.5 | 1.77 | 100 | 300 | 170 | 1.7 |
|   | 930 Alone | 3 | 1.5 | 1.77 | 40 | 120 | 68 | 1.7 |
| 6 | 870 | 1.5 | 1.5 | 1.77 | 120 | 180 | 102 | 0.85 |
|   | 930 | 1.5 | 1.5 | 1.77 | 120 | 180 | 102 | 0.85 |
|   | Combined | 3 | 1.5 | 1.77 | 120 | 360 | 204 | 1.7 |
|   | 930 Alone | 3 | 1.5 | 1.77 | 50 | 150 | 85 | 1.7 |
| 7 | 870 | 1.5 | 1.5 | 1.77 | 140 | 210 | 119 | 0.85 |
|   | 930 | 1.5 | 1.5 | 1.77 | 140 | 210 | 119 | 0.85 |
|   | Combined | 3 | 1.5 | 1.77 | 140 | 420 | 238 | 1.7 |
|   | 930 Alone | 3 | 1.5 | 1.77 | 60 | 180 | 102 | 1.7 |
| 8 | 870 | Control | Control | Control | Control | Control | Control | Control |
|   | 930 | Control | Control | Control | Control | Control | Control | Control |
|   | Combined | Control | Control | Control | Control | Control | Control | Control |
|   | 930 Alone | Control | Control | Control | Control | Control | Control | Control |
| 9 | 870 | 1.15 | 2 | 3.14 | 100 | 115 | 37 | 0.37 |
|   | 930 | 1.15 | 2 | 3.14 | 100 | 115 | 37 | 0.37 |
|   | Combined | 2.3 | 2 | 3.14 | 100 | 230 | 73 | 0.73 |
|   | 930 Alone | 2.3 | 2 | 3.14 | 40 | 92 | 29 | 0.73 |
| 10 | 870 | 1.15 | 2 | 3.14 | 120 | 138 | 44 | 0.37 |
|   | 930 | 1.15 | 2 | 3.14 | 120 | 138 | 44 | 0.37 |
|   | Combined | 2.3 | 2 | 3.14 | 120 | 276 | 88 | 0.73 |
|   | 930 Alone | 2.3 | 2 | 3.14 | 50 | 115 | 37 | 0.73 |
| 11 | 870 | 1.15 | 2 | 3.14 | 140 | 161 | 51 | 0.37 |
|   | 930 | 1.15 | 2 | 3.14 | 140 | 161 | 51 | 0.37 |
|   | Combined | 2.3 | 2 | 3.14 | 140 | 322 | 102 | 0.73 |
|   | 930 Alone | 2.3 | 2 | 3.14 | 60 | 138 | 44 | 0.73 |
| 12 | 870 | 1.15 | 2 | 3.14 | 160 | 184 | 59 | 0.37 |
|   | 930 | 1.15 | 2 | 3.14 | 160 | 184 | 59 | 0.37 |
|   | Combined | 2.3 | 2 | 3.14 | 160 | 368 | 117 | 0.73 |
|   | 930 Alone | 2.3 | 2 | 3.14 | 70 | 161 | 51 | 0.73 |
| 13 | 870 | 1.15 | 2 | 3.14 | 180 | 207 | 66 | 0.37 |
|   | 930 | 1.15 | 2 | 3.14 | 180 | 207 | 66 | 0.37 |
|   | Combined | 2.3 | 2 | 3.14 | 180 | 414 | 132 | 0.73 |
|   | 930 Alone | 2.3 | 2 | 3.14 | 80 | 184 | 59 | 0.73 |
| 14 | 870 | 1.15 | 2 | 3.14 | 200 | 230 | 73 | 0.37 |
|   | 930 | 1.15 | 2 | 3.14 | 200 | 230 | 73 | 0.37 |
|   | Combined | 2.3 | 2 | 3.14 | 200 | 460 | 146 | 0.73 |
|   | 930 Alone | 2.3 | 2 | 3.14 | 90 | 207 | 66 | 0.73 |
| 15 | 870 | 1.15 | 2 | 3.14 | 240 | 276 | 88 | 0.37 |
|   | 930 | 1.15 | 2 | 3.14 | 240 | 276 | 88 | 0.37 |
|   | Combined | 2.3 | 2 | 3.14 | 240 | 552 | 176 | 0.73 |
|   | 930 Alone | 2.3 | 2 | 3.14 | 120 | 276 | 88 | 0.73 |
| 20 | 870 | Control | Control | Control | Control | Control | Control | Control |
|   | 930 | Control | Control | Control | Control | Control | Control | Control |
|   | Combined | Control | Control | Control | Control | Control | Control | Control |
|   | 930 Alone | Control | Control | Control | Control | Control | Control | Control |

Example XXV

Non-Thermal NIMELS Interaction

Evidence for non-thermal NIMELS interaction:

It was demonstrated through experimentation (in vitro water bath studies), that the temperatures reached in the in vitro NIMELS experimentation, were not high enough in and of themselves to neutralize the pathogens.

In the chart that follows, it can clearly be seen that when simple *E. coli* Bacteria were challenged at 47.5 C continuously for 8 minutes in a test tube in a water bath, they achieved 91% growth of colonies. Therefore, it was demonstrated essentially that the NIMELS reaction is indeed photo-chemical in nature, and occurs in the absence of exogenous drugs and/or dyes.

TABLE 50

Water Bath Test
Bacteria placed in PBS on bench at room temperature for 3 hours; then in water bath at 47.5 C. for 8 min and plated.

| | Control<br>Aug. 26, 2005 | | Final<br>Aug. 26, 2005 |
|---|---|---|---|
| A | 73 | D | 64 |
| B | 82 | E | 73 |
| C | 75 | F | 72 |
| | Average %<br>Growth | | 90.9%<br>Lived | after 47.5 C. for 8 min.

What is claimed is:

1. A method comprising:
reducing the bacterial proton-motive force (Δp-plas-Bact) and the bacterial plasma transmembrane potential (ΔΨ-plas-bact) across a bacterial cell membrane in bacterial cells of a target site in order to inhibit bacterial cellular anabolic pathways and weaken resistance mechanisms against antibacterial molecules, the reducing step comprising:
combining λn and Tn to irradiate a target site at a NIMELS dosimetry, concurrently reducing bacterial chemiosmotic electrochemical energy that is required for cellular anabolic reactions in bacteria at said target site; and
simultaneously or sequentially administering an antibacterial agent or agents to said target site, co-targeting a cellular anabolic reaction or reactions, wherein inhibition of one or more cellular anabolic pathways at said target site is effectuated;
wherein λn corresponds to irradiation at wavelengths in at least one of the wavelength range of about 865 nm to about 875 nm and the wavelength range of about 925 nm to about 935 nm;
wherein Tn corresponds to a treatment time in the range of 50 seconds to about 1200 seconds; and
wherein the NIMELS dosimetry corresponds to irradiation of the target site at a power density of about 0.25 W/cm$^2$ to about 40 W/cm$^2$ and an energy density of about 50 J/cm$^2$ to about 700 J/cm$^2$.

2. The method of claim 1, wherein λn corresponds to irradiation at wavelengths in both the wavelength range of about 865 nm to about 875 nm and the wavelength range of about 925 nm to about 935 nm.

3. The method of claim 1, wherein λn corresponds to irradiation at wavelengths in the wavelength range of about 865 nm to about 875 nm.

4. The method of claim 1, wherein λn corresponds to irradiation at wavelengths in the wavelength range of about 925 nm to about 935 nm.

5. The method of claim 1, wherein the target site is an in vivo target site in a human or animal subject, the target cells comprises a bacterial contaminate in the site, and wherein combining λn and Tn to irradiate a target site at a NIMELS dosimetry comprises irradiating the target site without causing substantial thermal damage to the subject at target site.

6. The method of claim 1 comprising combining λn and Tn to irradiate a target site, where inhibition of bacterial cellular anabolic pathways can be further enhanced with the simultaneous or sequential administration of a pharmacological agent or agents that also inhibit bacterial anabolic pathways (the co-targeting pharmacologically of a bacterial anabolic pathway or pathways with (λn and Tn)).

7. The method of claim 1, comprising potentiating the antibacterial agent with a Nimels effect number Ne of at least 1.

8. The method of claim 1, wherein the antibacterial agent comprises at least one from the list consisting of: a macrolide, a ketolide, a quinolone, a β-lactam, and any combination or salt thereof.

9. The method of claim 1, wherein the antibacterial agent comprises an erythromycin.

10. The method of claim 1, wherein the antibacterial agent comprises a tetracyline.

11. The method of claim 1, wherein the antibacterial agent comprises a penicillin.

12. The method of claim 1, wherein the antibacterial agent comprises bacitracin.

13. The method of claim 1, wherein the antibacterial agent comprises ciprofloxacin.

14. The method of claim 1, wherein the reducing step comprises mechano-optically modifying a thermodynamic interaction of the bacterial cell membrane.

15. A method comprising:
reducing the bacterial proton-motive force (Δp-plas-Bact) and the bacterial plasma trans-membrane potential (ΔΨ-plas-bact) across a bacterial cell membrane in bacterial cells of a target site in order to potentiate one or more antibacterial agent to counteract resistance mechanisms in the bacteria, so that the antibacterial agent can inhibit the growth or proliferation of the bacteria at a lower concentration than would be necessary in the absence of the reducing step, the reducing step comprising:
combining λn and Tn to irradiate a target site at a NIMELS dosimetry, concurrently reducing bacterial chemiosmotic electrochemical energy that is required for cellular anabolic reactions in bacteria at said target site; and
simultaneously or sequentially administering an antibacterial agent to said target site, co-targeting cellular anabolic reactions wherein inhibition of one or more cellular anabolic pathways at said target site is effectuated;
wherein λn corresponds to irradiation at wavelengths in at least one of the wavelength range of about 865 nm to about 875 nm and the wavelength range of about 925 nm to about 935 nm;
wherein Tn corresponds to a treatment time in the range of 50 seconds to about 1200 seconds; and
wherein the NIMELS dosimetry corresponds to irradiation of the target site at a power density of about 0.25 W/cm$^2$ to about 40 W/cm$^2$ and an energy density of about 50 J/cm$^2$ to about 700 J/cm$^2$.

16. The method of claim 15, wherein the targeted bacterial pathway is the maintenance of bacterial cell membrane selective permeability and the bacterial plasma trans-membrane potential (ΔΨ-plas-bact), and the co-targeting pharmacological agent is a cationic antibacterial peptide that is selective for the negatively charged surface of bacterial membranes, which leads to the co-targeting and weakening of bacterial plasma trans-membrane potential (ΔΨ-plas-bact).

17. The method of claim 15, comprising potentiating the antibacterial agent with a Nimels effect number Ne of at least 1.

18. The method of claim 17, wherein the antibacterial agent comprises daptomycin.

19. The method of claim 15, wherein the reducing step comprises mechano-optically modifying a thermodynamic interaction of a cell membrane of the bacterial cells.

20. A method comprising:

reducing Fungal Plasma Trans-Membrane Potential ($\Delta\Psi$-plas-fungi) or the fungal mitochondrial proton-motive force ($\Delta$p-mito-fungi) in fungal cells of a target site in order to potentiate an antifungal agent or agents to counteract a resistance mechanisms in the fungi, so that the antifungal agent or agents can once again inhibit the growth and/or proliferation of said fungi at a lower concentration than would be necessary in the absence of the present method, the reducing step comprising:

combining $\lambda$n and Tn to irradiate a target site at a NIMELS dosimetry, thereby reducing Fungal Plasma Trans-Membrane Potential ($\Delta\Psi$-plas-fungi) and/or the fungal mitochondrial proton-motive force ($\Delta$p-mito-Fungi) at said target site; and simultaneously or sequentially administering an antifungal agent or agents to said target site, co-targeting fungal cellular anabolic reactions wherein inhibition of one or more fungal cellular anabolic pathways at said target site is effectuated;

wherein $\lambda$n corresponds to irradiation at wavelengths in at least one of the wavelength range of about 865 nm to about 875 nm and the wavelength range of about 925 nm to about 935 nm;

wherein Tn corresponds to a treatment time in the range of 50 seconds to about 1200 seconds; and wherein the NIMELS dosimetry corresponds to irradiation of the target site at a power density of about 0.25 W/cm$^2$ to about 40 W/cm$^2$ and an energy density of about 50 J/cm$^2$ to about 700 J/cm$^2$.

21. The method of claim 19, wherein $\lambda$n corresponds to irradiation at wavelengths in both the wavelength range of about 865 nm to about 875 nm and the wavelength range of about 925 nm to about 935 nm.

22. The method of claim 19, wherein $\lambda$n corresponds to irradiation at wavelengths the wavelength range of about 865 nm to about 875 nm.

23. The method of claim 19, wherein $\lambda$n corresponds to irradiation at wavelengths in the wavelength range of about 925 nm to about 935 nm.

24. The method of claim 19, wherein the target site is an in vivo target site in a human or animal subject, the target cells comprises a fungal contaminate in the site, and wherein combining $\lambda$n and Tn to irradiate a target site at a NIMELS dosimetry comprises irradiating the target site without causing substantial thermal damage to the subject at target site.

25. The method of claim 19, comprising combining $\lambda$n and Tn to irradiate a target site, where inhibition of fungal cellular anabolic pathways can be further enhanced with the simultaneous or sequential administration of a pharmacological agent that also inhibits a fungal anabolic pathway (the co-targeting of a fungal anabolic pathway with ($\lambda$n and Tn).

26. The method of claim 19, comprising potentiating the antifungal agent with a Nimels effect number Ne of at least 1.

27. The method of claim 19, wherein the antifungal agent comprises at least one from the list consisting of: polyenes, azoles, imidazoles, triazoles, allylamines, echinocandins, cicopirox, flucytosine, griseofulvin, amorolofine, sodarins, and any combination or salt thereof.

28. The method of claim 19, wherein the antifungal agent comprises terbinafine.

29. The method of claim 19, wherein the antifungal agent comprises itraconazole.

30. The method of claim 19, wherein the reducing step comprises reducing $\Delta\Psi$-plas-fungi and $\Delta$p-mito-Fungi.

31. The method of claim 29, wherein the step of reducing step comprises mechano-optically modifying a thermodynamic interaction of a cell membrane of the bacterial cells.

32. A method of reducing the bacterial proton-motive force ($\Delta$p-plas-Bact) and the bacterial plasma trans-membrane potential ($\Delta\Psi$-plas-bact) across a bacterial cell membrane in bacterial cells of a target site at which at least one antibacterial agent has been administered in order to inhibit bacterial cellular anabolic pathways and weaken resistance mechanisms against antibacterial molecules comprising:

combining $\lambda$n and Tn to irradiate a target site at a NIMELS dosimetry, concurrently reducing bacterial chemiosmotic electrochemical energy that is required for cellular anabolic reactions in bacteria at said target site; and wherein $\lambda$n corresponds to irradiation at wavelengths in at least one of the wavelength range of about 865 nm to about 875 nm and the wavelength range of about 925 nm to about 935 nm;

wherein Tn corresponds to a treatment time in the range of 50 seconds to about 1200 seconds; and wherein the NIMELS dosimetry corresponds to irradiation of the target site at a power density of about 0.25 W/cm$^2$ to about 40W/cm$^2$ and an energy density of about 50 J/cm$^2$ to about 700 J/cm$^2$.

\* \* \* \* \*